United States Patent
Mandel

(10) Patent No.: US 10,111,936 B2
(45) Date of Patent: *Oct. 30, 2018

(54) METAL-GLYCOPROTEIN COMPLEXES AND PHOTODYNAMIC THERAPY OF IMMUNE PRIVILEGED SITES WITH SAME

(71) Applicant: Theralase Technologies, Inc., Toronto (CA)

(72) Inventor: Arkady Mandel, Toronto (CA)

(73) Assignee: Theralase Technologies, Inc., Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/291,025

(22) Filed: Oct. 11, 2016

(65) Prior Publication Data

US 2017/0042976 A1    Feb. 16, 2017

Related U.S. Application Data

(63) Continuation-in-part of application No. 15/000,651, filed on Jan. 19, 2016.

(60) Provisional application No. 62/166,120, filed on May 25, 2015, provisional application No. 62/105,080, filed on Jan. 19, 2015.

(51) Int. Cl.
| | |
|---|---|
| *A61K 38/40* | (2006.01) |
| *A61K 31/555* | (2006.01) |
| *A61K 41/00* | (2006.01) |
| *A61K 45/06* | (2006.01) |
| *A61N 5/06* | (2006.01) |
| *A61N 5/10* | (2006.01) |
| *A61K 9/00* | (2006.01) |
| *A61K 49/00* | (2006.01) |
| *A61K 33/24* | (2006.01) |

(52) U.S. Cl.
CPC ............ *A61K 38/40* (2013.01); *A61K 9/0009* (2013.01); *A61K 31/555* (2013.01); *A61K 33/24* (2013.01); *A61K 41/0057* (2013.01); *A61K 45/06* (2013.01); *A61K 49/0021* (2013.01); *A61N 5/062* (2013.01); *A61N 5/10* (2013.01); *A61N 2005/0659* (2013.01); *A61N 2005/1098* (2013.01)

(58) Field of Classification Search
CPC ....................................................... A61K 33/24
See application file for complete search history.

(56) References Cited

U.S. PATENT DOCUMENTS

| | | | |
|---|---|---|---|
| 6,962,910 B2 * | 11/2005 | Brewer | C07F 15/0026 514/184 |
| 7,001,991 B2 | 2/2006 | Faulk | |
| 7,612,057 B2 | 11/2009 | Brewer et al. | |
| 7,809,428 B2 | 10/2010 | Elmaleh et al. | |
| 8,148,360 B2 | 4/2012 | Brewer et al. | |
| 8,445,475 B2 | 5/2013 | Brewer et al. | |
| 2011/0288023 A1 | 11/2011 | Kamei et al. | |
| 2012/0088729 A1 | 4/2012 | Zhang et al. | |
| 2012/0264802 A1 | 10/2012 | Wharton et al. | |

FOREIGN PATENT DOCUMENTS

| | | |
|---|---|---|
| CN | 104072607 A | 10/2014 |
| DE | 102006024528 A1 | 11/2007 |
| WO | 02094271 A1 | 11/2002 |
| WO | 2007134595 A2 | 11/2007 |
| WO | 2013020204 A1 | 2/2013 |
| WO | 2013158550 A1 | 10/2013 |
| WO | 2014145428 A2 | 9/2014 |

OTHER PUBLICATIONS

Antonarakis et al., "Ruthenium-based chemotherapeutics: are they ready for prime time?", Cancer Chemother Pharmacol. 66(1): pp. 1-9 (2010).

Arenas et al., "Photodynamic inactivation of *Staphylococcus aureus* and methicillin-resistant *Staphylococcus aureus* with Ru(II)-based type I/type II photosensitizers", Photodiagnosis Photodyn Ther. 10(4): pp. 615-625 (2013).

Bergamo et al., "Biological role of adduct formation of the ruthenium(III) complex NAMI-A with serum albumin and serum transferrin", Invest New Drugs. 21(4):401-11 (2003).

Bergamo et al., "Ruthenium anticancer compounds: myths and realities of the emerging metal-based drugs", Dalton Trans. 40(31): pp. 7817-7823 (2011).

Biju et al., "Chemical modifications and bioconjugate reactions of nanomaterials for sensing, imaging, drug delivery and therapy", Chem Soc Rev. Feb. 7, 2014;43(3):744-764. doi: 10.1039/c3cs60273g.

Bruijnincx et al. "Controlling platinum, ruthenium, and osmium reactivity for anticancer drug design". Advances in Inorganic Chemistry 61: p. 1-62 (2009).

Chatterjee et al. "Nitrite reduction mediated by the complex Ru III (EDTA)". Dalton Trans 43(36):13596-13600 (2014).

(Continued)

*Primary Examiner* — Rei Tsang Shiao
(74) *Attorney, Agent, or Firm* — Caesar Rivise, PC

(57) ABSTRACT

Compositions of the invention include glycoproteins, such as transferrin, and metal-based coordination complexes, which are preferably chemotherapeutic compounds and more preferably tunable photodynamic compounds. The compositions are useful as in vivo diagnostic agents, and as therapeutic agents for treating or preventing diseases including those that involve hyperproliferating cells in their etiology, such as cancer. Compositions of the invention are further capable of destroying microbial cells, such as bacteria, fungi, and protozoa, and destroying viruses. Treatment methods of the invention can treat conditions throughout the body, including conditions located across the blood-brain barrier, the retina-blood barrier and the blood-cerebrospinal fluid barrier.

17 Claims, 40 Drawing Sheets

(56) References Cited

OTHER PUBLICATIONS

Chen et al. "Polyion complex vesicles for photoinduced intracellular delivery of amphiphilic photosensitizer". J Am Chem Soc. 2014, 136(1):157-163. doi: 10.1021/ja406992w. Epub Dec. 26, 2013.
Derycke et al., Transferrin-conjugated liposome targeting of photosensitizer AlPcS4 to rat bladder carcinoma cells. J. Natl Cancer Inst. 96, 1620-1630 (2004).
Donnelly et al., "Drug Delivery Systems for Photodynamic Therapy", Recent Patents on Drug Delivery & Formulation 3: pp. 1-7 (2009).
Garcia et al. "Binding of [Cr(phen)3]3+ to transferrin at extracellular and endosomal pHs: Potential application in photodynamic therapy". Biochim Biophys Acta 1840: pp. 2695-2701 (2014).
Gaspar et al. "Targeted delivery of transferrin-conjugated liposomes to an orthotopic model of lung cancer in nude rats". J. Aerosol Med. Pulm. Drug Deliv. 25(0): pp. 1-9 (2012).
Gijsens et al. "Targeting of the photocytotoxic compound AlPcS4 to Hela cells by transferrin conjugated PEG-liposomes". Int J Cancer 101: 78-85 (2002).
Graf et al. Redox activation of metal-based prodrugs as a strategy for drug delivery. Adv. Drug Deliv. Rev. 64(11): 993-1004 (2012).
Groessl et al., "Reactivity of anticancer metallodrugs with serum proteins: new insights from size exclusion chromatography-ICP-MS and ESI-MS", J Anal at Spectrom. 25(3): pp. 305-313 (2010).
Guo et al., "Transferrin serves as a mediator to deliver organometallic ruthenium(II) anticancer complexes into cells", Inorg Chem. 52(9): pp. 5328-5338 (2013).
He et al. "Triple-responsive expansile nanogel for tumor and mitochondria targeted photosensitizer delivery". Biomaterials 35(35): pp. 9546-9553 (2014).
Heger et al. "Apoferritin applications in medicine". Nanomedicine (Lond.) 9(14): pp. 2233-2245 (2014).
Kratz et al., "The binding properties of two antitumor ruthenium(III) complexes to apotransferrin", J Biol Chem. 269 (4): pp. 2581-2588 (1994).
Maham et al. "Protein-based nanomedicine platforms for drug delivery". Small 5(15): pp. 1706-1721 (2009).
Mazuryk et al., "Interaction of apo-transferrin with anticancer ruthenium complexes NAMI-A and its reduced form", J Inorg Biochem. 116: pp. 11-18 (2012).
Muehlmann et al., "Liposomal photosensitizers: potential platforms for anticancer photodynamic therapy". Braz J Med Biol Res 44 (8): pp. 729-737 (2011).
Nkepang et al. "Folate Receptor-mediated Enhanced and Specific Delivery of Far-red Light-activatable Prodrugs of Combretastatin A-4 to FR-positive Tumor". Bioconjug Chem. 25: pp. 2175-2188 (2014).
Paszko et al. Transferrin conjugation does not increase the efficiency of liposomal Foscan during in vitro photodynamic therapy of oesophageal cancer. Eur J Pharm Sci. 48(1-2):202-210 (2013).
Pongratz et al., "Transferrin binding and transferrin-mediated cellular uptake of the ruthenium coordination compound KP1019, studied by means of AAS, ESI-MS and CD spectroscopy", J. Anal. At. Spectrom.,19: pp. 46-51 (2004).
Rizvi et al. "PDT Dose Parameters Impact Tumoricidal Durability and Cell Death Pathways in a 3D Ovarian Cancer Model." Photochemistry and photobiology 89(4): pp. 942-952 (2013).
Sardar et al. "Direct observation of key photoinduced dynamics in a potential nano-delivery vehicle of cancer drugs". Phys Chem Chem Phys. 17: pp. 166-177 (2015).
Steere et al., "Biochemical and structural characterization of recombinant human serum transferrin from rice (*Oryza sativa* L.)." J Inorg Biochem. 116C: pp. 37-44 (2012).
Szwed et al. "Relationship between therapeutic efficacy of doxorubicin-transferrin conjugate and expression of P-glycoprotein in chronic erythromyeloblastoid leukemia cells sensitive and resistant to doxorubicin". Cell Oncol (Dordr). 37: pp. 421-428 (2014).
Temizel et al. "Delivery of lipophilic porphyrin by liposome vehicles: Preparation and Photodynamic therapy activity against cancer cell lines". Photodiagnosis Photodyn Ther. 11: pp. 537-545 (2014).
Wong et al. "Carbon nanotubes for delivery of small molecule drugs". Adv Drug Deliv Rev. 65: pp. 1964-2015 (2013).
Yang et al. "The advancing uses of nano-graphene in drug delivery". Expert Opin Drug Deliv. 2014: pp. 1-12.
Yin et al. "Upconverting Nanoparticles with a Mesoporous TiO2 Shell for Near-Infrared-Triggered Drug Delivery and Synergistic Targeted Cancer Therapy". Chemistry Eur J. 20: pp. 14012-14017 (2014).
Yu et al. "Development of Therapeutic Au-Methylene Blue Nanoparticles for Targeted Photodynamic Therapy of Cervical Cancer Cells". ACS Appl Mater Interfaces. pp. A-J (2014).
Yuan et al. "Self-Assembled Nanoparticles Based on PEGylated Conjugated Polyelectrolyte and Drug Molecules for Image-Guided Drug Delivery and Photodynamic Therapy". ACS Appl Mater Interfaces 6: pp. 14903-14910 (2014).
Zhang et al., "Expression, purification, and characterization of recombinant human transferrin from rice (*Oryza sativa* L.)." Protein Expr Purif. 74(1); pp. 69-79 (2010).
Zhang et al. "Transferrin-mediated fullerenes nanoparticles as $Fe^{2+}$-dependent drug vehicles for synergistic anti-tumor efficacy". Biomaterials 37: pp. 353-366 (2015).
Zhen et al. "Tumor vasculature targeted photodynamic therapy for enhanced delivery of nanoparticles". ACS Nano. 8 (6): pp. 6004-6013 (2014).
International Search Report of PCT/IB2016/050253 dated May 2, 2016.
Belikov, VG. Pharmaceutical Chemistry, Moscow, High School, 1993, pp. 43-47.
Arsene et al. (2011). The binding properties of some novel ruthenium (III) complexes with human serum transferrin. Biopolymers and Cell, 27(2), 141-146.
Fong et al. (2015). A novel class of ruthenium-based photosensitizers effectively kills in vitro cancer cells and in vivo tumors. Photochemical and Photobiological Sciences, 14, 2014-2023.
Hoshino et al. (1995). In vitro cytotoxicities and in vivo distribution of transferrin-platinum(II) complex. Journal of Pharmaceutical Sciences, American Chemical Society and American Pharmaceutical Association, 84(2), 216-221.
Kratz et al. (1996). Comparison of the antiproliferative activity of two antitumour ruthenium(III) complexes with their apotransferrin and transferrin-bound forms in a human colon cancer cell line. Metal-based Drugs, 3(1), 15-23.
Li et al. (2013). Protein binding by dinuclear polypyridyl ruthenium(II) complexes and the effect of cucurbit[10]uril encapsulation. Dalton Transactions, 42, 8868-8877.
Martinez et al. (2011). Interactions of arene-Ru(II)-chloroquine complexes of known antimalarial and antitumor activity with human serum albumin (HSA) and transferrin. Journal of Inorganic Biochemistry, Elsevier Inc, 105, 39-45.
Pessoa et al. (2010). Transport of therapeutic vanadium and ruthenium complexes by blood plasma components. Current Medicinal Chemistry, 17, 3701-3738.
Yao et al. (2013). Interaction of manganese(II) complex with apotransferrin and the apotransferrin enhanced anticancer activities. Spectrochimica Acta Part A: Molecular and Biomolecular Spectroscopy, 105, 207-212.
Zhao et al. (2014). Mixed-ligand ruthenium polypyridyl complexes as apoptosis inducers in cancer cells, the cellular translocation and the important role of ROS-mediated signaling. Dalton Transactions, 43(45), 17017-17028.
European Search Report dated May 24, 2018 in counterpart application EP 16739852.

* cited by examiner

FIG. 8A TLD1433
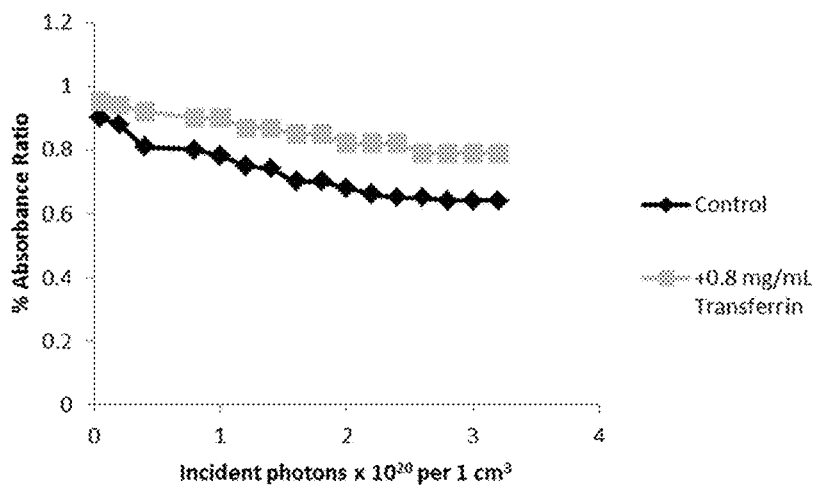
FIG. 8B TLD143310
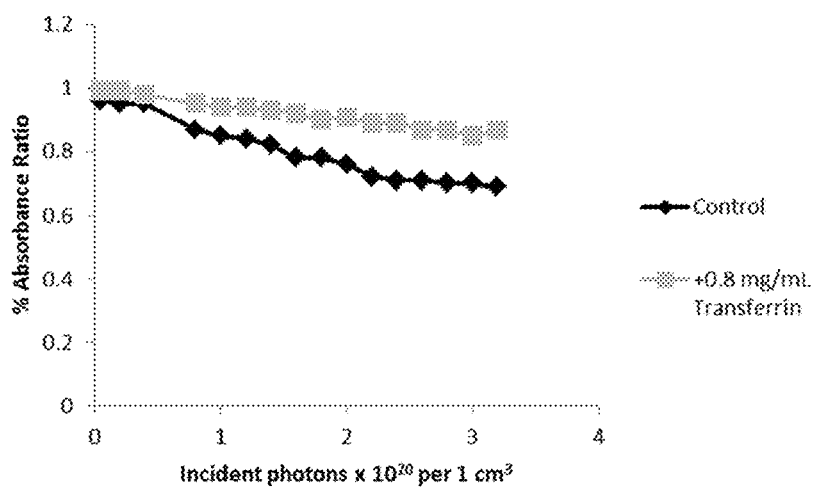
FIG. 8C TLDOsH2dppn
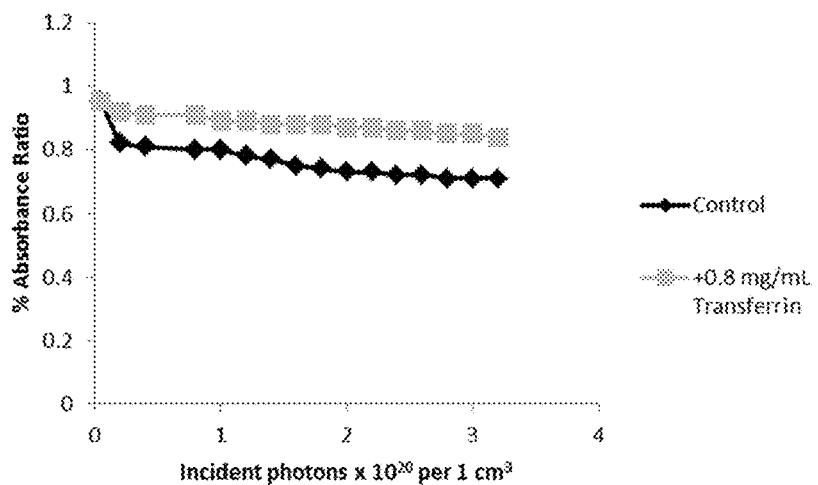

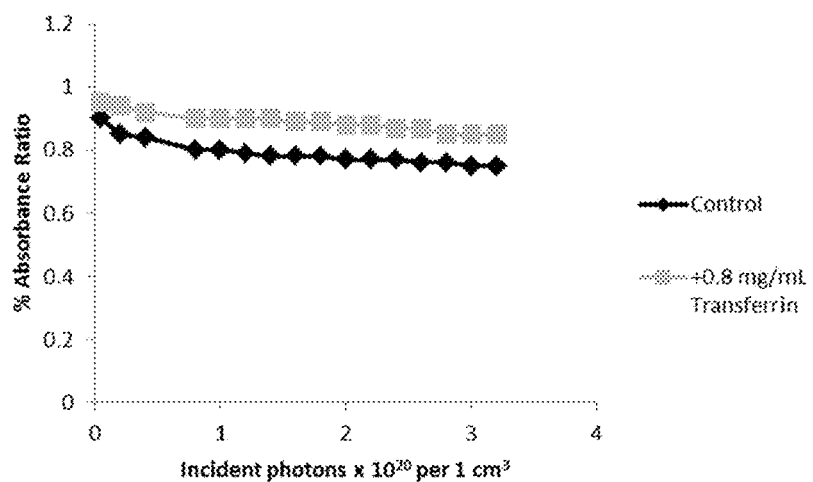
FIG. 9A TLD1433
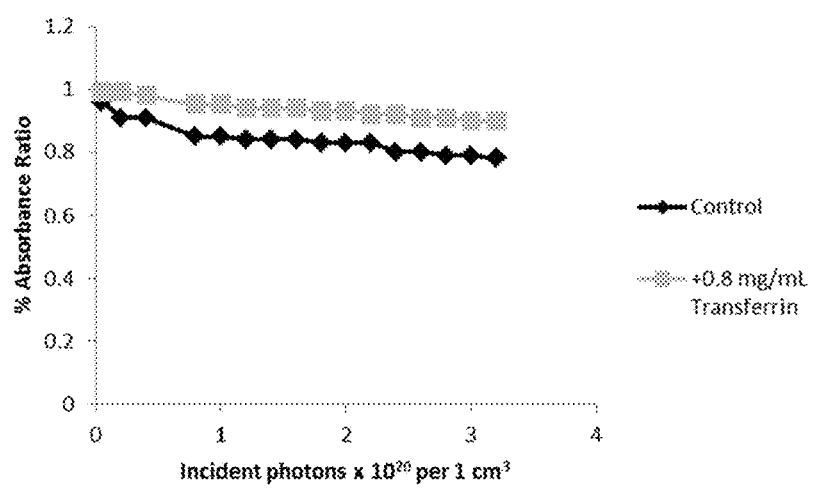
FIG. 9B TLD143310
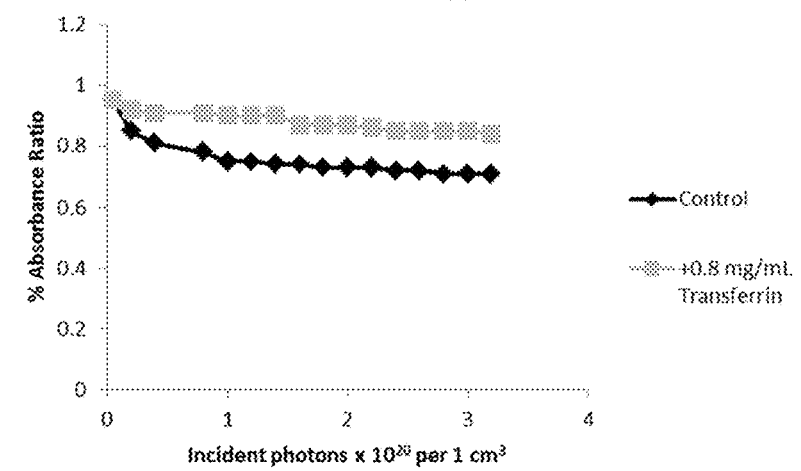
FIG. 9C TLDOsH2dppn

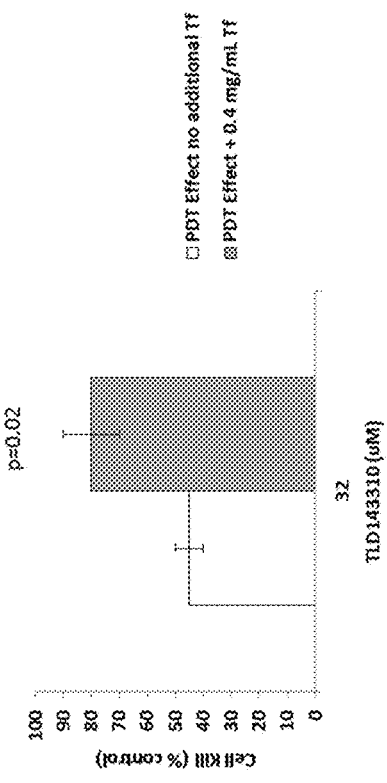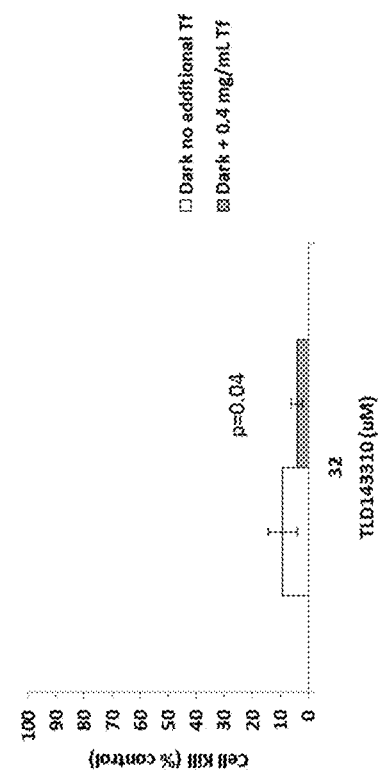
FIG. 18A  FIG. 18B  FIG. 18C  FIG. 18D

Infrared absorbance stability of 10μM TLD1433 GS6-81G in pH 7.4 $HPO_4$ buffer, 10μM Optiferrin, and 10μM apo-hTf $\lambda$ (nm)

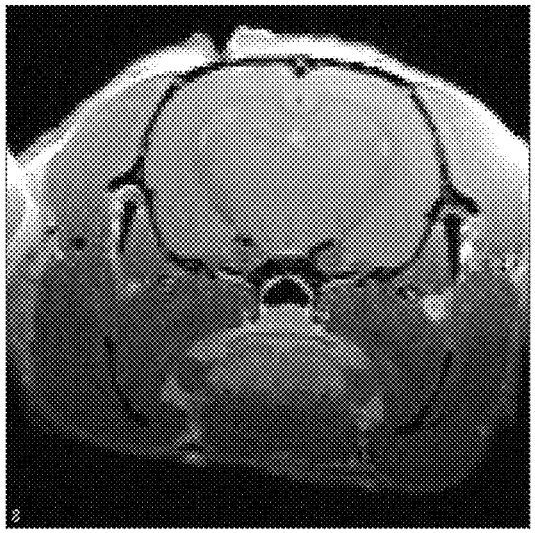 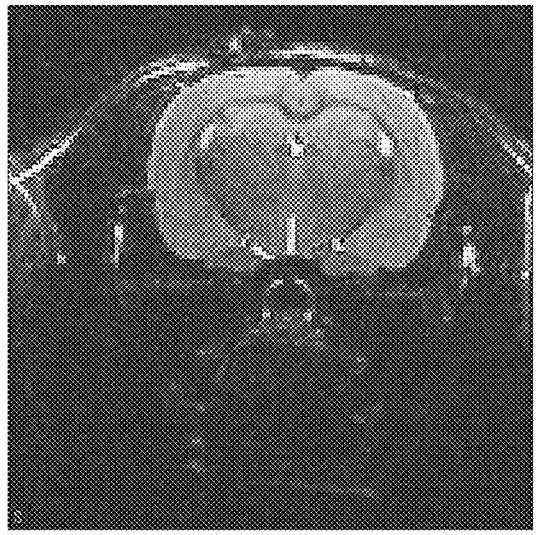
FIG. 36A  FIG. 36B
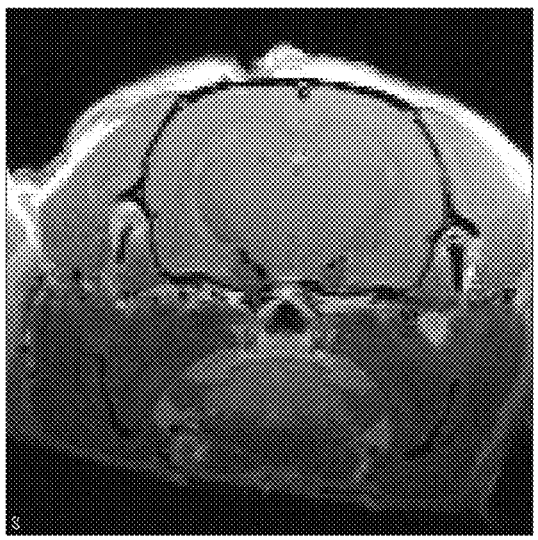 
FIG. 36C  FIG. 36D

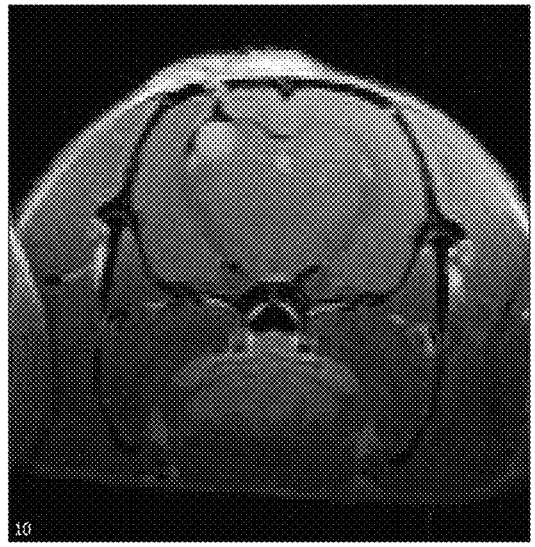
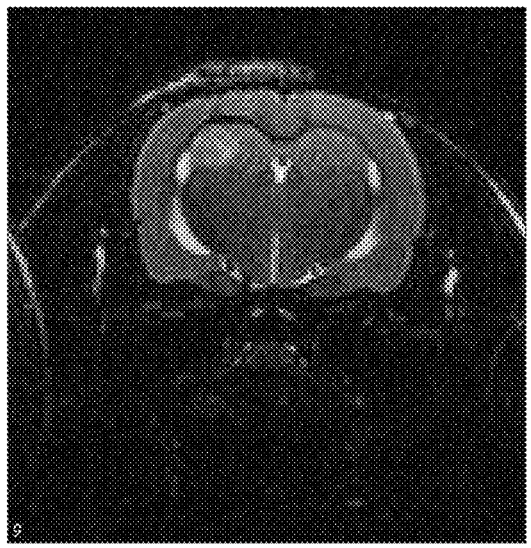
FIG. 36I            FIG. 36J
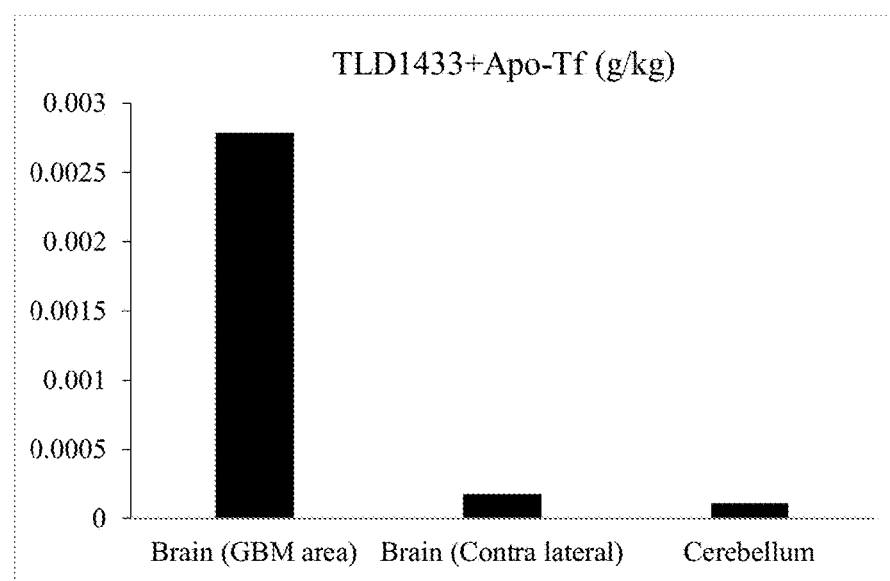
FIG. 37

METAL-GLYCOPROTEIN COMPLEXES AND PHOTODYNAMIC THERAPY OF IMMUNE PRIVILEGED SITES WITH SAME

BACKGROUND OF THE INVENTION

1. Field of Invention

This invention relates to metal-based coordination complexes, and more particularly to photodynamic therapy using metal-glycoprotein complexes as photo dynamic compounds.

2. Description of Related Art

Photodynamic therapy (PDT) is currently an active area of research for the treatment of diseases associated with hyperproliferating cells such as cancer and non-malignant lesions. The development of new photodynamic compounds (PDCs or photosensitizers, PSs) for photodynamic therapy (PDT) has been increasingly focused on metallosupramolecular complexes derived from metals. For example, WO 2013158550 A1 and WO 2014145428 A2 disclose metal-based PDCs useful as in vivo diagnostic agents, as therapeutic agents for treating or preventing diseases that involve unwanted and/or hyperproliferating cell etiology, including cancer, as agents for treating infectious diseases, and as agents for pathogen disinfection and/or sterilization. U.S. Pat. Nos. 6,962,910, 7,612,057, 8,445,475 and 8,148,360 disclose supramolecular metal complexes capable of cleaving DNA when irradiated low energy visible light with or without molecular oxygen.

Delivery of metal-based coordination complexes and PDCs to biological targets can pose a challenge, which many have attempted to address.

For example, US 20120264802 discloses photosensitizer compounds based on functionalized fullerenes useful in targeted PDT, and methods of use thereof.

WO 2013020204 A1 discloses biodegradable polymeric nanoparticles comprising an inner core formed of a photodynamic agent capable of being activated to generate cytotoxic singlet oxygen. These nanoparticles have anti-cell proliferation activity and are useful in treating both cancerous and non-cancerous conditions including actinic keratosis, psoriasis and acne vulgaris. Preferably, the photodynamic agent is a hypocrellin B derivative while the polymeric nanoparticle comprises polyglycolic acid, polylactic acid or poly(lactide-co-glycolide). Hypocrellin-comprising nanoparticles are demonstrated to be activated by light or hydrogen peroxide.

US20110288023 discloses modified Transferrin (Tf) molecules and conjugates of the Tf molecules with a therapeutic agent. Also disclosed are methods of treating cancer wherein the therapeutic agents are chemotherapeutic agents. The modified Tf molecules improve the delivery of the conjugated therapeutic agent to a target tissue.

WO 2002094271 A1 discloses a homogeneous conjugate for targeting and treating diseased cells wherein the conjugate comprises an anti-cancer drug and a targeting protein, wherein said anti-cancer drug is selected from the group consisting of heat sensitizers, photosensitizers and apoptosis inducing compounds, a method for making such a conjugate, and methods for using the conjugate. The targeting protein is preferably transferrin.

U.S. Pat. No. 7,001,991 discloses a homogeneous conjugate for targeting and treating diseased cells wherein the conjugate comprises an anti-cancer drug and a targeting protein, wherein said anti-cancer drug is selected from the group consisting of heat sensitizers, photosensitizers and apoptosis inducing compounds, a method for making such a conjugate, and methods for using the conjugate. The targeting protein is preferably transferrin.

U.S. Pat. No. 7,809,428 discloses PDT methods for treatment of vulnerable plaques by selectively targeting and/or eliminating the inflammatory components of vulnerable plaques. In a preferred embodiment, photosensitizer compositions are coupled to macromolecular carriers that target T cells of vulnerable plaques. These macromolecular carriers can be targeted to, for example, IL-10, receptor, monocyte inflammatory protein-1 and receptors thereof and transferrin. Such macromolecular carriers can be, for example, antibodies against these biomolecules, ligands binding the same or analogs thereof, including, but not limited to monoclonal antibodies that recognize CD1, CD2, CD3, CD4, CDS, CD6, CD7, CDB, CD25, CD28, CD44, CD71 or transferrin.

Large (>500 Da) PSs are difficult to apply topically. Non-selectivity of delivery is another problem. Various patch- and film-based topical application formulations and methods of enhanced delivery of PSs directly into cancer cells have been proposed to overcome both difficulty of delivery of large (>500 Da) PS molecules and non-selectivity of the delivery. They include various patch- and film-based topical application formulations (Donnelly et al 2009), redox activation (Graf, Lippard, 2012), receptor-mediated delivery (Nkepang et al., 2014), photoinduced delivery (Chen et al., 2014; Yin et al., 2014; Sardar et al., 2014), liposomes (Temizel et al., 2014; Muehlmann et al., 2011), and delivery using nanoparticles including fullerenes (Biju, 2014; Yuan, Liu, 2014; Zhen et al., 2014; Wong et al., 2013; Yang et al., 2014; He et al., 2014). Combining of transferrin with fullerenes is also proposed (Zhang et al., 2015) as well as conjugation of PS-loaded liposomes with many molecules (folate, growth factors, glycoproteins such as transferrin, glycolipids) receptors for which are upregulated in cancer cells (Muehlmann et al., 2011; Nkepang et al., 2014). PEGylated AIPcS4-loaded liposomes conjugated with transferrin were used against cervical cancer cells (Gijsens et al., 2002). Exploration of Tf conjugation on the efficiency of liposome-encapsulated PS Foscan, a chlorine-based photosensitizer, in PDT of esophageal cancer was, however, not successful, likely due to the destabilization of the liposomes (Paszko et al., 2013).

Protein-based delivery systems include systems based on albumin (nanoparticles system), small heat shock protein, viral capsid and apoferritin (protein cage systems) used for doxorubicin delivery, soy protein (film-based system) for methylene blue delivery (MaHam et al., 2009). Apoferritin (i.e. Ferritin that is not combined with iron, a protein of 450 kDa) was used to encapsulate various cytostatic anticancer drugs: doxorubicin, carboplatin, cisplatin, daunorubicin although immune response to apoferritin may be a drawback (Heger et al., 2014). Among PCs, encapsulation of Methylene blue into apo-ferritin allowed increasing singlet oxygen production and enhancement of cytotoxic effects on cells (Heger et al., 2014, review).

The use of transferrin with liposomes containing aluminum phthalocyanine tetrasulfonate (LiposomesAlPcS$_4$) is disclosed by Derycke et al., 2014; Gaspar et al., 2012.

None of the foregoing references explicitly propose the use of transferrin in combination with metal-based photosensitizers. Such use was disclosed by the inventor in US 20160206653 A1.

Despite the foregoing developments, it is still desired to provide improved compositions and methods for delivering PDCs to biological targets. It is further desired to provide increased efficacy of selective uptake of PDCs by biological targets. It is further desired to improve intracellular uptake of Ruthenium, Ruthenium-Rhodium and Osmium-based photosensitizers predominantly by cancer cells and tumor tissues. It is further desired to increase PDC efficacy at longer wavelengths. It is further desired to improve absorbance, ROS production and PDT effect of the Ruthenium, Ruthenium-Rhodium and Osmium-based photosensitizers. It is further desired to improve the PDT effect in hypoxia. It is further desired to improve targeting of immune privileged sites.

BRIEF SUMMARY OF THE INVENTION

A first aspect of the invention comprises a composition comprising:

a metal-binding glycoprotein; and a chemotherapeutic compound containing at least one transition metal preferably selected from the group consisting of Ru, Rh and Os, wherein the composition has at least one of the following enhanced properties relative to the chemotherapeutic compound without the glycoprotein: (a) increased uptake by cancer cells; (b) increased uptake by tumors; (c) increased efficacy at wavelengths longer than 600 nm; (d) increased efficacy at wavelengths less than or equal to 600 nm; (e) improved absorbance at wavelengths longer than 600 nm; (f) improved absorbance at wavelengths less than or equal to 600 nm; (g) increased production of reactive oxygen species; (h) increased photodynamic therapy effect under non-hypoxic conditions; (i) increased photodynamic therapy effect under hypoxic conditions; (j) increased LD50; (k) increased MTD; (l) increased photostability; and (m) increased shelf-life.

In certain embodiments, the glycoprotein is transferrin and the chemotherapeutic compound has the formula (I):

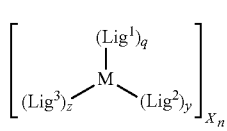
(I)

including hydrates, solvates, pharmaceutically acceptable salts, prodrugs and complexes thereof, wherein:

M at each occurrence is independently a transition metal, which is preferably selected from the group consisting of osmium, ruthenium and rhodium;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2, 3, 4, or 5;

q is independently at each occurrence 0, 1, or 2;

y is independently at each occurrence 0, 1, or 2;

z is independently at each occurrence 1, 2, or 3;

$Lig^1$ is a bidentate ligand that at each occurrence is each independently selected from the group consisting of

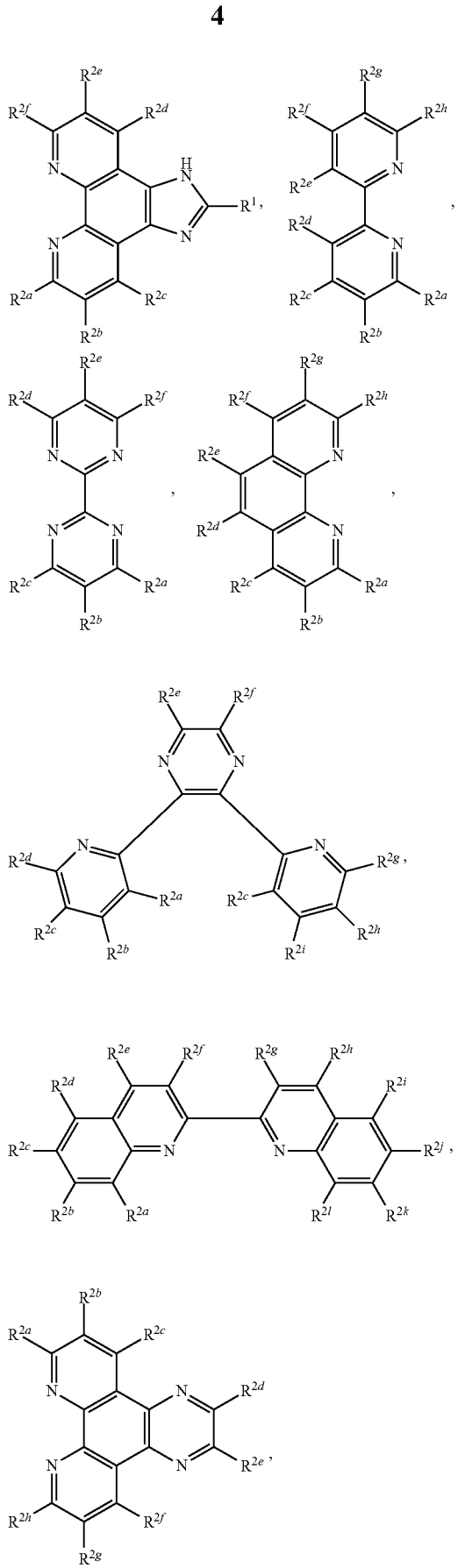

-continued
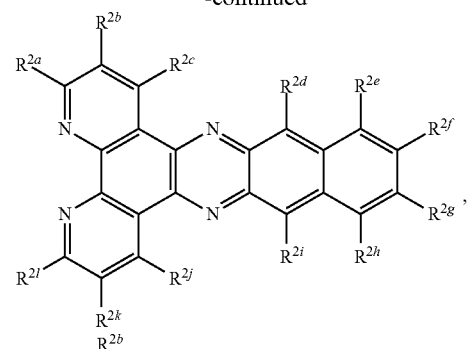
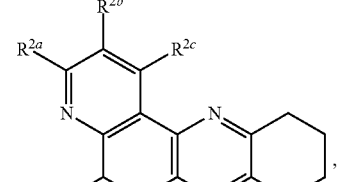
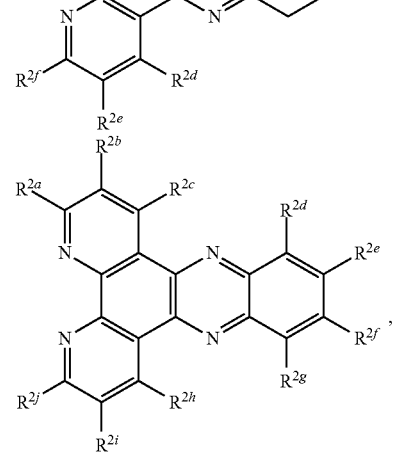
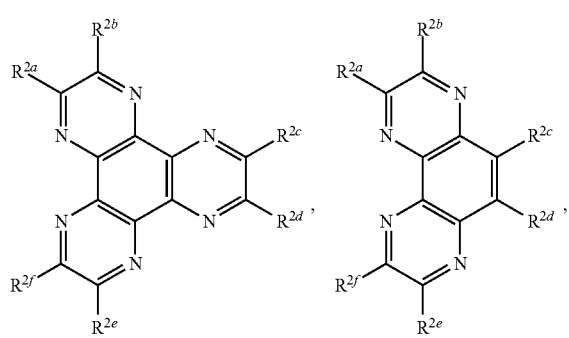
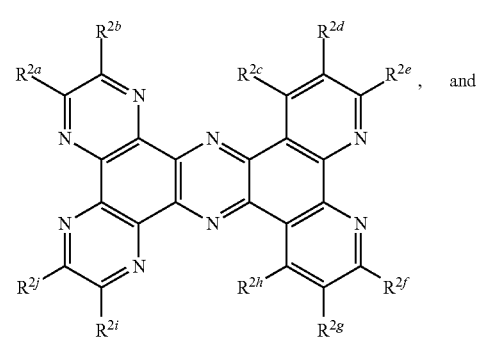
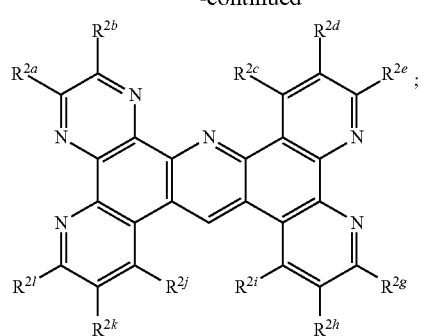
Lig$^2$ is a bidentate ligand that at each occurrence is each independently selected from the group consisting of
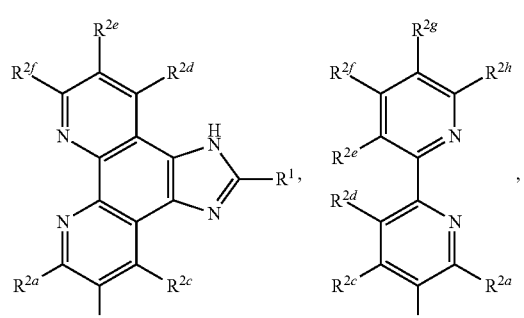
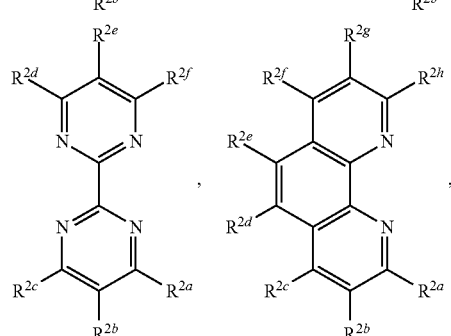
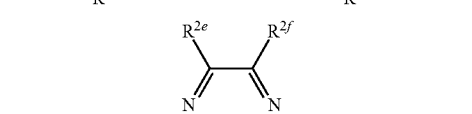
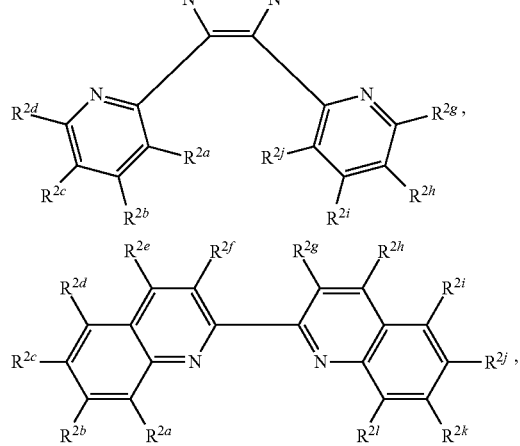

-continued
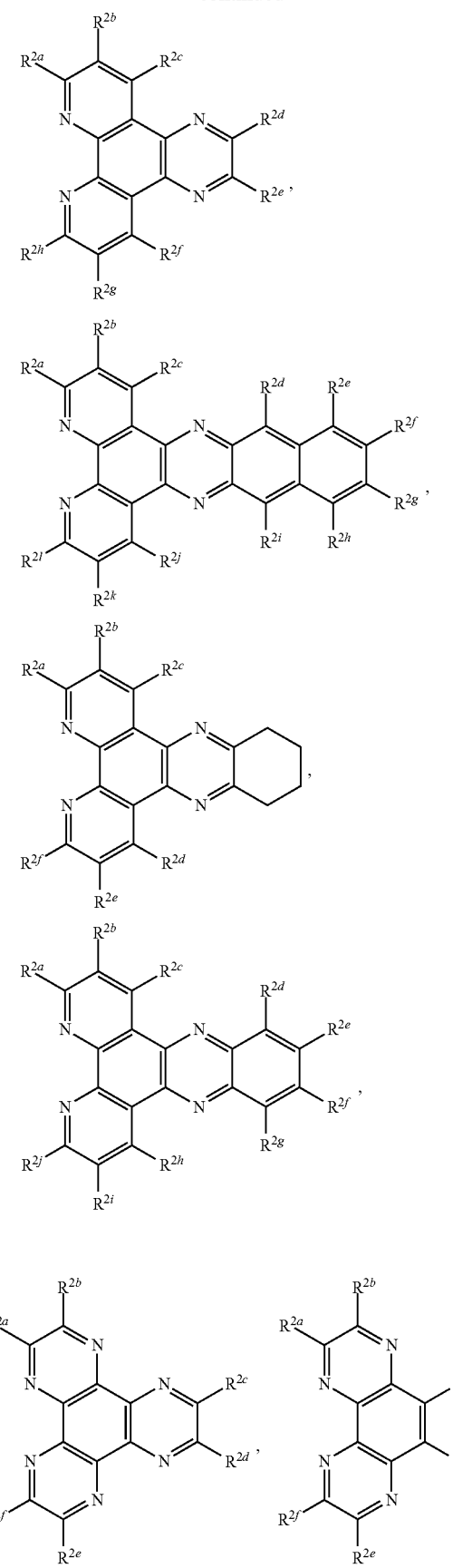
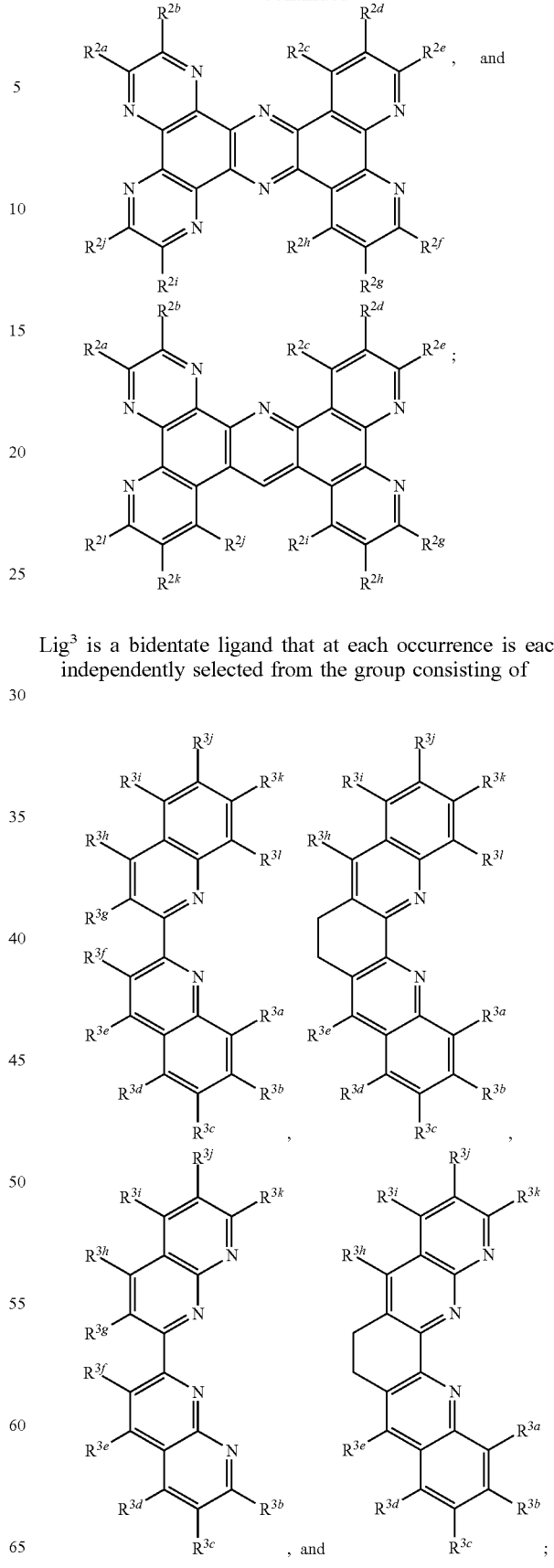
Lig³ is a bidentate ligand that at each occurrence is each independently selected from the group consisting of R[1] is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,

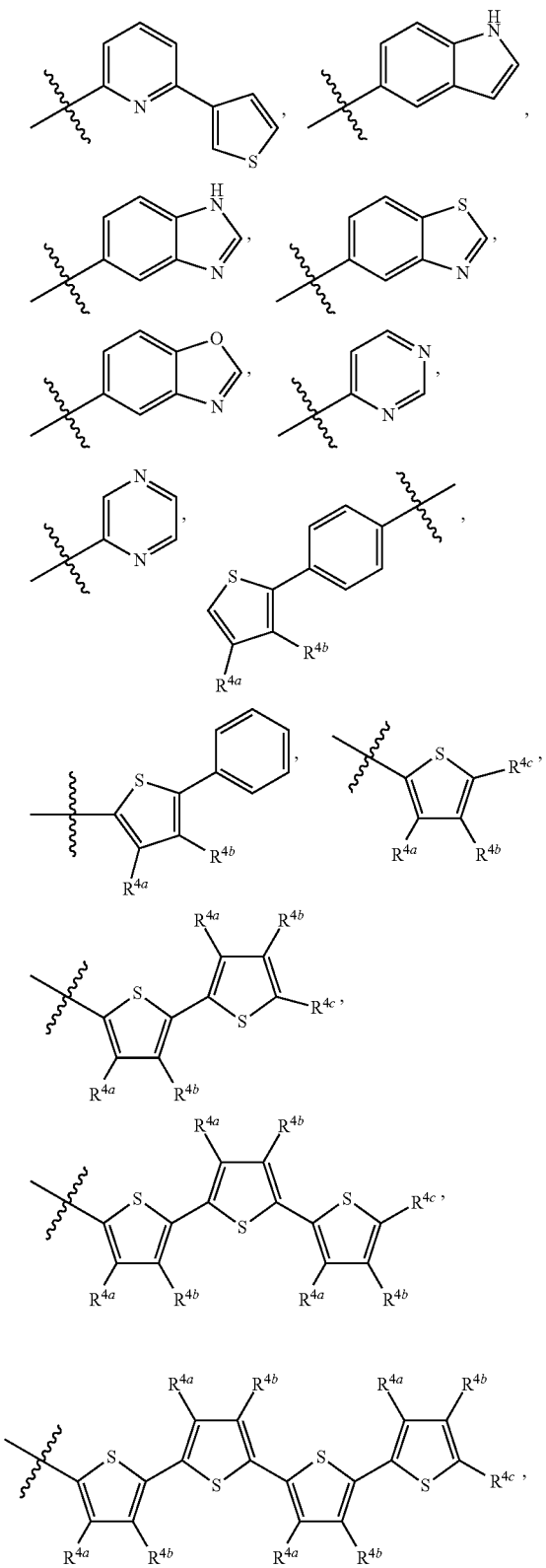

u is an integer;
R[2a], R[2b], R[2c], R[2d], R[2e], R[2f], R[2g], R[2h], R[2i], R[2j], R[2k], and R[2l] at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6{}_2$, $NR^7{}_2$, $SO_3H$, sulfate, sulfonate, optionally substituted aryl, optionally substituted aryloxy, optionally substituted heteroaryl, and optionally substituted heterocycle;
R[3a], R[3b], R[3c], R[3d], R[3e], R[3f], R[3g], R[3h], R[3i], R[3j], R[3k], and R[3l] at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;
R[4a], R[4b], and R[4c] at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence are each independently selected from the group consisting of hydrogen and optionally substituted alkyl;

$R^6$ at each occurrence are each independently selected from the group consisting of hydrogen and optionally substituted alkyl;

$R^7$ at each occurrence are each independently selected from the group consisting of hydrogen and optionally substituted alkyl; and $R^8$ at each occurrence are each independently selected from the group consisting of hydrogen and optionally substituted alkyl.

In certain embodiments, the glycoprotein is transferrin and the chemotherapeutic compound has the formula (VI):

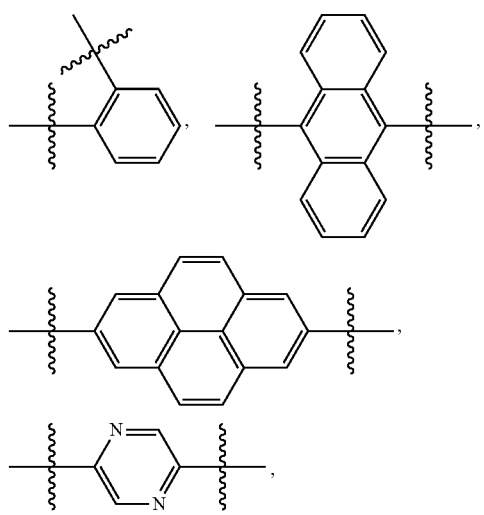

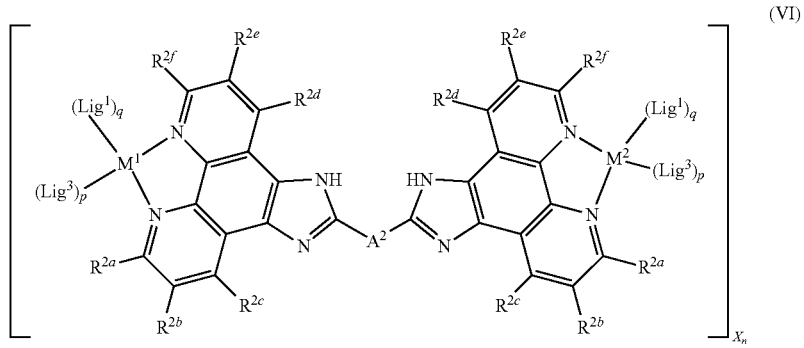

(VI)

including hydrates, solvates, pharmaceutically acceptable salts, prodrugs and complexes thereof wherein;

$M^1$ and $M^2$ at each occurrence is independently a transition metal, and is preferably independently selected from the group consisting of osmium, manganese, molybdenum, rhenium, ruthenium, iron, cobalt, rhodium, iridium, nickel, platinum, and copper;

$A^2$ is selected from the group consisting of

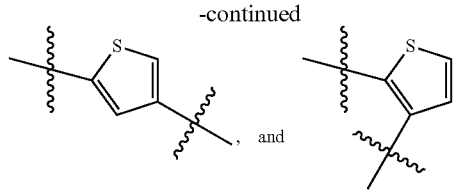

t is an integer.

In certain embodiments, the glycoprotein is transferrin and the chemotherapeutic compound has the formula (VIIa)

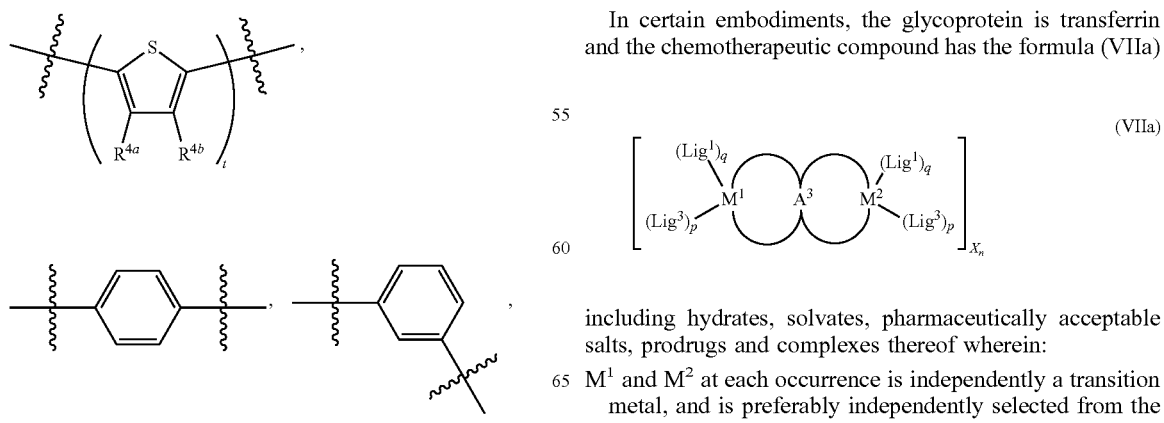

(VIIa)

including hydrates, solvates, pharmaceutically acceptable salts, prodrugs and complexes thereof wherein:

$M^1$ and $M^2$ at each occurrence is independently a transition metal, and is preferably independently selected from the group consisting of osmium, manganese, molybdenum, rhenium, ruthenium, iron, cobalt, rhodium, iridium, nickel, platinum, and copper;

Lig$^1$ is a bidentate ligand that at each occurrence is each independently selected from the group defined above;

Lig$^3$ is a bidentate ligand that at each occurrence is each independently selected from the group defined above;

p is independently at each occurrence 0, 1, or 2;

q is independently at each occurrence 0, 1, or 2;

n is 0, 1, 2, 3, 4, or 5; and

A$^3$ is selected from the group consisting of

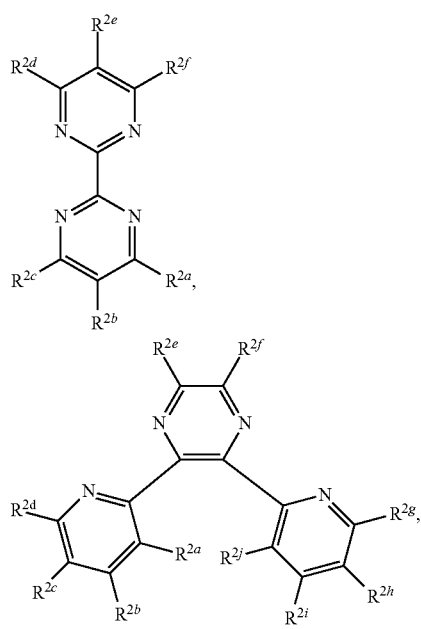

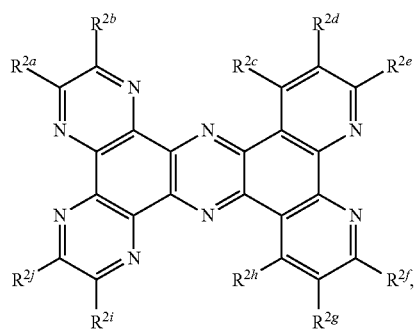

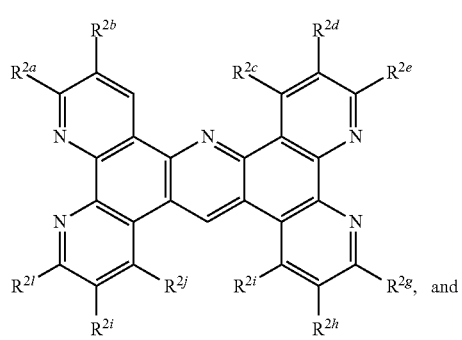

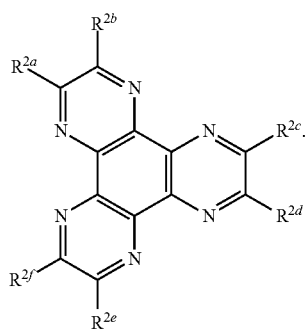

In certain embodiments, the glycoprotein is transferrin and the chemotherapeutic compound has the formula (II)

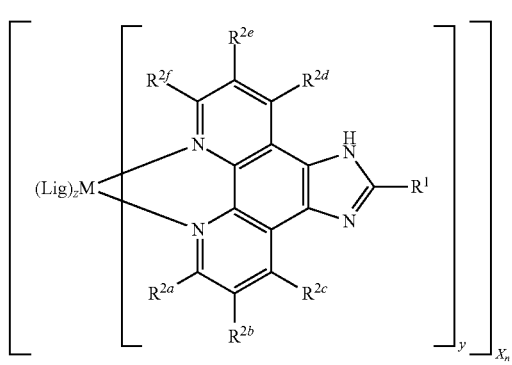

(II)

including hydrates, solvates, pharmaceutically acceptable salts, prodrugs and complexes thereof, wherein:

M is a transition metal preferably selected from the group consisting of manganese, molybdenum, rhenium, iron, ruthenium, osmium, cobalt, rhodium, iridium, nickel, platinum, and copper;

X is selected from the group consisting of Cl$^-$, PF$_6^-$, Br$^-$, BF$_4^-$, ClO$_4^-$, CF$_3$SO$_3^-$, and SO$_4^{-2}$;

n=0, 1, 2, 3, 4, or 5;

y=1, 2, or 3;

z=0, 1, or 2;

Lig at each occurrence is independently selected from the group consisting of

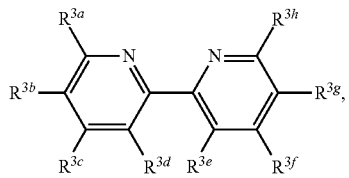

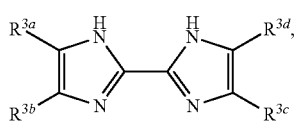

-continued
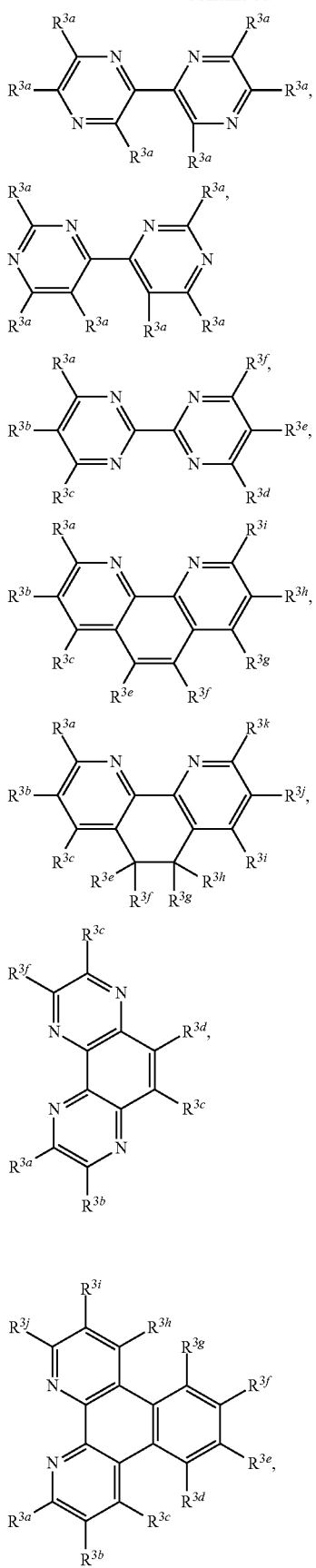
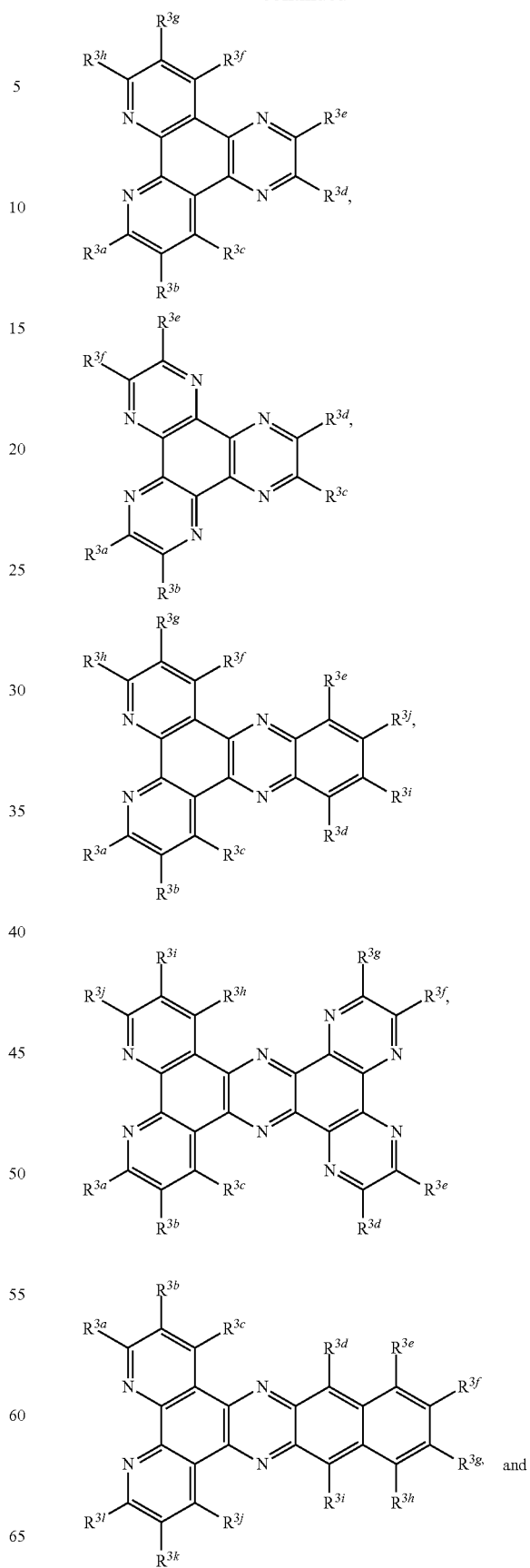
and

-continued

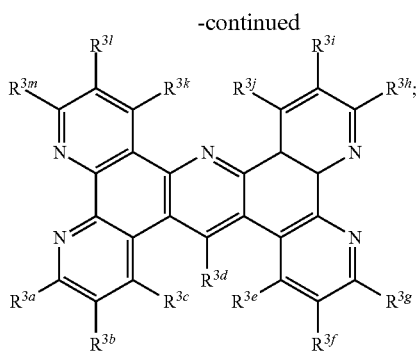

R[1] is selected from the group consisting of

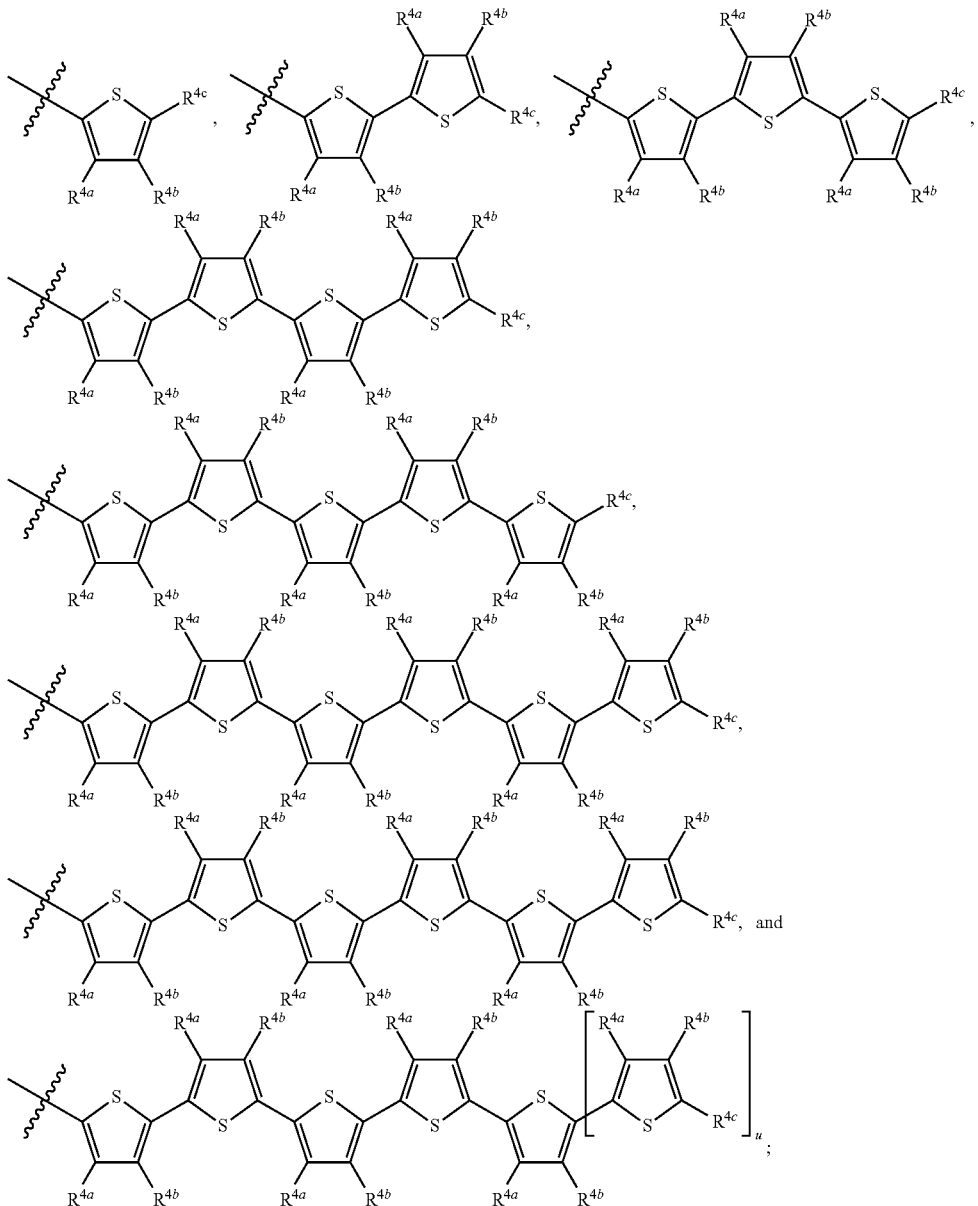

u is an integer;

R[2a], R[2b], R[2c], R[2d], R[2e], and R[2f] at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

R[3a], R[3b], R[3c], R[3d], R[3e], R[3f], R[3g], R[3h] R[3i], R[3j], R[3k], R[3l], and R[3m] at each occurrence are each independently selected from the group consisting of hydrogen, C1-6 optionally substituted alkyl, C1-6 optionally substituted branched alkyl, C1-6 optionally substituted haloalkyl, C1-6 optionally substituted alkoxy, and $CO_2R^8$;

R[4a], R[4b], and R[4c] at each occurrence are each independently selected from the group consisting of hydrogen, C1-6 optionally substituted alkyl, C1-6 optionally substituted branched alkyl, C1-6 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl; and $R^8$ at each occurrence is independently selected from the group consisting of hydrogen and optionally substituted alkyl.

A second aspect of the invention comprises a method for treating a condition associated with hyperproliferating cells, said method comprising administering to a subject having the condition a metal binding glycoprotein and a chemotherapeutic compound containing at least one transition metal, wherein the metal binding glycoprotein and the chemotherapeutic compound containing at least one transition metal are administered in a combined amount effective to treat the condition.

In certain embodiments of the treatment method, the subject is irradiated with light effective to activate the chemotherapeutic compound.

In certain embodiments of the treatment method, the metal-binding glycoprotein is effective to provide at least one of the following advantages relative to treatment by the chemotherapeutic compound without the glycoprotein: (a) increased uptake by cancer cells; (b) increased uptake by tumors; (c) increased efficacy at wavelengths longer than 600 nm; (d) increased efficacy at wavelengths less than or equal to 600 nm; (e) improved absorbance at wavelengths longer than 600 nm; (f) improved absorbance at wavelengths less than or equal to 600 nm; (g) increased production of reactive oxygen species; (h) increased photodynamic therapy effect under non-hypoxic conditions; (i) increased photodynamic therapy effect under hypoxic conditions; (j) increased LD50; (k) increased MTD; (l) increased photostability; and (m) increased shelf-life.

In certain embodiments of the treatment method, the metal-binding glycoprotein and the chemotherapeutic compound containing at least one transition metal are administered in a combination dosage form or are co-administered from two or more independent sources.

In certain embodiments of the treatment method, the metal-binding glycoprotein is transferrin and the chemotherapeutic compound is defined by formula (I), formula (VI), formula (VIIa) or formula (II) above.

In certain embodiments of the treatment method, the at least one transition metal is at least one of Ru, Rh, Os and Ir.

In certain embodiments of the treatment method, the metal-binding glycoprotein is a recombinant human transferrin, such as OPTIFERRIN.

In certain embodiments of the treatment method, the condition treated by the method is at an immune privileged site, the metal binding glycoprotein and the chemotherapeutic compound containing at least one transition metal are systemically administered in a form of a complex, and the complex crosses at least one of the blood-brain barrier, the retina blood barrier and the blood-cerebrospinal fluid barrier to accumulate at the immune privileged site. Preferably, the metal-binding glycoprotein is transferrin and the chemotherapeutic compound is defined by formula (I), formula (VI), formula (VIIa) or formula (II) above.

In certain embodiments of the treatment method, the complex crosses the blood-brain barrier and preferentially accumulates in a brain tumor being treated by the method.

In certain embodiments, the subject is irradiated with ionizing radiation effective to activate the chemotherapeutic compound.

In certain embodiments of the treatment method, the metal binding glycoprotein and the chemotherapeutic compound containing at least one transition metal are administered in a form of a complex, the chemotherapeutic compound is a photodynamic compound, and the complex further comprises at least one active pharmaceutical ingredient (API). In some of these embodiments, the API is an anti-neoplastic agent free of any transitional metals and/or the complex crosses at least one of the blood-brain barrier, the retina blood barrier and the blood-cerebrospinal fluid barrier to accumulate at an immune privileged site.

A third aspect of the invention comprises a method for destroying a microbial cell, said method comprising: contacting the microbial cell with an effective amount of the composition according to the invention; and irradiating the microbial cell with light effective to activate the composition so as to destroy the microbial cell.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

BRIEF DESCRIPTION OF SEVERAL VIEWS OF THE DRAWINGS

The invention will be described in conjunction with the following drawings in which like reference numerals designate like elements and wherein:

FIGS. 8A, 8B and 8C show graphs of absorbance ratio against incident photons.

FIGS. 9A, 9B and 9C show graphs of absorbance ratio against incident photons.

FIGS. 18A, 18B, 18C and 18D show graphs of cell kill with and without transferrin.

FIGS. 36A, 36B, 36C, 36D, 36E, 36F, 36G, 36H, 36I and 36J are MRIs of the brain of another rat treated in accordance with another embodiment of the invention.

FIGS. 37, 38 and 39 show inductively coupled plasma mass spectrometry (ICP-MS) data.

DETAILED DESCRIPTION OF PREFERRED EMBODIMENTS OF THE INVENTION

Glossary

Figure 1A:
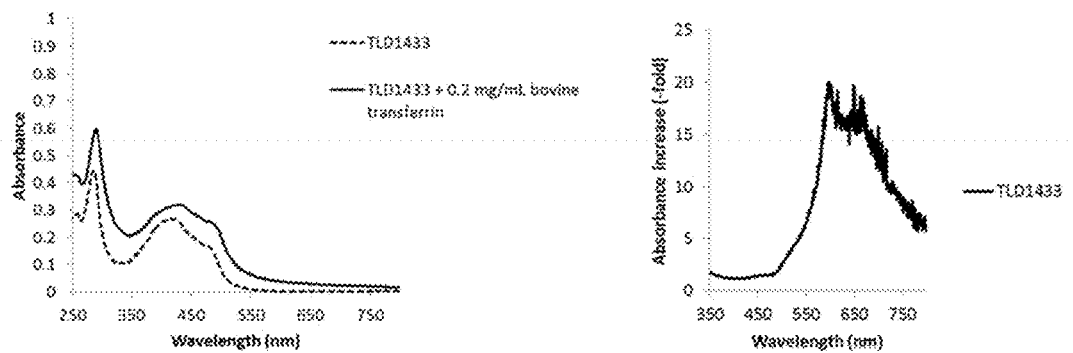
FIGS. 1A, 1B and 1C show graphs of absorbance/absorbance increase against wavelength.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously For the purposes of the present invention the terms "compound," "analog," and "composition of matter" stand equally well for the inventive compounds described herein, be they photodynamic or not, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, naphthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^6)_2$, each $R^6$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

As used herein, the term "photodynamic therapy" refers to a treatment for destroying cells or modulating immune function, including immune response, of cells and tissue through use of a drug that can be activated by light of a certain wavelength and dose.

As used herein the term "chemotherapeutic compound" refers to a chemical compound with prophylactic, ameliorative and/or curative properties with respect to one or more conditions or diseases.

As used herein, the term "photodynamic compound" refers to a compound that provides photodynamic therapy. Photodynamic compounds are a subset of chemotherapeutic compounds as defined herein.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

As used herein, the term "biological target" refers to an organ, tissue and/or cell of an organism and/or to the organism itself.

Advantages of the Invention

The invention is based in part on the unexpected discovery that Ru, Rh and Os based PDCs, particularly those disclosed in WO 2013158550 A1, WO 2014145428 A2, U.S. Pat. Nos. 6,962,910, 7,612,057, 8,445,475, 8,148,360 and US 20160206653 A1, when administered systemically in combination with metal-binding glycoproteins, can reach immune privileged sites by penetrating the blood-brain barrier, the retina-blood barrier and the blood-cerebrospinal fluid barrier.

The invention is also based on the additional unexpected discovery that the administration of such PDC-glycoprotein combinations leads to preferential and persistent accumulation of the PDCs in malignant cells and tissues.

The brain and eye are immune privileged sites protected by the blood brain barrier and blood retina barrier. Most biomolecules cross the blood-brain barrier by transmembrane diffusion whereby a low molecular weight and high lipid solubility are favored. Other drugs or photosensitizer can cross the blood-brain barrier by the use of saturable transport systems.

Ruthenium and osmium are in the same group of the periodic table of elements as Iron, Group 8, and share many of its characteristics. Rhodium is in neighboring Group 9. As Ruthenium and Osmium are in the same group as Iron, they share many characteristics. For example, electronically, Ru (II) and OS (II) molecules readily bond with nitrogen and sulphur donor (this mechanisms is also relevant for induction of NO (Chatterjee D, Shome S, Jaiswal N, Banerjee P. Nitrite reduction mediated by the complex Ru III (EDTA). Dalton Trans. 2014 Sep. 28; 43(36):13596-600) and may play a role in switching the Type II to Type I photochemistry) molecules that are abundantly found in many proteins within the body. For this reason transition metal complexes are able to take advantage of the body's ability to efficiently transport and uptake of iron (Antonarakis E S, Emadi A. Ruthenium-based chemotherapeutics: are they ready for prime time? Cancer Chemother Pharmacol. 2010 May; 66(1):1-9). The PSs are transported inside cancer cell (mitochondria) by binding to endogenous transferrin (a glycoprotein mainly produced in the liver) via transferrin receptor (TfR); Bergamo A, Sava G. Ruthenium anticancer compounds: myths and realities of the emerging metal-based drugs. Dalton Trans. 2011 Aug. 21; 40(31):7817-23.

Rapidly dividing tumor cells have an increased demand for iron and the levels of TfRs found on these cancerous cells are greatly increased. The receptor increase on cancerous cells has been document as two to twelve times that of healthy cells (Antonarakis E S, Emadi A. Ruthenium-based chemotherapeutics: are they ready for prime time? Cancer Chemother Pharmacol. 2010 May; 66(1):1-9). This greatly increases the selectivity of the PSs as the majority of the dose is sequestered in cancerous tissues, bypassing most healthy cells. This effect contributes to the lower toxicity that is associated to the ruthenium drugs in comparison to platinum (Bruijnincx, Pieter C. A.; Sadler, Peter J. (2009). "Controlling platinum, ruthenium, and osmium reactivity for anticancer drug design". Advances in Inorganic Chemistry 61. p. 1).

Because iron is required for growth of cancer cells, we see an additional benefit of competitive binding of PDCs to the transferrin receptor on a tumor cell. In addition to the active uptake of PDCs, the use of this mechanism in inhibiting both cell proliferation and HIF-1α. Angiogenesis under normoxic and hypoxic conditions may be of additional therapeutic use. Moreover, as cancer cells are generally growing and multiplying much more rapidly than normal healthy cells, this creates an environment that is less oxygen rich due to the raised metabolic rate. When this is paired with the tendency of cancerous cells to contain higher levels of glutathione and a lower pH, a chemically reducing environment is created. Indeed, our data have shown an additive and even potentially synergistic role of glutathione in the mechanisms of cancer cells kill by PDCs. The glutathione-mediated reduction is thought to occur by mitochondrial proteins or microsomal single electron transfer proteins, though it may also occur by trans-membrane electron transport systems which reside outside the cell, implying that, due to local administrations of PSs, the PS is still effective even if some quantity of the PS may leak/escape into intracellular space. In theory, it is also possible for the Ruthenium compounds to be oxidized back to their inactive form if they leave the cancerous environment and, hence, in addition to a very strong photostability of PSs, this phenomenon may also contribute to additional treatment efficacy and safety.

During light activation in preferred embodiments of the invention, in addition to PDT-induced inflammation, there is modification of tumor cell death and antigen presenting cells ("APC") activation via the danger-associated molecular patterns ("DAMPs"). The recognition of molecules released or expressed by dead, dying, injured, or stressed "antigenic"-apoptotic cells can elicit potent and tumor-specific immune responses. PDT-induced DAMPs emitted by dying cancer cells can elicit cancer antigen-directed anti-tumor short-term effects (6 to 8 weeks) and a long-term anti-tumor effect (>10 months) immunity. DAMP's stimulate immune responses through dialogue with T lymphocytes ("Th") cells, Natural Killer ("NK") cells and APSs. Certain APSs, such as dendritic cells and macrophages are stimulated and actively trafficked during PDT-induced "immunologic" cell death ("ICD") by danger signalling pathways, which are instigated and regulated by a complex interplay between cellular stress signaling, reactive oxygen species ("ROS") production and certain metabolic/biosynthetic processes (i.e., autophagy, caspase activity and secretory pathway: calreticulin, Adenosine Tri-Phosphate ("ATP"), Heat Shock Proteins, High Mobility Group Box 1, cytokines, etc).

Methods of the Invention

Methods of the invention comprise the use of metal-binding glycoproteins as delivery vehicles for metal-based chemotherapeutic agents (preferably, PDCs) so as to facilitate delivery of the PDCs into a biological target. The methods are intended to provide enhanced safety and/or efficacy relative to the delivery of metal-based PDCs without the addition of exogenous metal-binding glycoproteins. PDCs delivered via the inventive methods and compositions enjoy enhanced biophysical, biochemical and biomedical properties, such as the efficacy, tolerability, therapeutic efficacy and diagnostic properties of the PDCs in multi-wavelength photodynamic therapy in normoxic and hypoxic conditions.

Hence, methods of the invention comprise combining metal-containing PDCs with metal-binding glycoproteins and administering the combination to a patient in need of PDT at an immune privileged site.

The PDC and glycoprotein are preferably administered as a complex within a pharmaceutically acceptable dosage form. The dosage form can further comprise diluents, extenders, carriers and the like. The dosage form is preferably a liquid, solid, gel or combination thereof. Suitable dosage forms include but are not limited to pills, tablets, capsules, eye drops and injectable liquids. The dosage form can be administered orally, rectally, topically, parenterally or intravenously. Administration can be systemic or localized (e.g., by injection into a tumor).

The PDC is preferably photoactive so as to generate reactive oxygen species. Photoactivation can be achieved by the application of light from a light source. Suitable light sources include but are not limited to lasers, light emitting diodes, fiber optics and lamps. The light source can be external to the patient's body with the light be applied transdermally. Alternatively, the light source can be placed within the patient's body briefly (e.g, through an endoscope or fiber optic catheter) or over an extended duration (e.g., as an implant).

In certain embodiments, the PDC can be activated by ionizing radiation in accordance with the teachings of U.S. Application 62/325,226, filed Apr. 20, 2016. The ionizing radiation is preferably at least one of X-rays and Gamma rays, and is preferably applied to treat targets at immune privileged sites.

PDT dose parameters can be determined by a person of ordinary skill in the art with an understanding of the dosimetric and biological factors that govern therapeutic variability. See, e.g., Rizvi et al. "PDT Dose Parameters Impact Tumoricidal Durability and Cell Death Pathways in a 3D Ovarian Cancer Model." Photochemistry and photobiology. 2013; 89(4):942-952.

Factors to be considered include but are not limited to the amount of the PDC at the target site, tissue oxygenation, the molar extinction coefficient of the PDC at a chosen wavelength of light to produce a maximum level of reactive oxygen species, target (e.g. tumor) localization, size, shape, vascular structure, etc. The following table lists PDT parameters to be adjusted and provides preferred, non-exhaustive, values for said parameters.

| PDT Parameter | Value |
| --- | --- |
| Wavelength (nm) | 200-1000 or 400-950 or 500-950 |
| Fluence (J/cm$^2$) | 0.01 to 100,000 or 1 to 10,000 or 10 to 1,000 |
| Irradiance (mW/cm$^2$) | 10 to 10,000 or 50 to 5,000 or 100 to 1,000 |
| Irradiation Time (secs) | 1 to 10,000 or 10 to 5,000 or 100 to 1,000 |
| PDC Concentration (mg/kg body wt.) | 0.01 to 6000 or 0.1 to 5000 or 1 to 2500 or 10 to 1000 or 50 to 500 |

In certain embodiments, the glycoprotein complex including the metal-containing PDC can be used as a carrier to transport other active pharmaceutical ingredients (APIs) to target tissues, such as immune privileged sites. Suitable APIs are not particularly limited, but most preferred are anti-neoplastic agents. The API need not contain a transition metal and need not be a PDC. Preferably, the PDC is a chemotherapeutic compound and the API is an anti-neoplastic agent different from the PDC.

For example, temozolomide attached via a linker to the glycoprotein-PDC complex could be administered to a cancer patient. The half-life of temozolomide is approximately 1.8 hours. The half-life of the PDC can differ from the API so that treatment is effective over an extended period of time. The glycoprotein-PDC complex with the API will be preferentially taken-up by the target tumor and cause less toxicity to the benign tissue. The effects of the API can optionally be followed by PDT.

The present invention further relates to a method for preparing the compounds of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and coordination complexes and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic and inorganic synthesis will recognize that the nature and order of the synthetic steps presented can be varied for the purpose of optimizing the formation of the compounds described herein.

The preparation methods described herein can be monitored according to any suitable method known in the art. For example, product formation can be monitored by spectroscopic means, such as nuclear magnetic resonance spectroscopy (e.g., 1H or 13C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Metal-binding glycoproteins suitable for use in the invention are capable of binding transition metals and delivering to a biological target said metals and other materials complexed with said metals. The metal-binding glycoproteins are preferably capable of binding Group 8 metals and/or Group 9 metals, and most preferably Ru, Os, Rh and Ir. Most preferred are the iron-binding glycoproteins transferrin, lactoferrin, ovotransferrin and melanotransferrin and variants thereof, with transferrin being most preferred. The glycoprotein can be purified from natural sources or can be from artificial sources. Thus, for example, the glycoprotein in certain embodiments is a recombinant transferrin, such as Apo-Transferrin or OPTIFERRIN, a recombinant human transferrin available from InVitria, a division of Ventria Bioscience. See US 20120088729 A1, Zhang et al., "Expression, purification, and characterization of recombinant human transferrin from rice (*Oryza sativa* L.)." Protein Expr Purif. 2010 November; 74(1):69-79. Epub 2010 May 4, and Steere et al., "Biochemical and structural characterization of recombinant human serum transferrin from rice (*Oryza sativa* L.)." J Inorg Biochem. 2012 Jul. 11; 116C:37-44. OPTIFERRIN is a particularly preferred glycorprotein as it increases the targeting and reduces the photobleaching of the metal-glycoprotein complexes of the invention.

Biological targets of the invention are organisms, organs, tissues and/or cells amenable to treatment with, and/or detection by, the metal-glycoprotein complexes of the invention. The targets are preferably hyperproliferating cells, such as cancer and non-malignant lesions. Most preferably, the targets are immune privileged. The invention enables the treatment of targets across the blood-brain, blood-retina and blood-cerebrospinal fluid barriers.

Tf solution pre-mixed with PS solution (Ruthenium, Ruthenium-Rhodium and Osmium-based PSs) demonstrates evidence of metal-specific binding of the PS to Tf. The resulting complex has increased absorbance/molar extinction coefficient at long wavelengths (>600 nm), increased ROS production (generation of hydroxyl radical is potentiated to a much greater extent than that of singlet oxygen suggesting a switch to Type I photoreaction in the presence of transferrin), increased and preferential uptake by cancer cells, increased efficacy of in vitro PDT accompanied by a decrease in dark toxicity and consequently by increased therapeutic ratio, increased and selective uptake by cancer cells and tumor tissues and increased efficacy of in vivo PDT in visible and NIR light. In certain embodiments, increased absorbance/molar extinction coefficient at wavelengths at or below 600 nm are achieved, which embodiments are particularly suitable for excitation with green, blue, UV and X-ray radiation.

Ruthenium, Ruthenium-Rhodium and Osmium-based photosensitizers bind to transferrin demonstrating characteristic binding signatures.

Binding to transferrin changes chemical, physical and biomedical characteristics of metal-based molecules and/or formulations, and induces absorption by Ruthenium, Ruthenium-Rhodium and Osmium-based photosensitizers in red and NIR wavelengths where their absorption without transferrin is negligible.

Irradiation-induced fluorescence of Ruthenium, Ruthenium-Rhodium and Osmium-based photosensitizers is increased in the presence of transferrin, which may play a role in using metal-transferrin complexes in diagnostics.

Binding of Ruthenium, Ruthenium-Rhodium and Osmium-based photosensitizers to transferrin will increase their resistance to photobleaching.

Binding of Ruthenium, Ruthenium-Rhodium and Osmium-based photosensitizers to transferrin will increase production of reactive oxygen species in a cell free environment. This effect will increase with the increase of transferrin concentration. Increased production of hydroxyl radical suggests that the photosensitizers' photoeffect is switched from Type II to Type I, which is essential for PDT treatment of bulky hypoxic tumors.

Binding of Ruthenium, Ruthenium-Rhodium and Osmium-based photosensitizers to transferrin will increase their preferential uptake by cancer cells.

In the presence of additional transferrin, Ruthenium, Ruthenium-Rhodium and Osmium-based photosensitizers will demonstrate lesser dark toxicity in vitro (using cancer cell lines); PDT efficacy will increase. This will result in the increase in therapeutic ratios of the photosensitizers.

Binding of Ruthenium, Ruthenium-Rhodium and Osmium-based photosensitizers to additional transferrin will demonstrate PDT efficacy in hypoxic conditions absent without transferrin.

Blocking transferrin receptors with specific antibodies will eliminate facilitating effect of transferrin on PDT effect.

Incubation of Ruthenium, Ruthenium-Rhodium and Osmium-based photosensitizers with transferrin prior to i.p. injection in vivo will increases MTD50 indicating a decrease in the PSs toxicity.

Incubation of Ruthenium, Ruthenium-Rhodium and Osmium-based photosensitizers with transferrin prior to IP injection will increase in vivo PDT efficacy in NIR (808 nm) and red (625 nm).

The invention will enable:
Selective delivery of Ruthenium, Ruthenium-Rhodium and Osmium-based photosensitizers to immune privileged targets;
Increase in efficacy of the PS, especially in wavelength ranges where the photosensitizers are otherwise ineffective (red, NIR);
PDT efficacy in hypoxia when the PSs are not effective without Tf;
Improved safety, tolerability and efficacy of all metal-based medicinal formulations that could be linked to Tf and/or Tf-based substances, including beads and or liposomes; and
Improved diagnostic properties of metal based molecules.

The invention further encompasses the use of metal-glycoprotein complexes of the invention to enhance uptake by cells of metal-based pharmaceutical agents that are not light activated (e.g., RAPTA, NAMI, KP1019, RM-175).

Compositions of the Invention

The compositions of the invention comprise a metal-binding glycoprotein and a chemotherapeutic compound (e.g., a photodynamic compound) containing at least one transition metal, which is preferably a Group 8 or 9 metal and is most preferably at least one of Ru, Rh and Os.

The chemotherapeutic compound is preferably at least one such compound disclosed in WO 2013158550 A1, WO 2014145428 A2, U.S. Pat. Nos. 6,962,910, 7,612,057, 8,445, 475, 8,148,360 or US 20160206653 A1. Other chemotherapeutic compounds suitable for use in the invention include but are not limited to RAPTA, NAMI, KP1019 and analogs thereof.

In certain embodiments, compositions of the invention comprise transitional metal-based combinations that are optionally surrounded (directly and/or indirectly binded) by various ligands, such as in coordination compounds. In some of these embodiments, bridging ligands are included, which are highly electron donating to the metal(s).

In all of the embodiments provided herein, examples of suitable optional substituents are not intended to limit the scope of the claimed invention. The compounds of the invention may contain any of the substituents, or combinations of substituents, provided herein.

The compositions of the invention are useful for the treatment and diagnosis of disease states, particularly for the destruction of infectious organisms, hyperproliferating cells, and tumor cells. The compositions preferably included PDCs which (i) are metal-based coordination complexes, (ii) absorb ultraviolet (UV), visible, and infrared (IR) (particularly, near infrared (NIR)) light and are activated by wavelengths from UV to IR, particularly >800 nm, (iii) kill human cancer cells in culture and in animals, and (iv) destroy bacteria and antibiotic-resistant bacteria.

Compositions of the invention are also capable of destroying microorganisms, such as *Staphylococcus aureus* (SA) and methicillin-resistant *S. aureus* (MRSA), with activation by UV to IR light, particularly red and NIR light.

The invention will be illustrated in more detail with reference to the following Examples, but it should be understood that the present invention is not deemed to be limited thereto.

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

EXAMPLES

Example 1

Figure 1B:
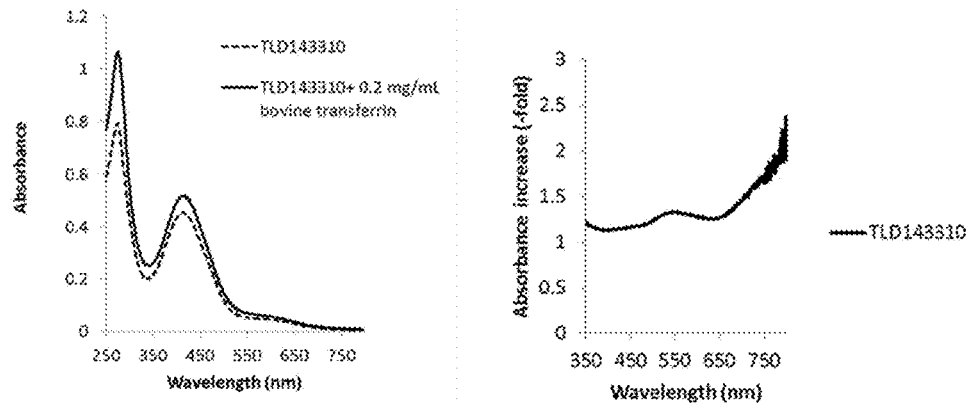
Figure 1C:
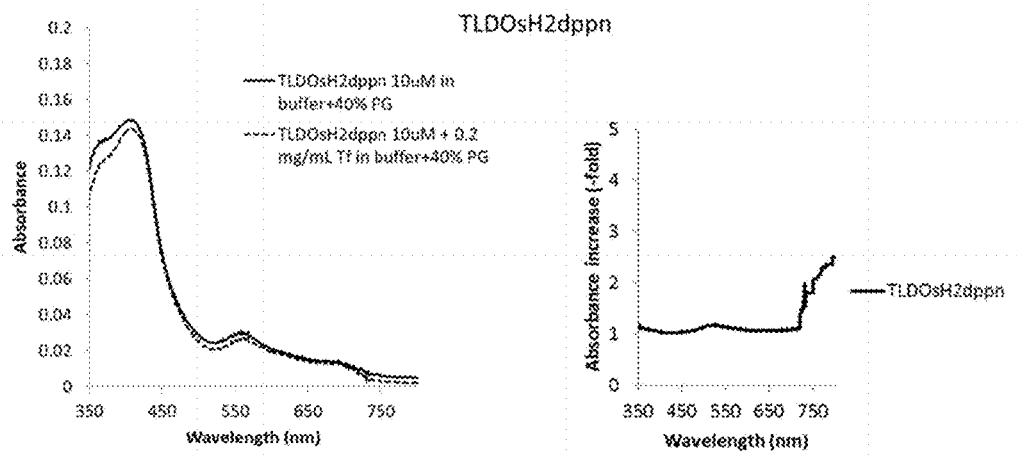

Transferrin (0.2 mg/mL) was incubated with different photosensitizers (10 uM) and the absorbance spectra were obtained. FIG. 1A shows an increase in absorption by Ruthenium (TLD1433). FIG. 1B shows Ruthenium-Rhodium (TLD143310) based PSs and FIG. 1C shows Osmium (TLDOsH2dppn) based PSs in the presence of transferrin. For each photosensitizer, the left plot shows the absolute difference in absorbance with transferrin vs. without transferrin. The right plot shows relative increase in absorbance with transferrin vs. without transferrin. Note that a large relative increase in absorbance may be accompanied by a small absolute difference and vice versa.

The binding of the photosensitizers to transferrin was accompanied by an increased absorption in visible and NIR range, especially at longer wavelengths. It is noteworthy that negligible absorption of the photosensitizers in red & NIR range became substantial upon binding of these photosensitizers to transferrin.

Example 2

Binding Signatures

Figure 2A:
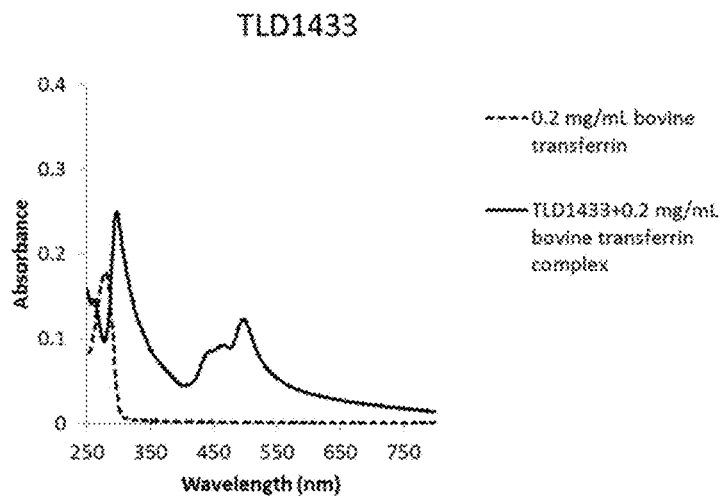
FIGS. 2A, 2B and 2C show graphs of absorbance against wavelength.
Figure 2B:
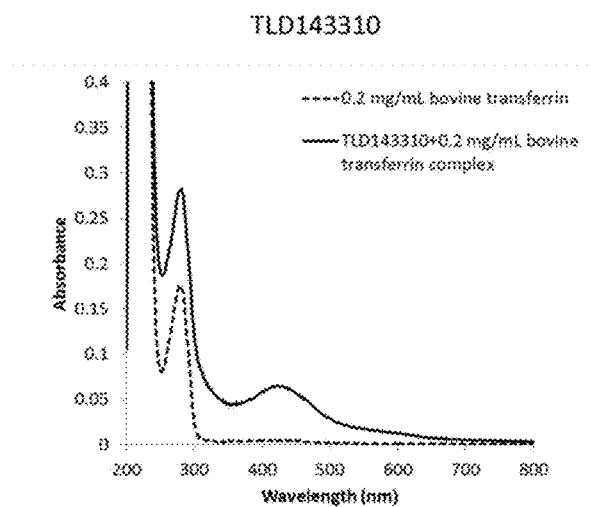
Figure 2C:
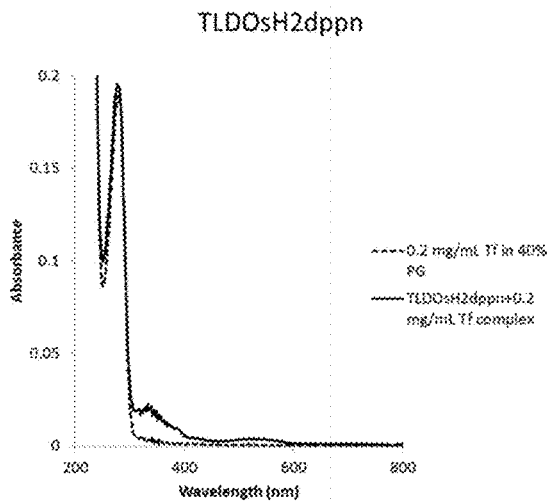

Transferrin (0.2 mg/mL) was incubated with the photosensitizers (10 uM) and absorption spectra were obtained. FIGS. 2A, 2B and 2C show transferrin binding to Ruthenium (TLD1433, FIG. 2A), Ruthenium-Rhodium (TLD143310, FIG. 2B) and Osmium (TLDOsH2dppn, FIG. 2C) based photosensitizers.

Binding of Ruthenium and Ruthenium-Rhodium-based photosensitizers to transferrin is characterized by a characteristic signature: an increased peak of absorption at 280 nm and a new peak in 400-500 nm range. Osmium-based photosensitizers demonstrate different binding signature: new peaks in 300-400 nm and 500-600 nm ranges.

Example 3

Fluorescence

Fluorescence of TLD1433 (10 uM) was measured quartz cuvettes without Tf (in water) and in the presence of 0.2 mg/mL Tf (in phosphate buffer+100 mM NaCl, pH=7.0). Fluorescence was measured at different excitation wavelengths (380, 400, 450, 470, 500 nm).

Figure 3A:
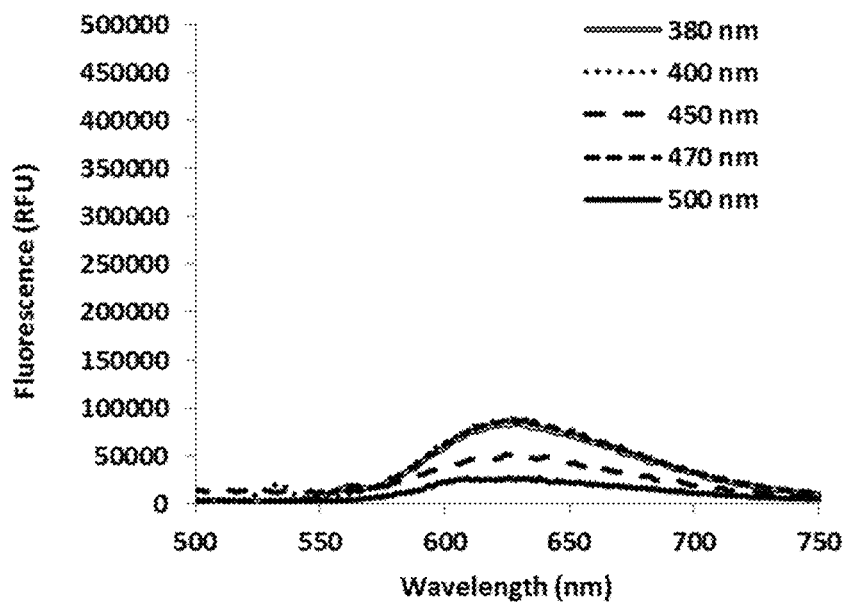
FIGS. 3A and 3B show graphs of fluorescence against wavelength.
Figure 3B:
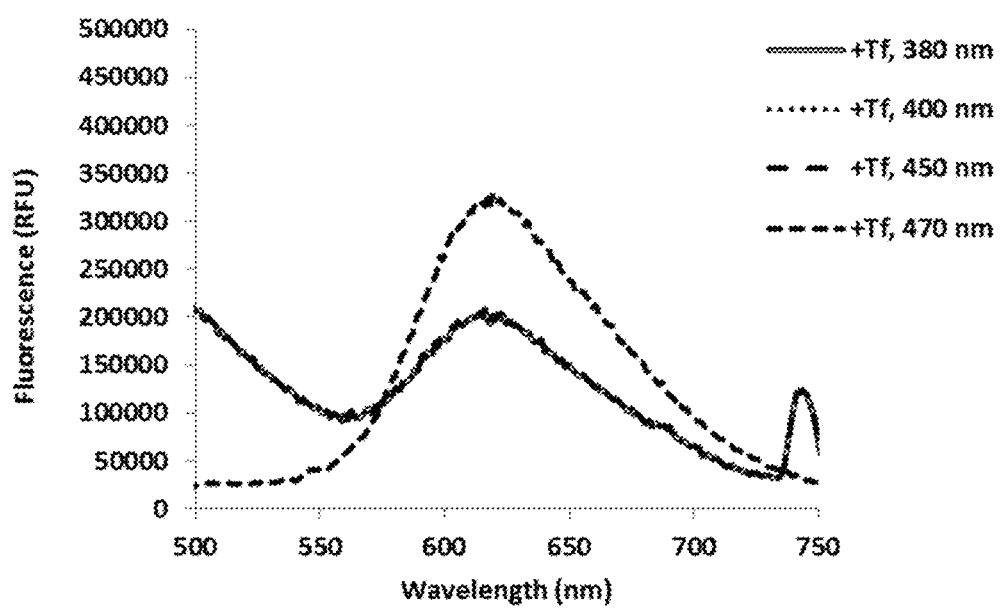

TLD1433 demonstrates measurable fluorescence that is intensified in the presence of transferrin. With no transferrin (FIG. 3A), maximal fluorescence was evoked at excitation wavelengths 380, 400 and 470 nm (emission maximum 624 nm). In the presence of transferrin (FIG. 3B), fluorescence was strongly increased, especially at 470 nm excitation, with emission maximum slightly shifted towards shorter wavelengths (619 nm).

Detectable fluorescence of TLD1433 makes it useful for diagnostic purposes (detection of selective uptake of TLD1433, preferably by cancerous tissues).

Example 4 (Prophetic)

Figure 4A:
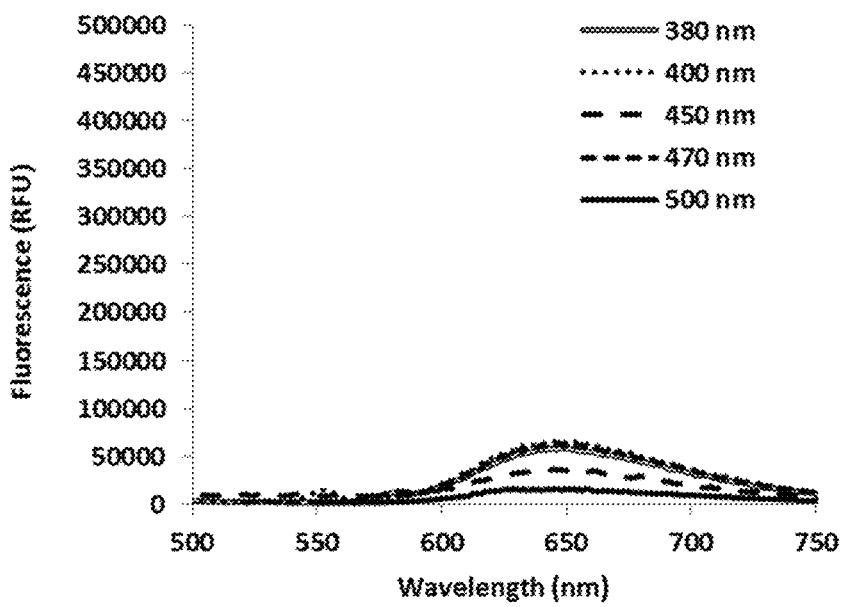
FIGS. 4A and 4B show graphs of fluorescence against wavelength.
Figure 4B:
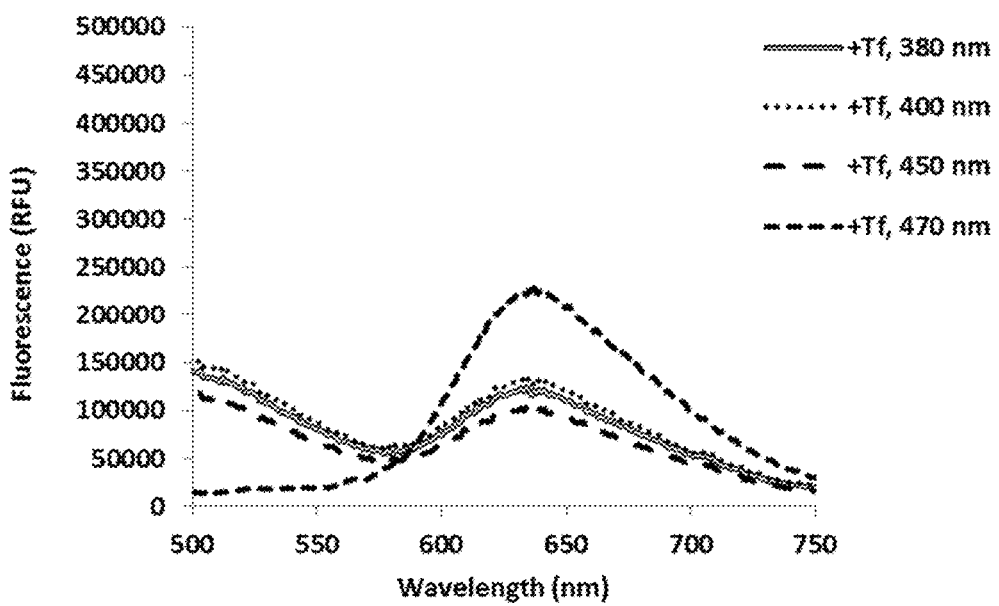

FIGS. 4A and 4B

Fluorescence of TLD1433 (10 uM) was measured quartz cuvettes without Tf (in water) and in the presence of 0.2 mg/mL Tf (in phosphate buffer+100 mM NaCl, pH=7.0). Fluorescence was measured at different excitation wavelengths (380, 400, 450, 470, 500 nm).

TLD143310 demonstrates measurable fluorescence that is intensified in the presence of transferrin. With no transferrin (FIG. 4A), maximal fluorescence was evoked at excitation wavelengths 380, 400, 470 nm (emission maximum 650 nm). In the presence of transferrin (FIG. 4B), fluorescence was strongly increased, especially at 470 nm excitation, with emission maximum slightly shifted towards shorter wavelengths (637 nm). Detectable fluorescence of TLD143310 makes it useful for diagnostic purposes (detection of selective uptake of TLD143310, preferably by cancerous tissues).

Example 5 (Prophetic)

Fluorescence of TLDOsH2dppn (10 uM) was measured quartz cuvettes without Tf (in water) and in the presence of 0.2 mg/mL Tf (in phosphate buffer+100 mM NaCl, pH=7.0). Fluorescence was measured at different excitation wavelengths (380, 400, 450, 470, 500 nm).

Figure 5A:
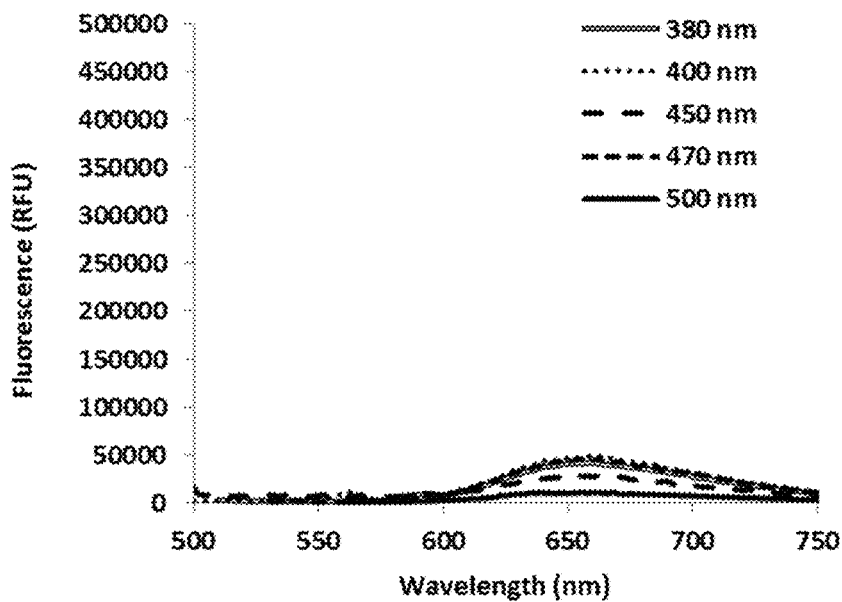
FIGS. 5A and 5B show graphs of fluorescence against wavelength.
Figure 5B:
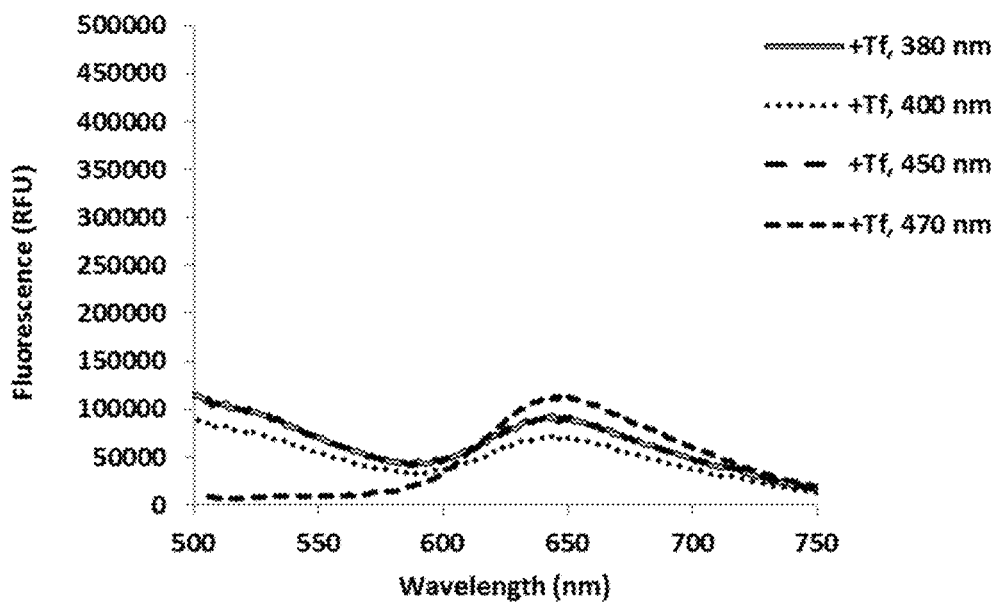

TLDOsH2dppn demonstrates measurable fluorescence that is intensified in the presence of transferrin. With no transferrin (FIG. 5A), maximal fluorescence was evoked at excitation wavelengths 380, 400, 470 nm (emission maximum 660 nm). In the presence of transferrin (FIG. 5B), fluorescence was strongly increased, especially at 470 nm excitation, with emission maximum slightly shifted towards shorter wavelengths (650 nm).

Detectable fluorescence of TLDOsH2dppn makes it useful for diagnostic purposes (detection of selective uptake of TLDOsH2dppn, preferably by cancerous tissues).

Example 6

Photobleaching

Photobleaching was measured: (a) at wavelength in visible range maximal for each photosensitizer. This allows to estimate dynamics of amount of unbleached photosensitizer during irradiation; and (b) at 530, 635 and 808 nm. This allows estimating dynamics of unbleached photosensitizer available to exert PDT effect at these wavelengths as practically useful for PDT treatments.

Photosensitizers (10 uM) were dissolved in phosphate buffer+100 mM NaCl (pH=7.0) alone or in a buffer with 0.8 mg/mL of transferrin at a total volume of 1 mL. The mixture was then exposed to a 525 nm laser source (130 mW) and the absorbance at the maximal absorbance in visible range (432 nm for TLD1433, 425 nm for TLD143310 and 562 nm for TLDOsH2dppn) was measured at specific time points. The plot represents the absorbance ratio (absorbance of exposed samples/absorbance of unexposed sample) as a function of the number of incident photons per $cm^{-2}$. Decreasing absorbance ratio signifies bleaching of the photosensitizer.

Figure 6A:
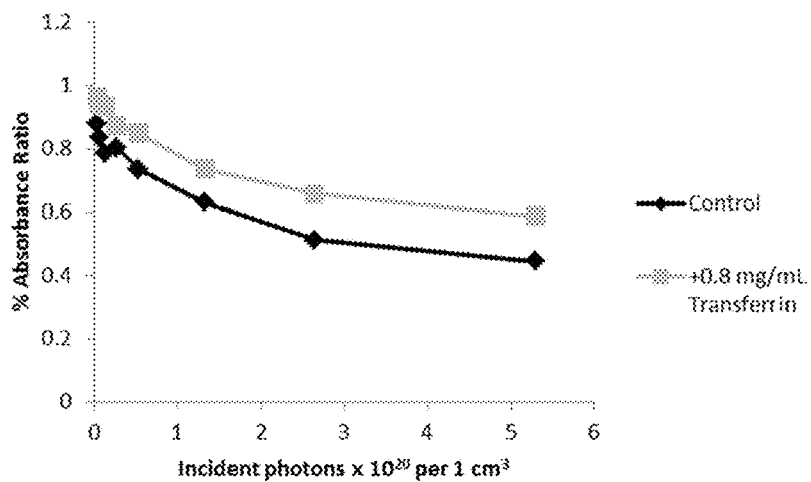
FIGS. 6A, 6B and 6C show graphs of absorbance ratio against incident photons.
Figure 6B:
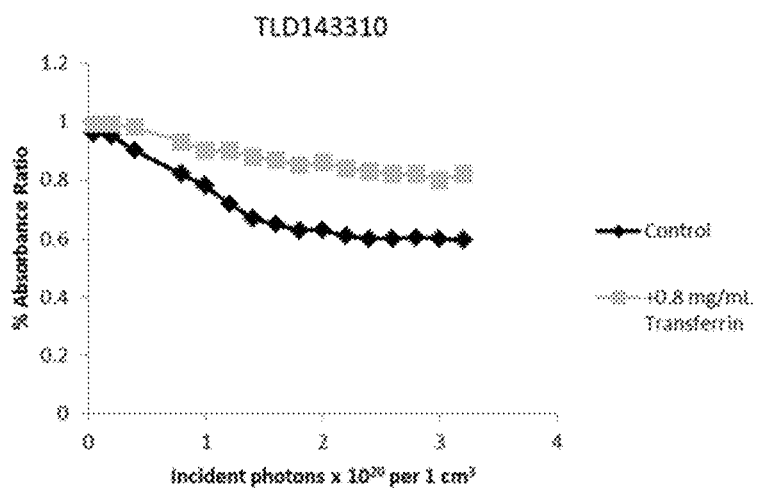
Figure 6C:
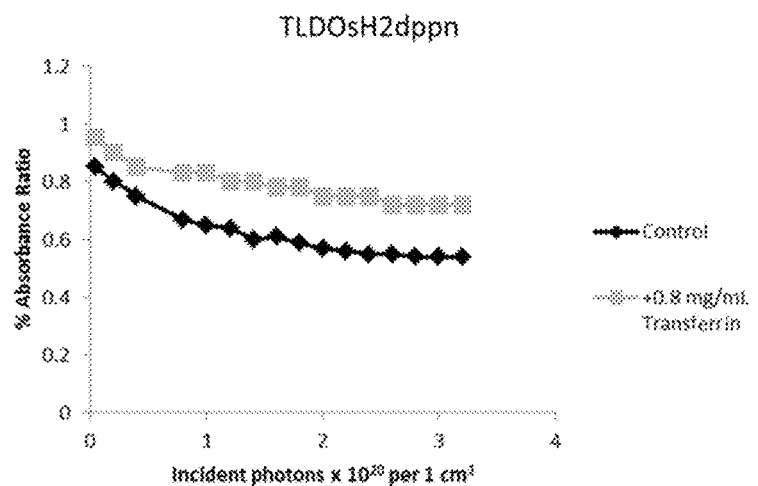

Effect of Transferrin on bleaching of Ruthenium (TLD1433, FIG. 6A), Ruthenium-Rhodium (TLD143310, FIG. 6B—Prophetic) and Osmium (TLDOsH2dppn, FIG. 6C—Prophetic)-based compounds at 525 nm.

In the presence of transferrin, bleaching of the photosensitizers was reduced.

Example 7 (Prophetic)

Photosensitizers (10 uM) were dissolved in phosphate buffer+100 mM NaCl (pH=7.0) alone or in a buffer with 0.8 mg/mL of transferrin at a total volume of 1 mL. The mixture was then exposed to a 525 nm laser source (130 mW) and the absorbance at 530 nm was measured at specific time points. The plot represents the absorbance ratio (absorbance of exposed samples/absorbance of unexposed sample) as a function of the number of incident photons per $cm^{-2}$. Decreasing absorbance ratio signifies bleaching of the photosensitizer.

Figure 7A:
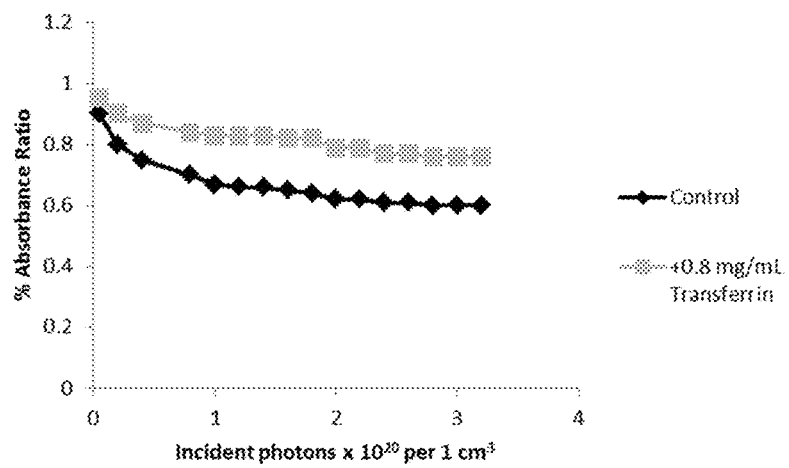
FIGS. 7A, 7B and 7C show graphs of absorbance ratio against incident photons.
Figure 7B:
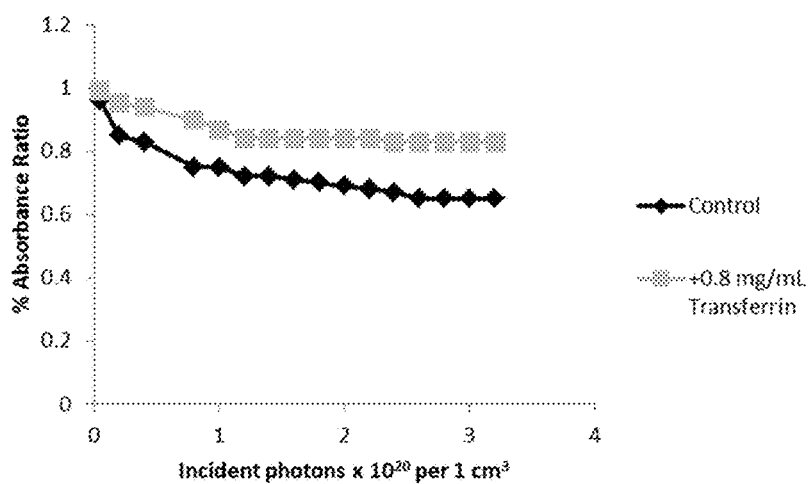
Figure 7C:
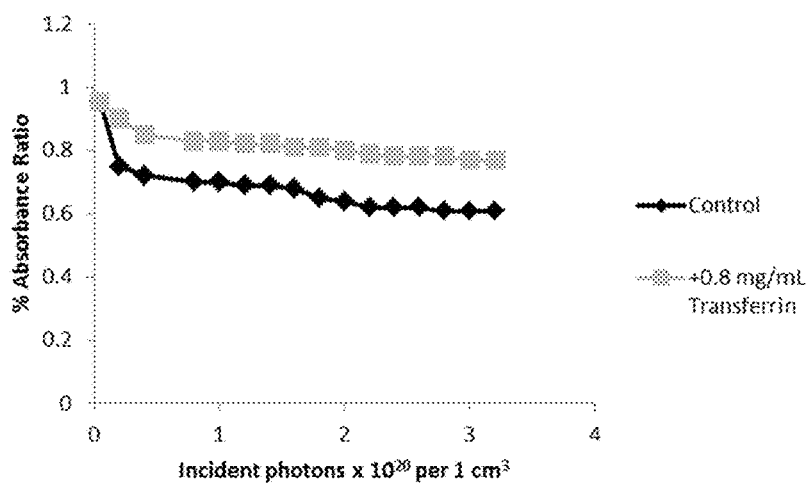

Effect of Transferrin on bleaching of Ruthenium (TLD1433, FIG. 7A), Ruthenium-Rhodium (TLD143310, FIG. 7B) and Osmium (TLDOsH2dppn, FIG. 7C)-based compounds: absorbance at 525 nm. In the presence of transferrin, bleaching of the photosensitizers was reduced. Transferrin partially protects photosensitizers from photobleaching.

Example 8 (Prophetic)

Photosensitizers (10 uM) were dissolved in phosphate buffer+100 mM NaCl (pH=7.0) alone or in a buffer with 0.8 mg/mL of transferrin at a total volume of 1 mL. The mixture was then exposed to a 525 nm laser source (130 mW) and the absorbance at 635 nm was measured at specific time points. The plot represents the absorbance ratio (absorbance of exposed samples/absorbance of unexposed sample) as a function of the number of incident photons per $cm^{-2}$. Decreasing absorbance ratio signifies bleaching of the photosensitizer.

Effect of Transferrin on bleaching of Ruthenium (TLD1433, FIG. 8A), Ruthenium-Rhodium (TLD143310, FIG. 8B) and Osmium (TLDOsH2dppn, FIG. 8C) based compounds: absorbance at 635 nm. In the presence of transferrin, bleaching of the photosensitizers was reduced. Transferrin partially protects photosensitizers form photobleaching.

Example 9 (Prophetic)

Photosensitizers (10 uM) were dissolved in phosphate buffer+100 mM NaCl (pH=7.0) alone or in a buffer with 0.8 mg/mL of transferrin at a total volume of 1 mL. The mixture was then exposed to a 525 nm laser source (130 mW) and the absorbance at 808 nm was measured at specific time points. The plot represents the absorbance ratio (absorbance of exposed samples/absorbance of unexposed sample) as a function of the number of incident photons per $cm^{-2}$. Decreasing absorbance ratio signifies bleaching of the photosensitizer.

Effect of Transferrin on bleaching of Ruthenium (TLD1433, Panel A), Ruthenium-Rhodium (TLD143310, Panel B) and Osmium (TLDOsH2dppn, Panel C) based compounds: absorbance at 808 nm. In presence of transferrin, bleaching of the photosensitizers was reduced. Transferrin partially protects photosensitizers form photobleaching.

Example 10 (Prophetic)

ROS Production

Table 1 shows singlet oxygen production by the Ruthenium (TLD1433), Ruthenium-Rhodium (TLD143310) and Osmium (TLDOsH2dppn)-based PS at 530 nm & 1092 J cm−2 incident energy.

TABLE 1

|  | TLD1433 | TLD143310 | TLDOsH2dppn |
|---|---|---|---|
| Phosphate buffer |  |  |  |
| no transferrin | 22471 | 21068 | 25937 |
| 0.8 mg/mL transferrin | 45568 | 32816 | 42816 |
| 1.6 mg/mL transferrin | 61568 | 55934 | 56372 |
| 3.2 mg/mL transferrin | 82652 | 751407 | 77219 |
| Incomplete DMEM |  |  |  |
| no transferrin | 32398 | 21936 | 36391 |
| 0.8 mg/mL transferrin | 53549 | 42138 | 35127 |
| 1.6 mg/mL transferrin | 73657 | 52384 | 43927 |
| 3.2 mg/mL transferrin | 95368 | 71573 | 61734 |

Example 11: (Prophetic)

Table 2 shows hydroxyl radical production by the Ruthenium (TLD1433), Ruthenium-Rhodium (TLD143310) and Osmium (TLDOsH2dppn)-based PS at 530 nm & 1092 J cm−2 incident energy.

TABLE 2

|  | TLD1433 | TLD143310 | TLDOsH2dppn |
|---|---|---|---|
| Phosphate buffer |  |  |  |
| no transferrin | 31358 | 28030 | 25290 |
| 0.8 mg/mL transferrin | 112047 | 70107 | 41037 |
| 1.6 mg/mL transferrin | 130308 | 121038 | 83034 |
| 3.2 mg/mL transferrin | 165023 | 153096 | 120307 |
| Incomplete DMEM |  |  |  |
| no transferrin | 41034 | 30348 | 32934 |
| 0.8 mg/mL transferrin | 150237 | 60108 | 70308 |
| 1.6 mg/mL transferrin | 182037 | 130025 | 132309 |
| 3.2 mg/mL transferrin | 190608 | 162027 | 164301 |

Example 12: (Prophetic)

Table 3 shows singlet oxygen production by the Ruthenium (TLD1433), Ruthenium-Rhodium (TLD143310) and Osmium (TLDOsH2dppn)-based PS at 635 nm & 649 J cm−2 incident energy.

TABLE 3

|  | TLD1433 | TLD143310 | TLDOsH2dppn |
|---|---|---|---|
| Phosphate buffer |  |  |  |
| no transferrin | 91374 | 10289 | 10392 |
| 0.8 mg/mL transferrin | 53124 | 41301 | 42837 |
| 1.6 mg/mL transferrin | 57621 | 68027 | 51832 |
| 3.2 mg/mL transferrin | 72218 | 75280 | 72938 |
| Incomplete DMEM |  |  |  |
| no transferrin | 19929 | 9507 | 15109 |
| 0.8 mg/mL transferrin | 39824 | 31937 | 53931 |
| 1.6 mg/mL transferrin | 82438 | 70218 | 75293 |
| 3.2 mg/mL transferrin | 95341 | 75317 | 81807 |

Example 13 (Prophetic)

Table 4 shows hydroxyl radical production by the Ruthenium (TLD1433), Ruthenium-Rhodium (TLD143310) and Osmium (TLDOsH2dppn)-based PS at 635 nm & 649 J cm−2 incident energy.

TABLE 4

|  | TLD1433 | TLD143310 | TLDOsH2dppn |
|---|---|---|---|
| Phosphate buffer |  |  |  |
| no transferrin | 12608 | 15000 | 8804 |
| 0.8 mg/mL transferrin | 71907 | 50328 | 25280 |
| 1.6 mg/mL transferrin | 82093 | 81867 | 45372 |
| 3.2 mg/mL transferrin | 101293 | 85361 | 72316 |
| 9 Incomplete DMEM |  |  |  |
| no transferrin | 18107 | 15280 | 12093 |
| 0.8 mg/mL transferrin | 98928 | 43623 | 32531 |
| 1.6 mg/mL transferrin | 119307 | 72901 | 42806 |
| 3.2 mg/mL transferrin | 152704 | 93150 | 73624 |

Example 14 (Prophetic)

Table 5 shows singlet oxygen production by the Ruthenium (TLD1433), Ruthenium-Rhodium (TLD143310) and Osmium (TLDOsH2dppn)-based PS at 808 nm & 4000 J cm−2 incident energy.

TABLE 5

|  | TLD1433 | TLD143310 | TLDOsH2dppn |
|---|---|---|---|
| Phosphate buffer |  |  |  |
| no transferrin | 10621 | 9000 | 8000 |
| 0.8 mg/mL transferrin | 41934 | 20000 | 10000 |
| 1.6 mg/mL transferrin | 56305 | 30000 | 30000 |
| 3.2 mg/mL transferrin | 62861 | 50000 | 40000 |
| Incomplete DMEM |  |  |  |
| no transferrin | 0 | 0 | 11907 |
| 0.8 mg/mL transferrin | 1204 | 1245 | 25384 |

TABLE 5-continued

|  | TLD1433 | TLD143310 | TLDOsH2dppn |
|---|---|---|---|
| 1.6 mg/mL transferrin | 22394 | 12307 | 55631 |
| 3.2 mg/mL transferrin | 36027 | 25193 | 62804 |

Example 15

Table 6 shows hydroxyl radical production by the Ruthenium (TLD1433), Ruthenium-Rhodium (TLD143310) and Osmium (TLDOsH2dppn)-based PS at 808 nm & 4000 J cm−2 incident energy.

TABLE 6

|  | TLD1433 | TLD143310 | TLDOsH2dppn |
|---|---|---|---|
| Phosphate buffer |  |  |  |
| no transferrin | 15610 | 12305 | 8931 |
| 0.8 mg/mL transferrin | 22967 | 15034 | 13408 |
| 1.6 mg/mL transferrin | 56390 | 31384 | 20392 |
| 3.2 mg/mL transferrin | 61832 | 63904 | 56094 |
| Incomplete DMEM |  |  |  |
| no transferrin | 503 | 427 | 14237 |
| 0.8 mg/mL transferrin | 701 | 714 | 42305 |
| 1.6 mg/mL transferrin | 20357 | 12397 | 77024 |
| 3.2 mg/mL transferrin | 41395 | 23297 | 102864 |

Example 16 (Prophetic)

The photosensitizers were diluted in phosphate buffer (pH=7.0)+100 mM NaCl or incomplete DMEM. The irradiation was performed in 96-well plates (100 uL working volume). Generation of singlet oxygen was measured by fluorescence signal of SOG indicator, generation of hydroxyl radical by fluorescence signal of HPF indicator. The signal presented is a result of subtraction of the signal in the presence of scavengers (NaN$_3$ for singlet oxygen and DMTU for hydroxyl radical) from the total fluorescence signal.

Ruthenium (TLD1433), Ruthenium-Rhodium (TLD143310) and Osmium (TLDOsH2dppn) based photosensitizers produce reactive oxygen species (ROS) under 525 nm (0.250 mW cm−2), 650 nm (0.119 mW cm−2) and NIR (808 nm, 747 mW cm−2) irradiation.

In the presence of transferrin, generation of both singlet oxygen and hydroxyl radical is potentiated in a dose-dependent manner: higher concentration of transferrin induces greater generation of ROS. Generation of hydroxyl radical is potentiated to a much greater extent than that of singlet oxygen suggesting a switch to Type I photoreaction in the presence of transferrin.

Example 17 (Prophetic)

Intracellular Uptake

Cell culture (U87 cells) was exposed to 200 uM of the photosensitizer without additional transferrin and in the presence of 0.8 mg/mL transferrin for 4 hours. The incubation mix was washed away and the cells were collected, counted, and lysed. Lysed solution was dissolved in nitric acid and appropriate metals concentration was measured using inductively coupled plasma mass spectrometry. The metals concentration is directly proportional to the concentration of the photosensitizer.

Figure 10A:
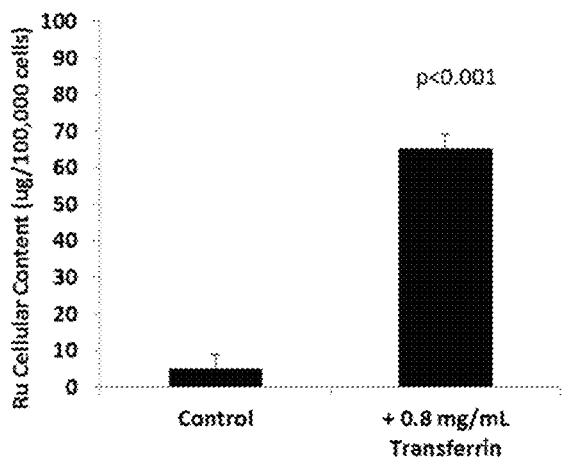
FIGS. 10A, 10B and 10C show graphs of cellular uptake of metals by control and test samples.
Figure 10B:
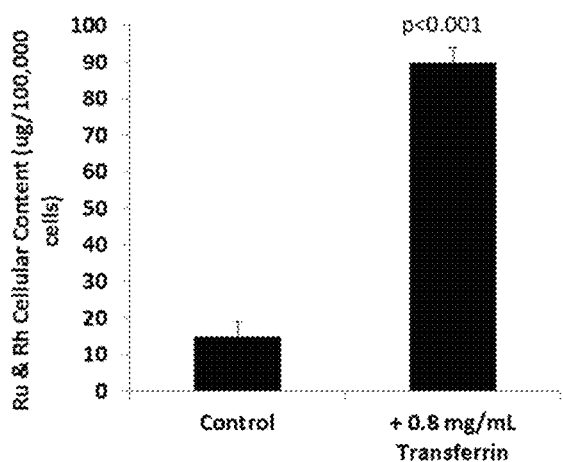
Figure 10C:
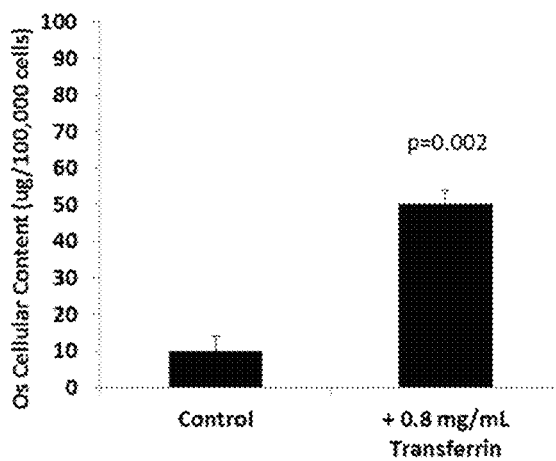

FIGS. 10A, 10B and 10C show transferrin facilitated uptake of Ruthenium (TLD1433, FIG. 10A), Ruthenium-Rhodium (TLD143310, FIG. 10B) and Osmium (TLDOsH2dppn, FIG. 10C) based photosensitizers into cancer cells.

Cellular accumulation of the photosensitizers was higher in the presence of transferrin. Since tumor cells have been shown to have higher expression of membrane transferrin receptor, these results show that the mentioned photosensitizers can preferentially accumulate in tumor cells.

Example 18 (Prophetic)

Uptake by Normal Cells

Cell culture (normal human fibroblasts) was exposed to 200 uM of the photosensitizer without additional transferrin and in the presence of 0.8 mg/mL transferrin for 4 hours. The incubation mix was washed away and the cells were collected, counted, and lysed. Lysed solution was dissolved in nitric acid and appropriate metals concentration was measured using inductively coupled plasma mass spectrometry. The metals concentration is directly proportional to the concentration of the photosensitizer.

Figure 11A:
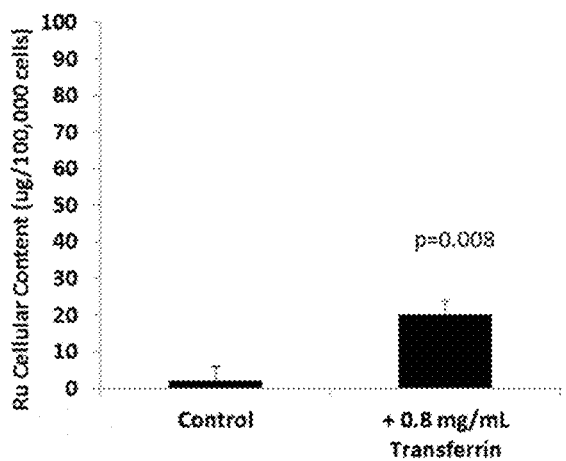
FIGS. 11A, 11B and 11C show graphs of cellular uptake of metals by control and test samples.
Figure 11B:
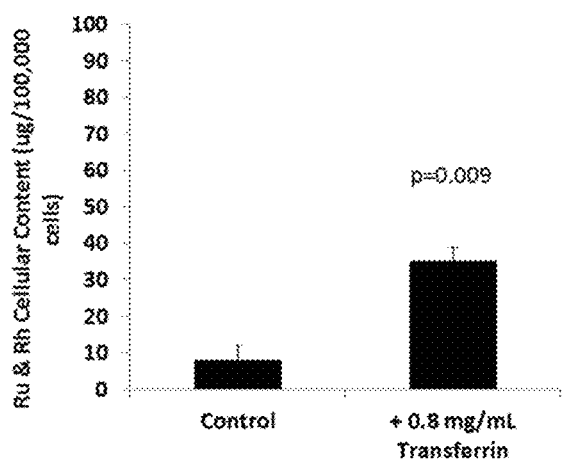
Figure 11C:
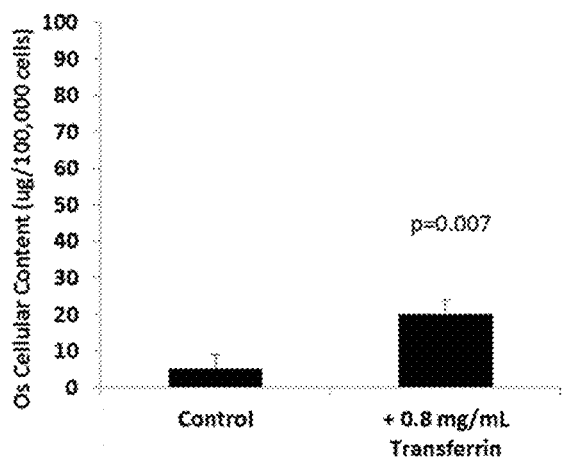

FIGS. 11A, 11B and 11C show transferrin facilitated uptake of Ruthenium (TLD1433, FIG. 11A), Ruthenium-Rhodium (TLD143310, FIG. 11B) and Osmium (TLDOsH2dppn, FIG. 11C) based photosensitizers into normal cells. Cellular accumulation of the photosensitizers was higher in the presence of transferrin. However, the effect of transferrin on the uptake is to a much lesser extent than for cancer cells indicating uptake improvement preferentially in cancer cells.

Example 19

In Vitro—Dark Toxicity

Figure 12A:
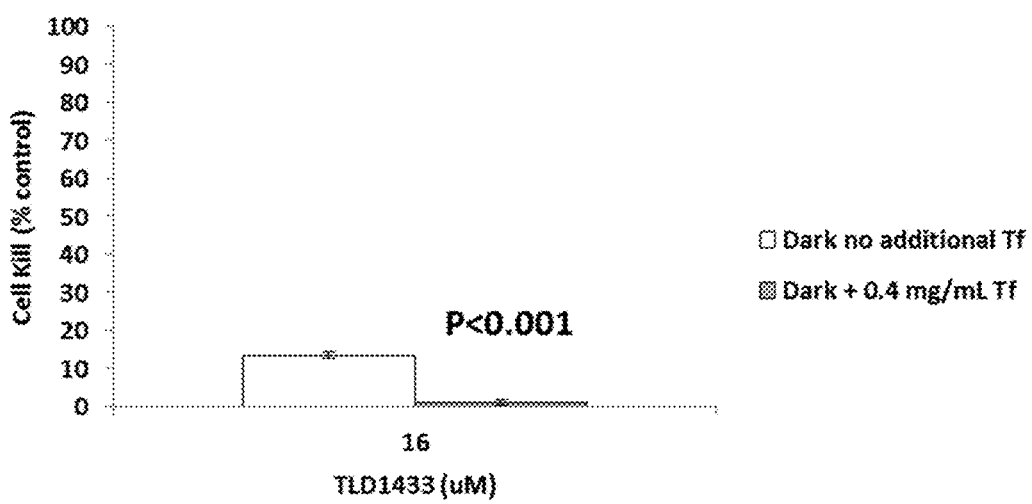
FIGS. 12A and 12B show graphs of cell kill with and without transferrin.
Figure 12B:
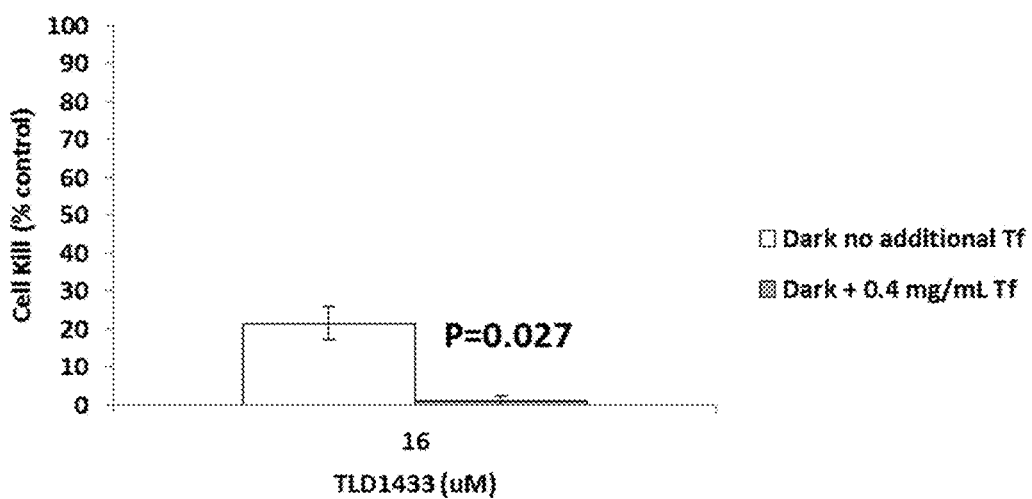

The photosensitizer was pre-mixed with 0.4 mg/mL human transferrin and incubated for 1 hour at 37° C. In control group (no additional transferrin), equivalent volume of no-transferrin medium was added. The cells were subsequently incubated with the pre-mixes for 30 minutes (FIG. 12A) or 90 minutes (FIG. 12B). After that, the medium was replaced with a fresh one (without photosensitizer and transferrin). On the next day (21 hours post-irradiation), viability of the cells was measured using Presto Blue viability assay, and percent of cell kill was calculated.

The presence of transferrin decreases dark toxicity (photosensitizer alone) of Ruthenium-based photosensitizers (TLD1433) on AY27 cancer cell line. Transferrin decreases dark toxicity of TLD1433. This contributes to an increased safety of PDT treatment in the presence of transferrin. Together with the evidence of binding of TLD1433 to transferrin, these results suggest facilitated uptake of TLD1433 into cells in the presence of transferrin. Increase in PDT efficacy together with the decrease in dark toxicity suggests an increase in therapeutic ratio of TLD1433 when it is used mixed with transferrin.

Example 20 (Prophetic)

The photosensitizer was pre-mixed with 0.4 mg/mL human transferrin and incubated for 1 hour at 37° C. In control group (no additional transferrin), equivalent volume of no-transferrin medium was added. The cells were subsequently incubated with the pre-mixes for 30 minutes. After that, the medium was replaced with a fresh one (without photosensitizer and transferrin). On the next day (21 hours post-irradiation), viability of the cells was measured using Presto Blue viability assay, and percent of cell kill was calculated.

Figure 13A:
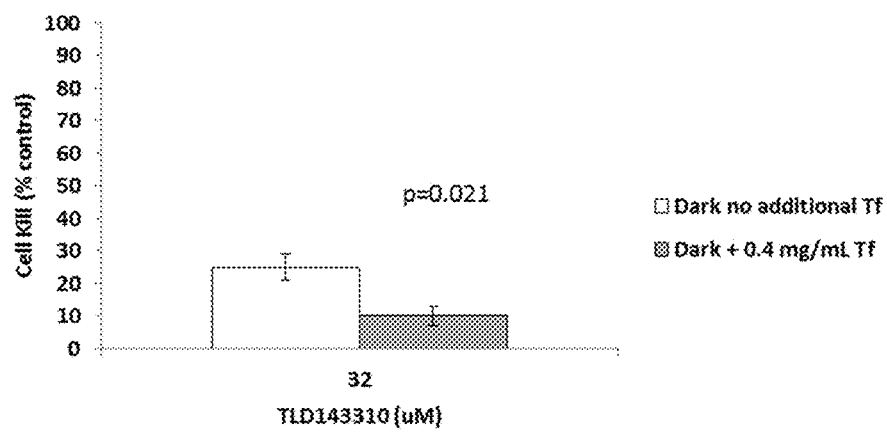
FIGS. 13A and 13B show graphs of cell kill with and without transferrin.
Figure 13B:
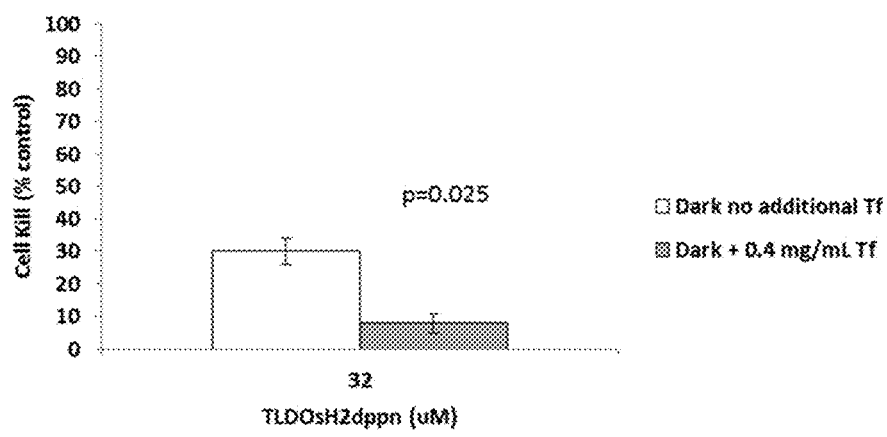

The presence of transferrin decreases dark toxicity (photosensitizer alone) of Ruthenium-Rhodium (TLD143310, FIG. 13A) and Osmium (TLDOsH2dppn, FIG. 13B) based photosensitizers on AY27 cancer cell line. Transferrin decreases dark toxicity of the photosensitizers. This contributes to an increased safety of PDT treatment in the presence of transferrin.

Example 21

In Vitro PDT Effect

Figure 14A:
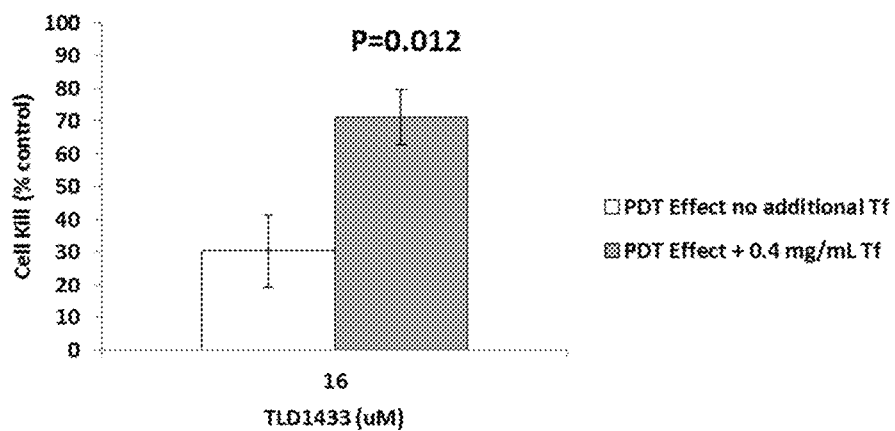
FIGS. 14A and 14B show graphs of cell kill with and without transferrin.
Figure 14B:
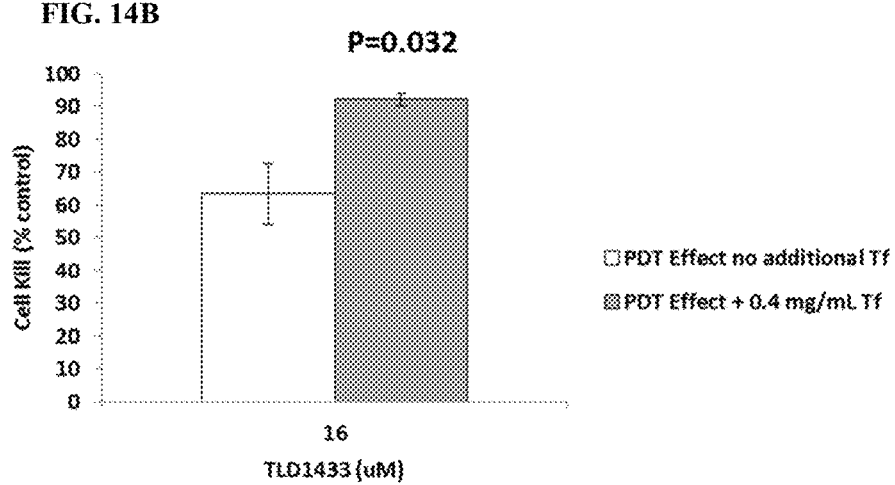

The photosensitizer was pre-mixed with 0.4 mg/mL human transferrin and incubated for 1 hour at 37° C. In control group (no additional transferrin), equivalent volume of no-transferrin medium was added. The cells were subsequently incubated with the pre-mixes for 30 minutes (FIG. 14A) or 90 minutes (FIG. 14B). After that, the medium was replaced with a fresh one (without photosensitizer and transferrin) and the cells were irradiated. On the next day (21 hours post-irradiation), viability of the cells was measured using Presto Blue viability assay, and percent of cell kill was calculated. The PDT effect shown is a result of subtraction of "photosensitizer alone" and "light alone" cell kill from the total PDT cell kill.

The presence of transferrin increases PDT effect (635 nm, 90 J cm−2) of Ruthenium-based photosensitizers (TLD1433) on AY27 cancer cell line. Transferrin potentiates PDT effect of the photosensitizer even at short loading time (30 minutes). This allows for safer PDT treatment due to shorter treatment time and the use of lower concentrations of the photosensitizers. Together with the evidence of binding of TLD1433 to transferrin, these results suggest facilitated uptake of TLD1433 into cells in the presence of transferrin.

Example 22 (Prophetic)

The photosensitizer was pre-mixed with 0.4 mg/mL human transferrin and incubated for 1 hour at 37° C. In control group (no additional transferrin), equivalent volume of no-transferrin medium was added. The cells were subsequently incubated with the pre-mixes for 30 minutes. After that, the medium was replaced with a fresh one (without photosensitizer and transferrin) and the cells were irradiated. On the next day (21 hours post-irradiation), viability of the cells was measured using Presto Blue viability assay, and percent of cell kill was calculated. The PDT effect shown is a result of subtraction of "photosensitizer alone" and "light alone" cell kill from the total PDT cell kill.

Figure 15A:
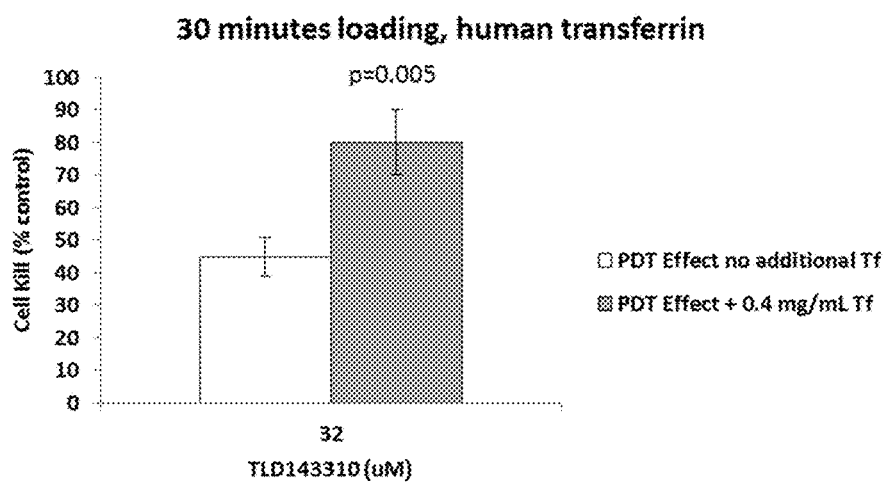
FIGS. 15A and 15B show graphs of cell kill with and without transferrin.
Figure 15B:
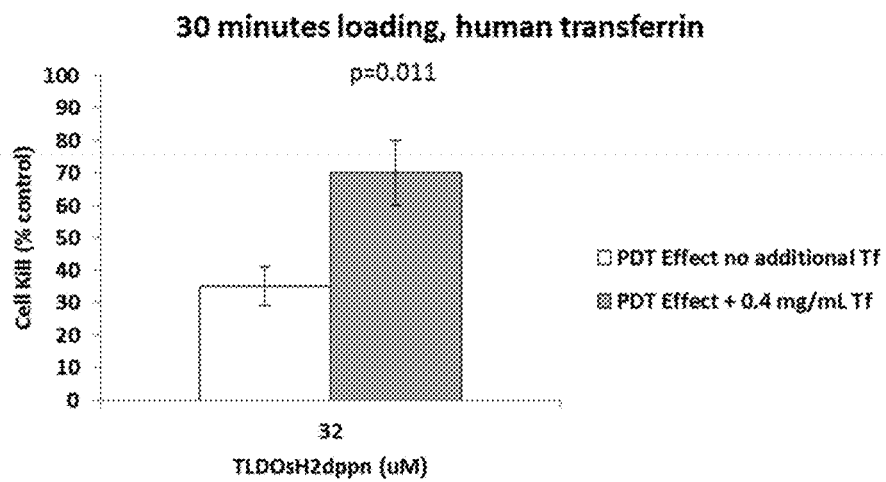
Figure 16A:
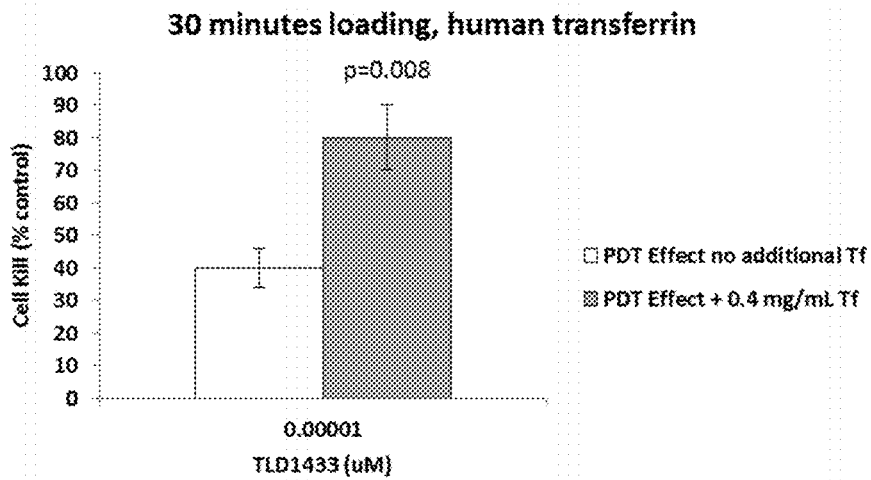
FIGS. 16A, 16B and 16C show graphs of cell kill with and without transferrin.
Figure 16B:
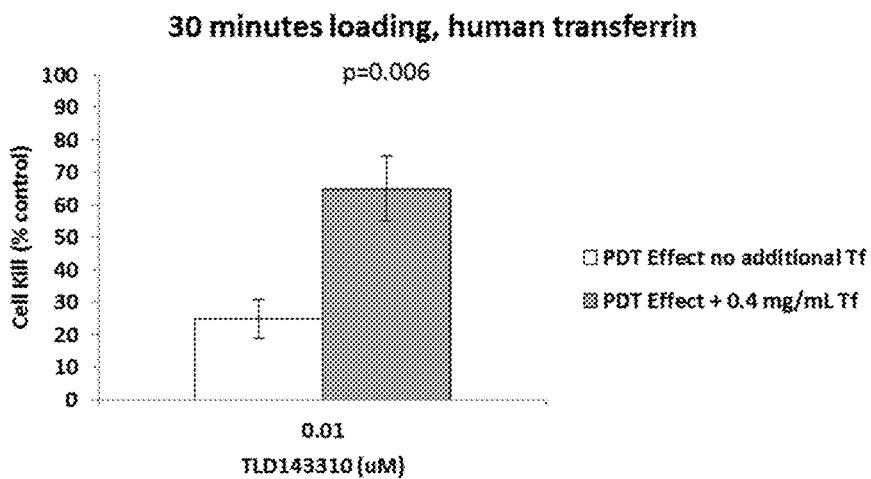
Figure 16C:
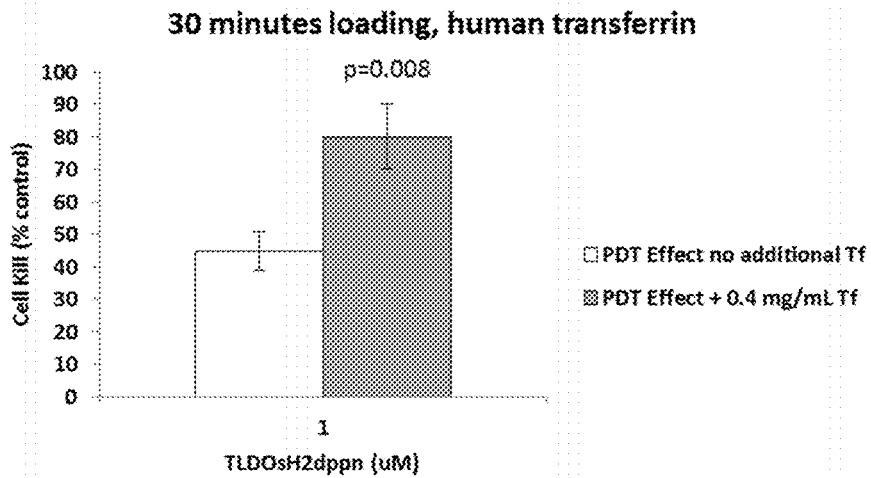

The presence of transferrin increases PDT effect (635 nm, 90 J cm−2) of Ruthenium-Rhodium (TLD143310, FIG. 15A) and Osmium (TLDOsH2dppn, FIG. 15B) based photosensitizers on AY27 cancer cell line.

Transferrin potentiates PDT effect of the photosensitizers even at short loading time (30 minutes). This allows for safer PDT treatment due to shorter treatment time and the use of lower concentrations of the photosensitizers. Together with the evidence of binding of the photosensitizers to transferrin, these results suggest facilitated uptake of the photosensitizers into cells in the presence of transferrin.

Increase in PDT efficacy together with the decrease in dark toxicity suggests an increase in therapeutic ratio of Ruthenium (TLD1433), Ruthenium-Rhodium (TLD143310) and Osmium (TLDOsH2dppn) based photosensitizers when they are pre-mixed with transferrin.

Example 23 (Prophetic)

The photosensitizer was pre-mixed with 0.4 mg/mL human transferrin and incubated for 1 hour at 37° C. In control group (no additional transferrin), equivalent volume of no-transferrin medium was added. The cells were subsequently incubated with the pre-mixes for 30 minutes. After that, the medium was replaced with a fresh one (without photosensitizer and transferrin) and the cells were irradiated. On the next day (21 hours post-irradiation), viability of the cells was measured using Presto Blue viability assay, and percent of cell kill was calculated. The PDT effect shown is a result of subtraction of "photosensitizer alone" and "light alone" cell kill from the total PDT cell kill.

The presence of transferrin increases PDT effect (530 nm, 90 J cm−2) of Ruthenium-Rhodium (TLD143310, Panel A) and Osmium (TLDOsH2dppn, Panel B) based photosensitizers on AY27 cancer cell line. Transferrin potentiates PDT effect of the photosensitizers even at short loading time (30 minutes). This allows for safer PDT treatment due to shorter treatment time and the use of lower concentrations of the photosensitizers. Together with the evidence of binding of the photosensitizers to transferrin, these results suggest facilitated uptake of the photosensitizers into cells in the presence of transferrin.

Example 24

Pre-mixing with transferrin increases therapeutic ratio of Ruthenium (TLD1433), Ruthenium-Rhodium (TLD143310) and Osmium (TLDOsH2dppn) based photosensitizers, due to the increase in PDT efficacy together with the decrease in dark toxicity. See Table 7.

TABLE 7

| | Therapeutic Ratio | | | | | |
|---|---|---|---|---|---|---|
| | HT1376 cells | | U87 cells | | AY27 cells | |
| | No transferrin | Transferrin | No transferrin | Transferrin | No transferrin | Transferrin |
| | 530 nm, 90 J cm−2 | | | | | |
| TLD1433 | 19024.1 (Prophetic) | 50938.4 (Prophetic) | 27557.1 | 65002.3 (Prophetic) | 17356.2 (Prophetic) | 57324.1 (Prophetic) |

TABLE 7-continued

| | Therapeutic Ratio | | | | | |
|---|---|---|---|---|---|---|
| | HT1376 cells | | U87 cells | | AY27 cells | |
| | No transferrin | Transferrin | No transferrin | Transferrin | No transferrin | Transferrin |
| TLD143310 | 421.9 (Prophetic) | 835.7 (Prophetic) | 495.1 (Prophetic) | 1022.6 (Prophetic) | 473.1 (Prophetic) | 934.5 (Prophetic) |
| TLDOsH2dppn | 1548.2 (Prophetic) | 4963.8 (Prophetic) | 1307.3 | 5238.0 (Prophetic) | 1639.8 (Prophetic) | 5531.9 (Prophetic) |
| 650 nm, 90 J cm−2 | | | | | | |
| TLD1433 | 50.4 (Prophetic) | 100.8 (Prophetic) | 102.6 | 405.1 (Prophetic) | 79.2 (Prophetic) | 393.7 (Prophetic) |
| TLD143310 | 28.1 (Prophetic) | 52.7 (Prophetic) | 16.3 | 50.2 (Prophetic) | 25.1 (Prophetic) | 59.4 (Prophetic) |
| TLDOsH2dppn | 37.7 (Prophetic) | 61.9 (Prophetic) | 15.3 | 50.3 (Prophetic) | 28.7 (Prophetic) | 61.7 (Prophetic) |

Example 25 (Prophetic)

In Vitro Hypoxia

Figure 17A:
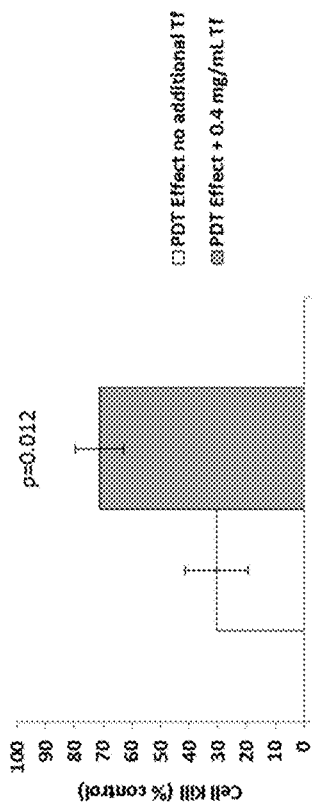
FIGS. 17A, 17B, 17C and 17D show graphs of cell kill with and without transferrin.
Figure 17B:
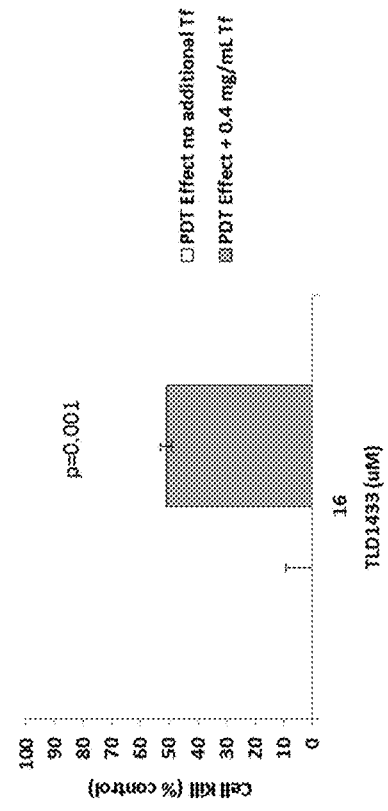
Figure 17C:
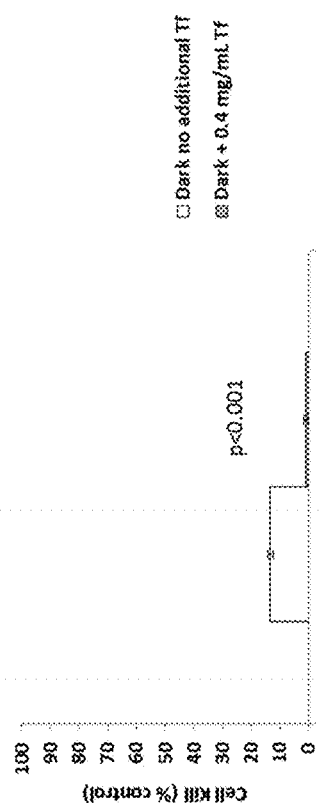
Figure 17D:
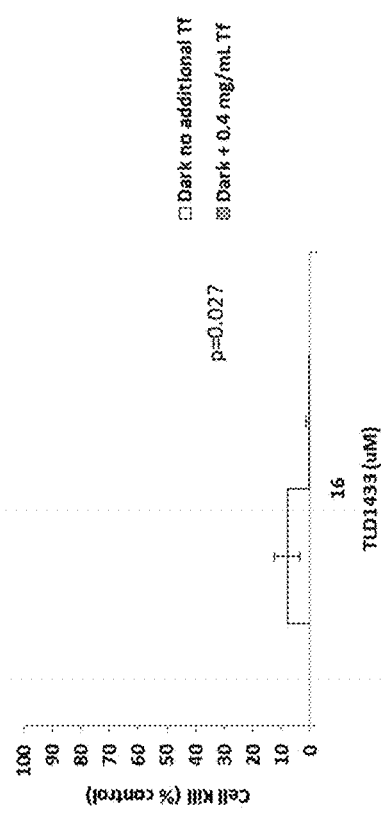

The cells were incubated for 90 minutes in premix of the photosensitizer and 0.4 mg/mL human transferrin (or without transferrin, as a control group) as described above for in vitro PDT. Dark toxicity and PDT effect of the photosensitizers on AY27 cell line under 635 nm (90 J cm−2) irradiation in the absence and presence of transferrin in normoxic (FIGS. 17A, 17B) and hypoxic (0.5-0.1% $O_2$, FIGS. 17C, 17D) conditions. The cells were incubated with the photosensitizer and transferrin for 90 minutes. After that, the cells were irradiated and the medium was replaced with a fresh one (without photosensitizer and transferrin). On the next day (21 hours post-irradiation), viability of the cells was measured using Presto Blue viability assay, and percent of cell kill was calculated. The PDT effect shown is a result of subtraction of "photosensitizer alone" and "light alone" cell kill from the total PDT cell kill.

The presence of transferrin ensured PDT effect (635 nm, 90 J cm−2) of Ruthenium (TLD1433) based photosensitizers on AY27 cancer cell line under hypoxic conditions. Transferrin induces PDT activity in hypoxia, which is not observed in the absence of transferrin. The presence of transferrin, therefore, allows for a greater efficacy of the Ruthenium-based photosensitizers during PDT treatment of bulky hypoxic tumors.

Example 26 (Prophetic)

The cells were incubated for 90 minutes in premix of the photosensitizer and 0.4 mg/mL human transferrin (or without transferrin, as a control group) as described above for in vitro PDT. Dark toxicity and PDT effect of the photosensitizers on AY27 cell line under 635 nm (90 J cm−2) irradiation in the absence and presence of transferrin in normoxic (FIGS. 18A, 18B) and hypoxic (0.5-0.1% $O_2$, FIGS. 18C, 18D) conditions. The cells were incubated with the photosensitizer and transferrin for 90 minutes. After that, the cells were irradiated and the medium was replaced with a fresh one (without photosensitizer and transferrin). On the next day (21 hours post-irradiation), viability of the cells was measured using Presto Blue viability assay, and percent of cell kill was calculated. The PDT effect shown is a result of subtraction of "photosensitizer alone" and "light alone" cell kill from the total PDT cell kill.

The presence of transferrin ensured PDT effect (635 nm, 90 J cm−2) of Ruthenium-Rhodium (TLD143310) based photosensitizers on AY27 cancer cell line under hypoxic conditions. Transferrin induces PDT activity in hypoxia, which is not observed in the absence of transferrin. The presence of transferrin, therefore, allows for a greater efficacy of the Ruthenium-Rhodium-based photosensitizers during PDT treatment of bulky hypoxic tumors.

Example 27 (Prophetic)

Figure 19A:
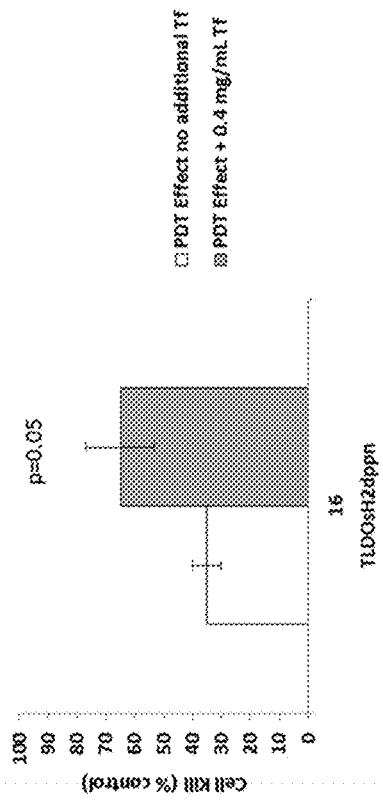
FIGS. 19A, 19B, 19C and 19D show graphs of cell kill with and without transferrin.
Figure 19B:
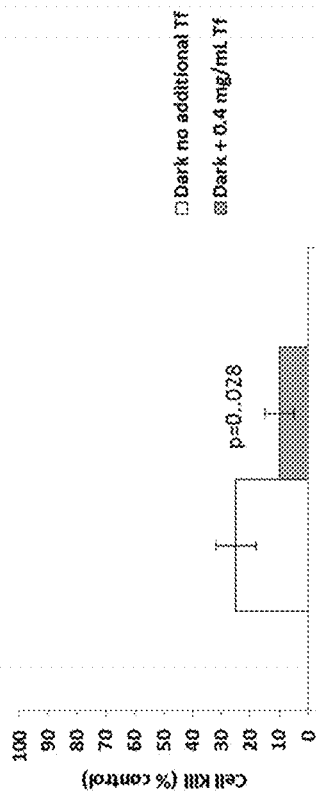
Figure 19C:
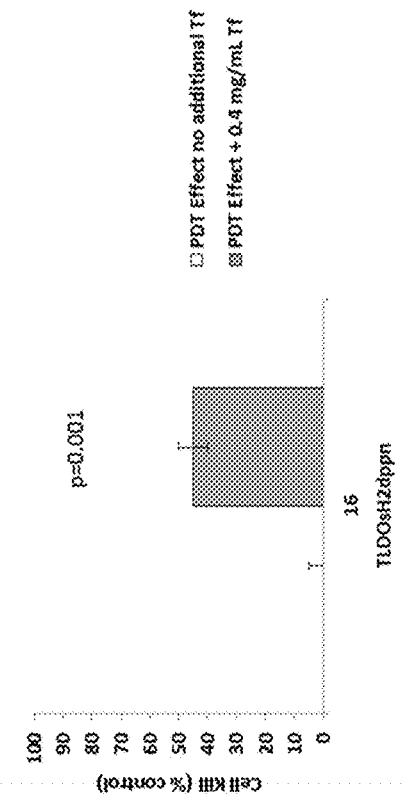
Figure 19D:
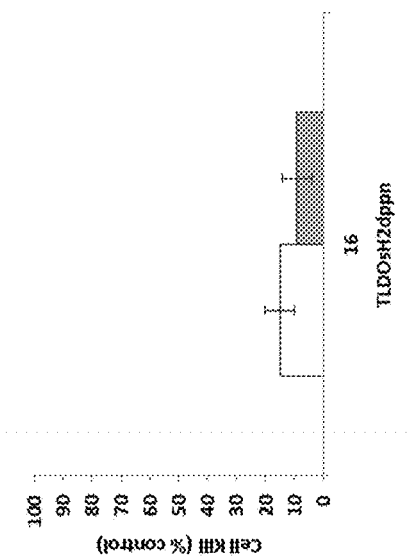

The cells were incubated for 90 minutes in premix of the photosensitizer and 0.4 mg/mL human transferrin (or without transferrin, as a control group) as described above for in vitro PDT. Dark toxicity and PDT effect of the photosensitizers on AY27 cell line under 635 nm (90 J cm−2) irradiation in the absence and presence of transferrin in normoxic (FIGS. 19A, 19B) and hypoxic (0.5-0.1% $O_2$, FIGS. 19C, 19D) conditions. The cells were incubated with the photosensitizer and transferrin for 90 minutes. After that, the cells were irradiated and the medium was replaced with a fresh one (without photosensitizer and transferrin). On the next day (21 hours post-irradiation), viability of the cells was measured using Presto Blue viability assay, and percent of cell kill was calculated. The PDT effect shown is a result of subtraction of "photosensitizer alone" and "light alone" cell kill from the total PDT cell kill.

The presence of transferrin ensured PDT effect (635 nm, 90 J cm−2) of Osmium (TLDOsH2dppn) based photosensitizers on AY27 cancer cell line under hypoxic conditions. Transferrin induces PDT activity in hypoxia, which is not observed in the absence of transferrin. The presence of transferrin, therefore, allows for a greater efficacy of the Osmium-based photosensitizers during PDT treatment of bulky hypoxic tumors.

Example 28 (Prophetic)

Transferrin Receptor Antibodies

Figure 20A:
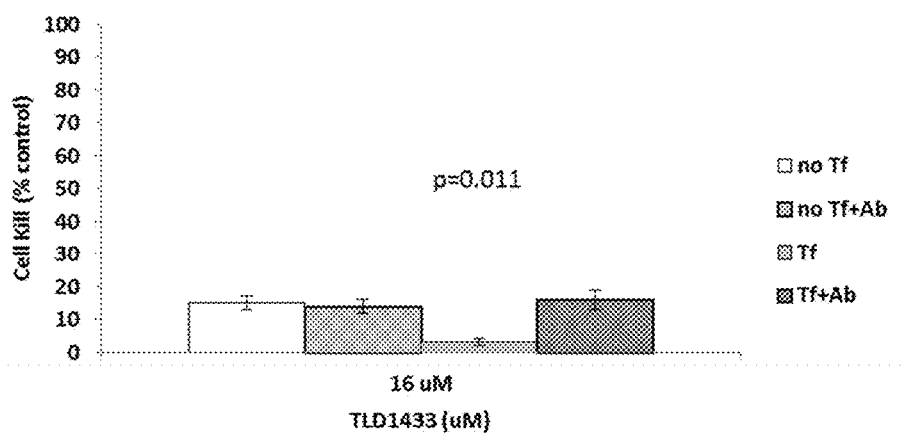
FIGS. 20A and 20B show graphs of cell kill with and without transferrin and with and without antibodies.
Figure 20B:
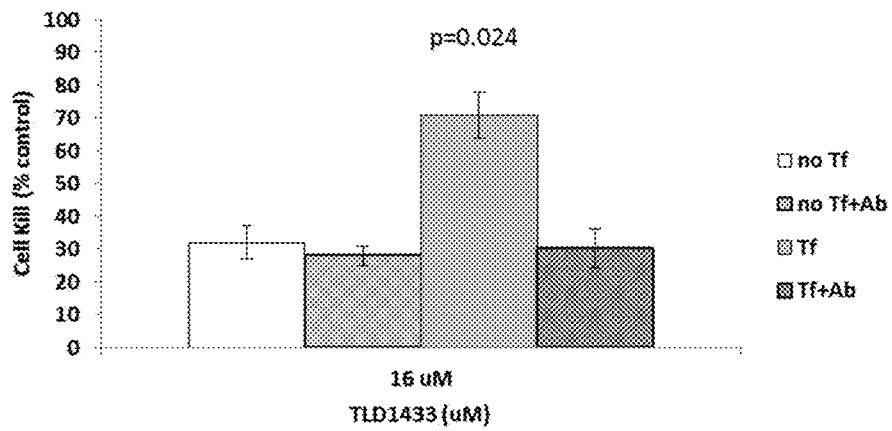

The cells were incubated with anti-transferrin receptor antibody. The photosensitizer was pre-mixed in parallel with 0.4 mg/mL human transferrin and incubated for 1 hour at 37° C. In control group (no additional transferrin), equivalent volume of no-transferrin medium was added. The cells were washed of the excess of antibody (the cells incubated in medium without antibody served as comparison groups) and incubated with the pre-mixes for 30 minutes. After that, the medium was replaced with a fresh one (without photosensitizer and transferrin) and the cells were irradiated. On the next day (21 hours post-irradiation), viability of the cells was measured using Presto Blue viability assay, and percent of cell kill was calculated. The PDT effect shown is a result of subtraction of "photosensitizer alone" and "light alone" cell kill from the total PDT cell kill. Dark toxicity is shown on FIG. 20A, PDT effect is shown on FIG. 20B.

Blocking of transferrin receptors of AY27 cancer cells prevents decrease in dark toxicity and facilitation of PDT effect (635 nm, 90 J cm−2) of Ruthenium (TLD1433) based photosensitizers. The results support the role of transferrin-mediated uptake of Ruthenium-based photosensitizers in decrease of their dark toxicity and facilitation of their PDT effect.

Example 29 (Prophetic)

Figure 21A:
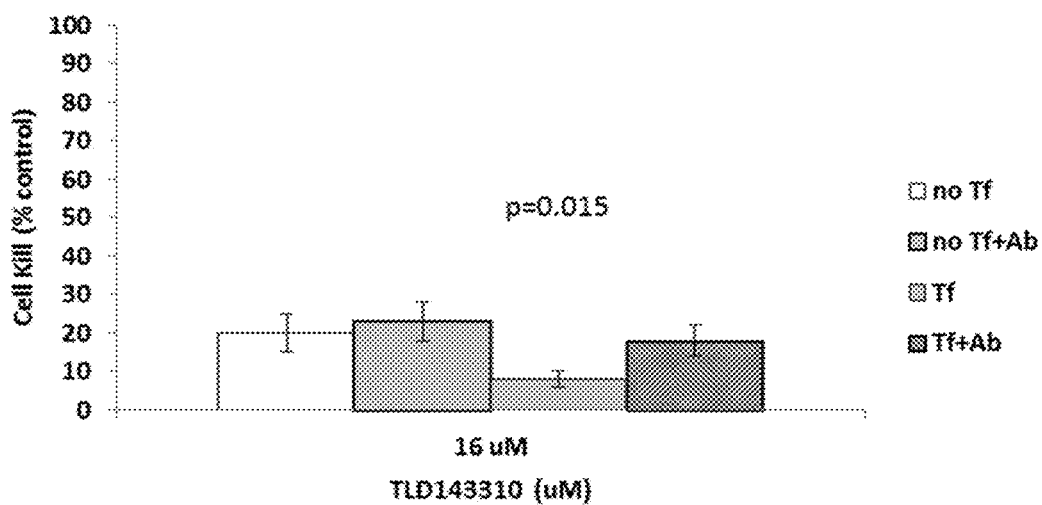
FIGS. 21A and 21B show graphs of cell kill with and without transferrin and with and without antibodies.
Figure 21B:
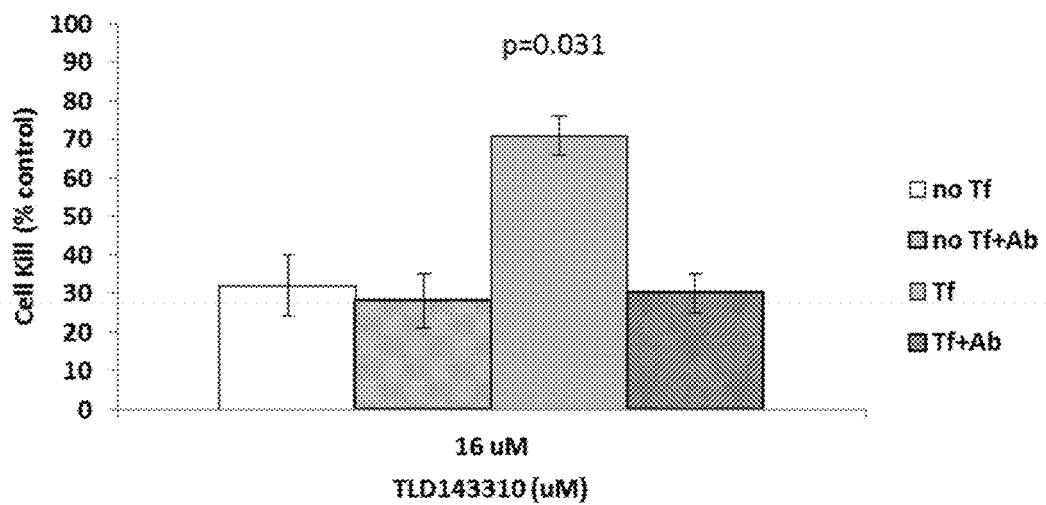

The cells were incubated with anti-transferrin antibody. The photosensitizer was pre-mixed in parallel with 0.4 mg/mL human transferrin and incubated for 1 hour at 37° C. In control group (no additional transferrin), equivalent volume of no-transferrin medium was added. The cells were washed of the excess of antibody (the cells incubated in medium without antibody served as comparison groups) and incubated with the pre-mixes for 30 minutes. After that, the medium was replaced with a fresh one (without photosensitizer and transferrin) and the cells were irradiated. On the next day (21 hours post-irradiation), viability of the cells was measured using Presto Blue viability assay, and percent of cell kill was calculated. The PDT effect shown is a result of subtraction of "photosensitizer alone" and "light alone" cell kill from the total PDT cell kill. Dark toxicity is shown on FIG. 21A, PDT effect is shown on FIG. 21B.

Blocking of transferrin receptors of AY27 cancer cells prevents decrease in dark toxicity and facilitation of PDT effect (635 nm, 90 J cm−2) of Ruthenium-Rhodium (TLD143310) based photosensitizers. The results support the role of transferrin-mediated uptake of Ruthenium-Rhodium based photosensitizers in decrease of their dark toxicity and facilitation of their PDT effect.

Example 30 (Prophetic)

Figure 22A:
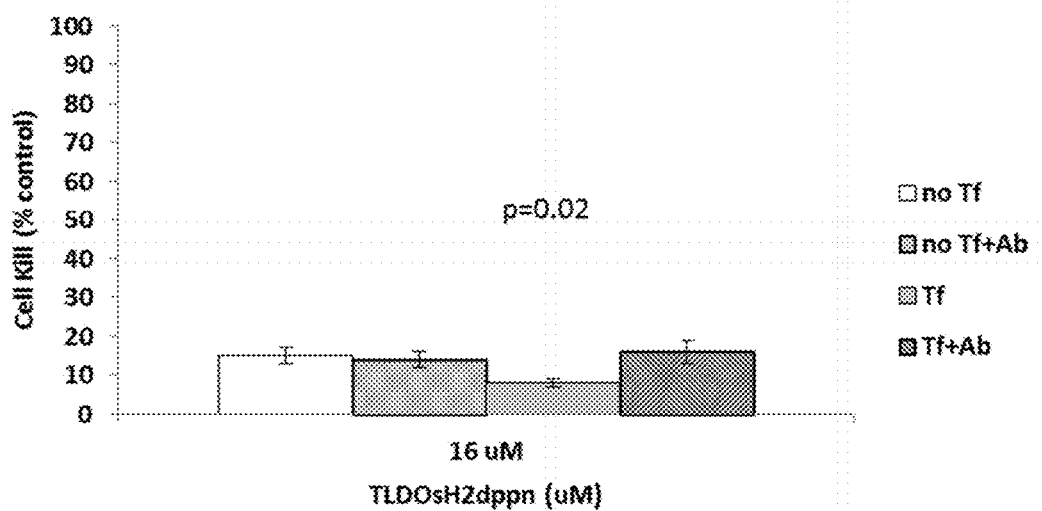
FIGS. 22A and 22B show graphs of cell kill with and without transferrin and with and without antibodies.
Figure 22B:
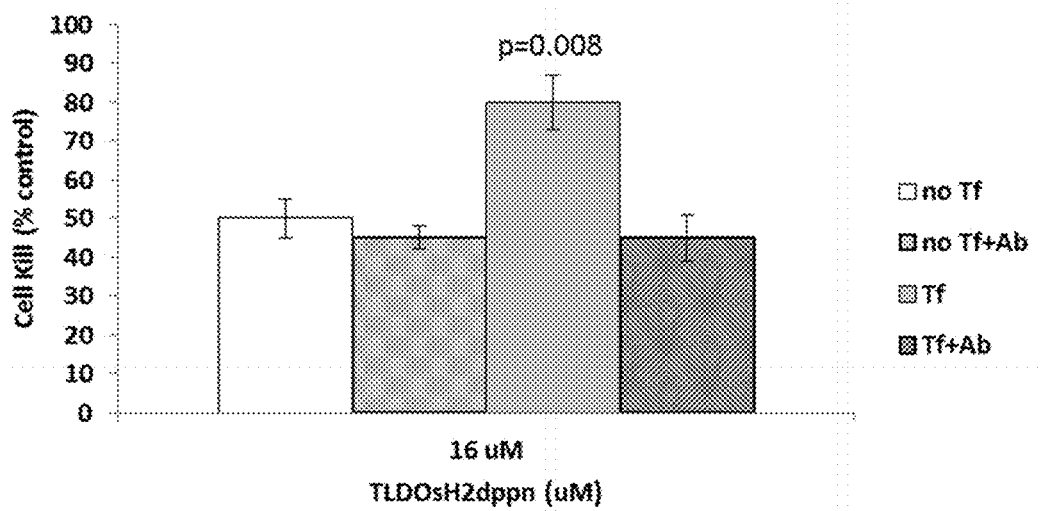

The cells were incubated with anti-transferrin antibody. The photosensitizer was pre-mixed in parallel with 0.4 mg/mL human transferrin and incubated for 1 hour at 37° C. In control group (no additional transferrin), equivalent volume of no-transferrin medium was added. The cells were washed of the excess of antibody (the cells incubated in medium without antibody served as comparison groups) and incubated with the pre-mixes for 30 minutes. After that, the medium was replaced with a fresh one (without photosensitizer and transferrin) and the cells were irradiated. On the next day (21 hours post-irradiation), viability of the cells was measured using Presto Blue viability assay, and percent of cell kill was calculated. The PDT effect shown is a result of subtraction of "photosensitizer alone" and "light alone" cell kill from the total PDT cell kill. Dark toxicity is shown in FIG. 22A, PDT effect is shown on FIG. 22B.

Blocking of transferrin receptors of AY27 cancer cells prevents decrease in dark toxicity and facilitation of PDT effect (635 nm, 90 J cm−2) of Osmium (TLDOsH2dppn) based photosensitizers. The results support the role of transferrin-mediated uptake of Osmium-based photosensitizers in decrease of their dark toxicity and facilitation of their PDT effect.

Example 31 (Prophetic)

In Vivo Tissue Uptake

Transferrin was dissolved in 40% PG in phosphate buffer (pH=7.0)+100 mM NaCl (0.1 mg/100 uL) and added to the photosensitizer solution (to achieve 10 mg/kg dose). The mixture was incubated for 1 hour prior to injection, and 100 uL of the mixture was injected i.v. to each animal.

Figure 23A:
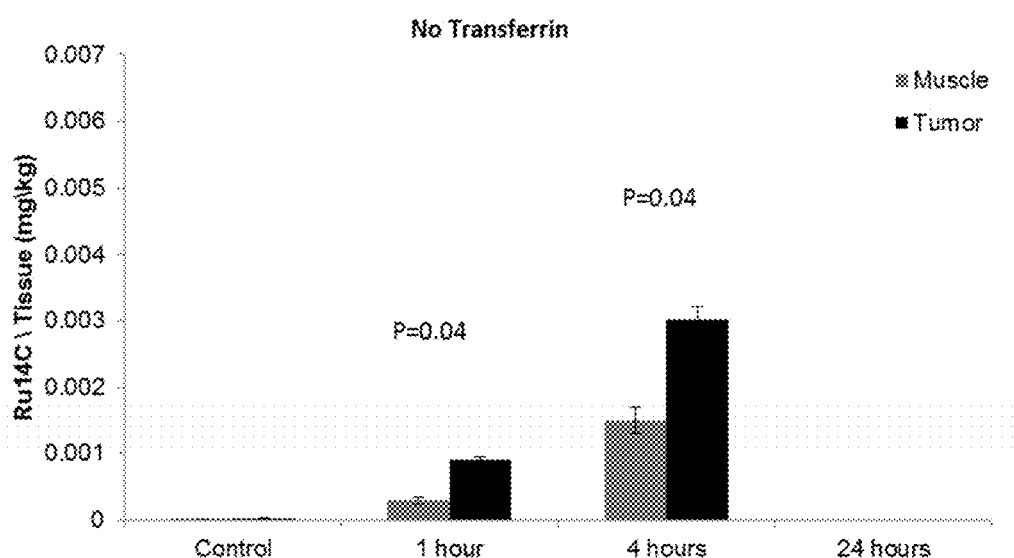
FIGS. 23A and 23B show graphs of uptake of metals over time by muscle and tumor tissue with and without transferrin.
Figure 23B:
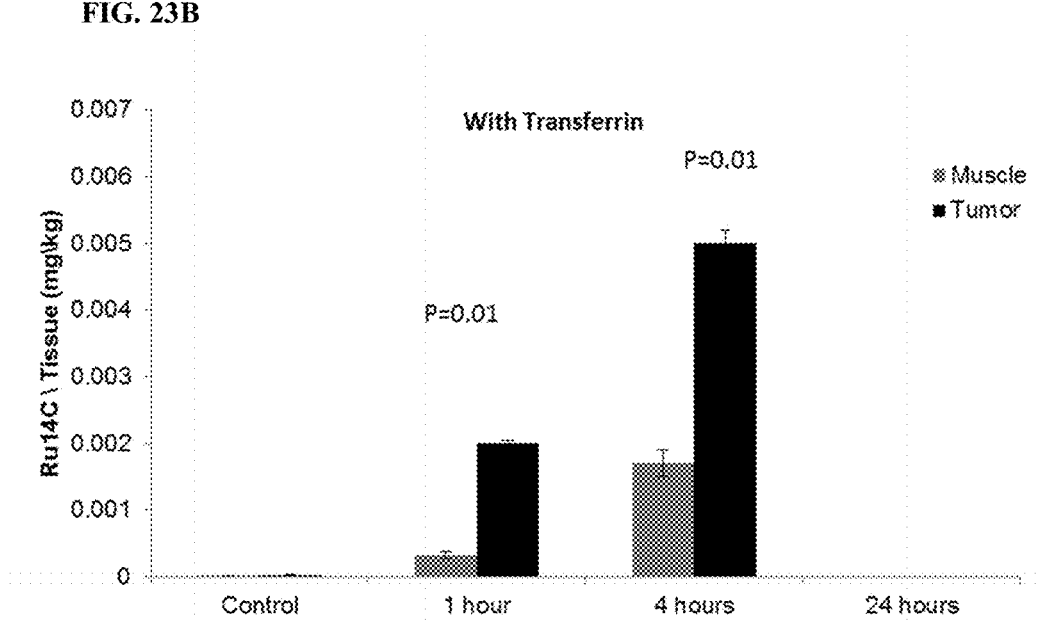

Mixing of the Ruthenium based photosensitizers (TLD1433) with transferrin (1 mg/kg) increases uptake of the photosensitizer into tissues. The presence of transferrin considerably improves selectivity of the uptake into tumors as compared to normal muscle tissue (FIGS. 23A and 23B).

Example 32 (Prophetic)

Transferrin was dissolved in 40% PG in phosphate buffer (pH=7.0)+100 mM NaCl (0.1 mg/100 uL) and added to the photosensitizer solution (to achieve 10 mg/kg dose). The mixture was incubated for 1 hour prior to injection, and 100 uL of the mixture was injected i.v. to each animal.

Figure 24A:
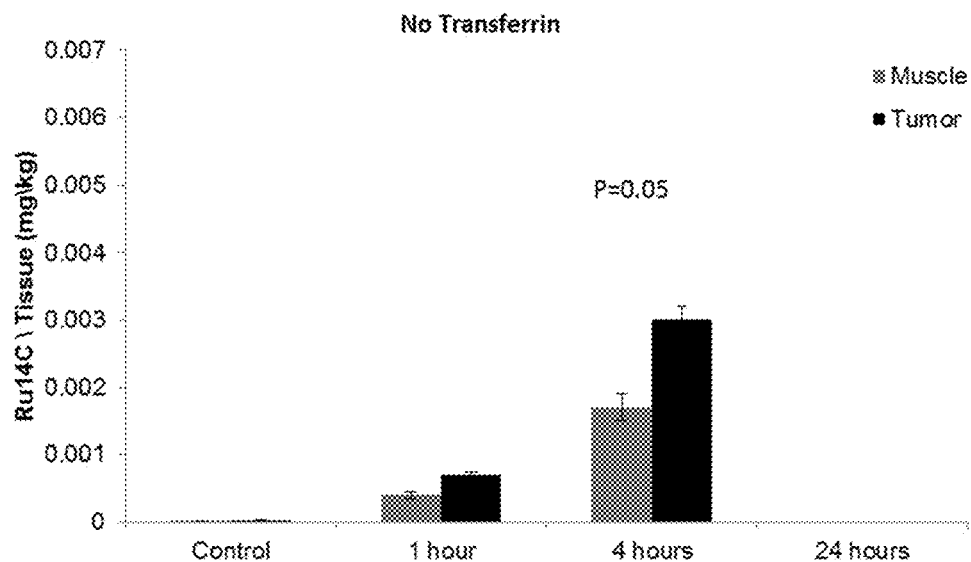
FIGS. 24A and 24B show graphs of uptake of metals over time by muscle and tumor tissue with and without transferrin.
Figure 24B:
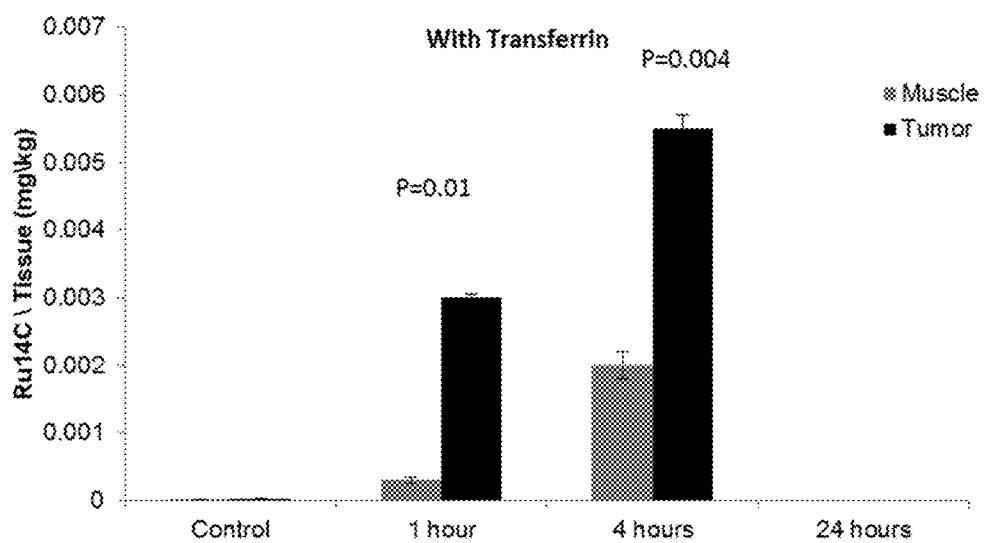

Mixing of the Ruthenium-Rhodium based photosensitizers (TLD143310) with transferrin (1 mg/kg) increases uptake of the photosensitizer into tissues. The presence of transferrin considerably improves selectivity of the uptake into tumors as compared to normal muscle tissue (FIGS. 24A and 24B).

Example 33 (Prophetic)

Transferrin was dissolved in 40% PG in phosphate buffer (pH=7.0)+100 mM NaCl (0.1 mg/100 uL) and added to the photosensitizer solution (to achieve 10 mg/kg dose). The mixture was incubated for 1 hour prior to injection, and 100 uL of the mixture was injected i.v. to each animal.

Figure 25A:
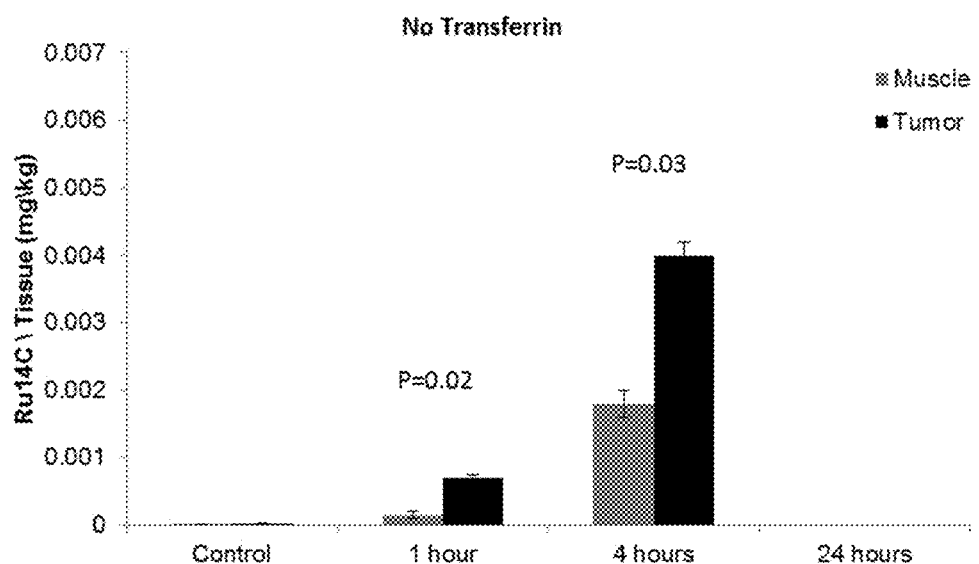
FIGS. 25A and 25B show graphs of uptake of metals over time by muscle and tumor tissue with and without transferrin.
Figure 25B:
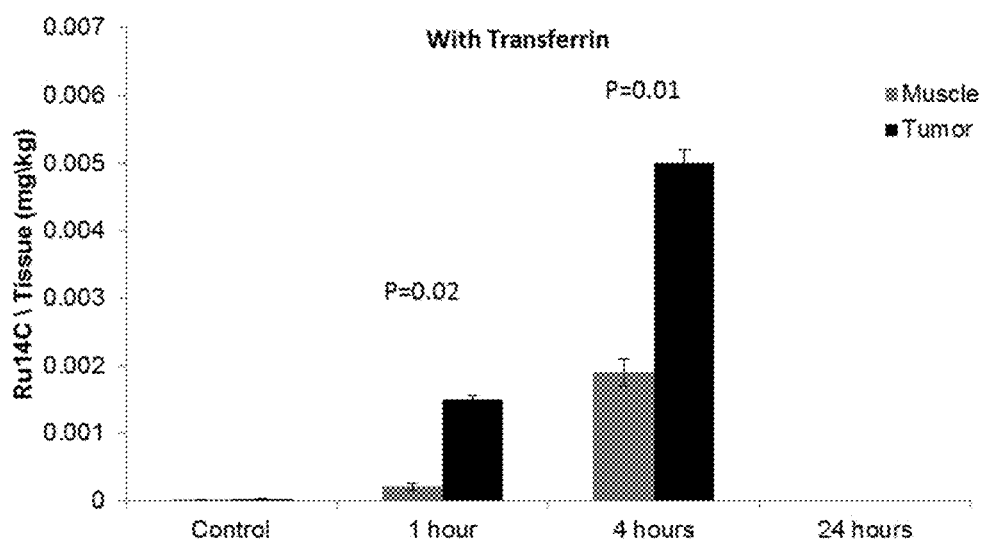
Figure 26:
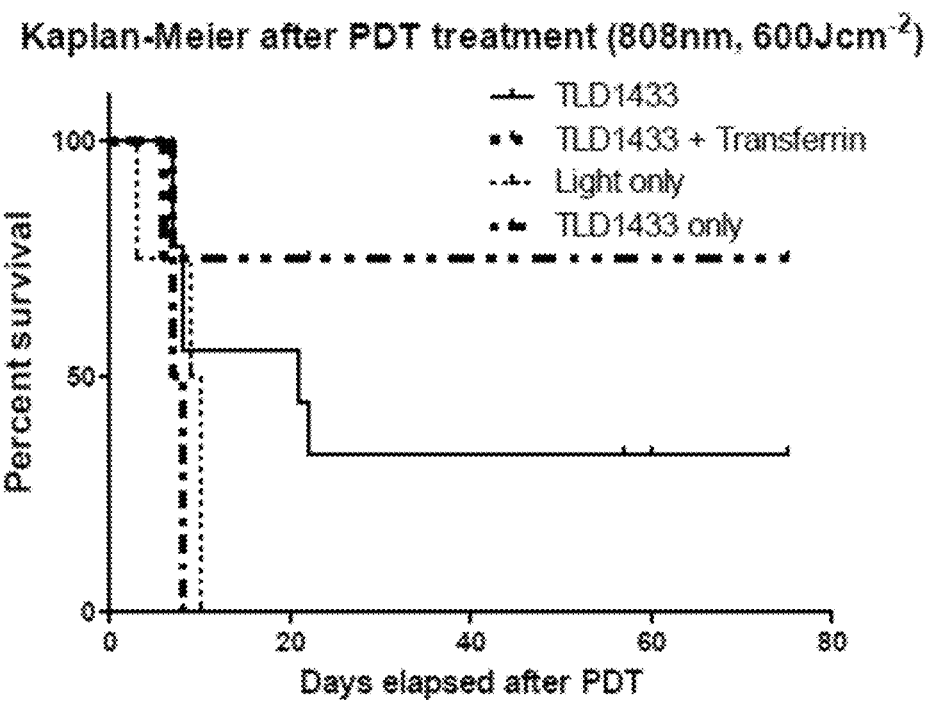
FIG. 26 shows a graph of percent survival against days elapsed after PDT.

Mixing of the Osmium based photosensitizers (TLDOsH2dppn) with transferrin (1 mg/kg) increases uptake of the photosensitizer into tissues. The presence of transferrin considerably improves selectivity of the uptake into tumors as compared to normal muscle tissue (FIGS. 25A and 25B).

Example 34

In Vivo Toxicity

Mice were injected (i.p.) with escalating doses of the photosensitizers with and without transferrin. Mixing of the photosensitizers with transferrin increased MTD which suggests a decrease in toxicity of the photosensitizers. For Ruthenium-based TLD1433, complete mouse survival was observed at 125 mg/kg; higher doses are currently being tested.

Maximum tolerated doses (MTD) of Ruthenium (TLD1433), Ruthenium-Rhodium (TLD143310) and Osmium (TLDOsH2dppn) based photosensitizers increases with transferrin are shown in Table 8 below.

TABLE 8

| Photosensitizer | MTD Dose (mg/kg) | |
| --- | --- | --- |
| | No transferrin | With transferrin (1 mg/kg) |
| TLD1433 | 100 | >125 |
| TLD143310 | 150 (Prophetic) | 200 (Prophetic) |
| TLDOsH2dppn | 50 | 100 (Prophetic) |

Considering the results of in vitro and in vivo experiments combined Ruthenium, Ruthenium-Rhodium and Osmium-based photosensitizers must be mixed with transferrin for patients treatment not only to improve PDT effect but also to decrease toxicity of the photosensitizers.

Example 35

In Vivo PDT Effect

Subcutaneous tumors were grown in mouse thighs and PDT (808 nm, 600 Jcm$^{-2}$) was performed when tumor reached 5×5 mm in size. Mice were sacrificed if tumor continued to grow after PDT treatment and reached 10×10 mm. Controls had a maximum survival of 10 days.

Transferrin increases mouse survival after PDT treatment with Ruthenium-based photosensitizer (TLD1433). The number of tumor free animals greatly increased when transferrin was added to Ruthenium-based TLD1433 before injection (in our data currently 8 days after PDT treatment, previous data has shown tumors will not reappear after this time, 70 days is assumed to remain tumor free).

Example 36 (Prophetic)

Subcutaneous tumors were grown in mouse thighs and PDT (808 nm, 600 Jcm$^{-2}$) was performed when tumor reached 5×5 mm in size. Mice were sacrificed if tumor continued to grow after PDT treatment and reached 10×10 mm. Controls had a maximum survival of 10 days.

Transferrin increases mouse survival after PDT treatment with Ruthenium-Rhodium-based photosensitizer (TLD143310) and Osmium-based (TLDOsH2dppn) photosensitizers. The number of tumor free animals greatly increased when transferrin was added to Ruthenium-Rhodium-based photosensitizer (TLD143310) and Osmium-based (TLDOsH2dppn) photosensitizers before injection. See Table 9 below.

TABLE 9

| | | Survival by day 80 | |
| --- | --- | --- | --- |
| | | Without transferrin | With transferrin |
| Mixed metal (Ruthenium-Rhodium)-based | TLD143310 | 35% (Prophetic) | 70% (Prophetic) |
| Osmium-based | TLDOsH2dppn | 40% (Prophetic) | 80% (Prophetic) |

Example 36

Subcutaneous tumors were grown in mouse thighs and PDT (635 nm, 192 Jcm$^{-2}$) was performed when tumor reached 5×5 mm in size. Mice were sacrificed if tumor continued to grow after PDT treatment and reached 10×10 mm. Controls had a maximum survival of 10 days.

Figure 27:
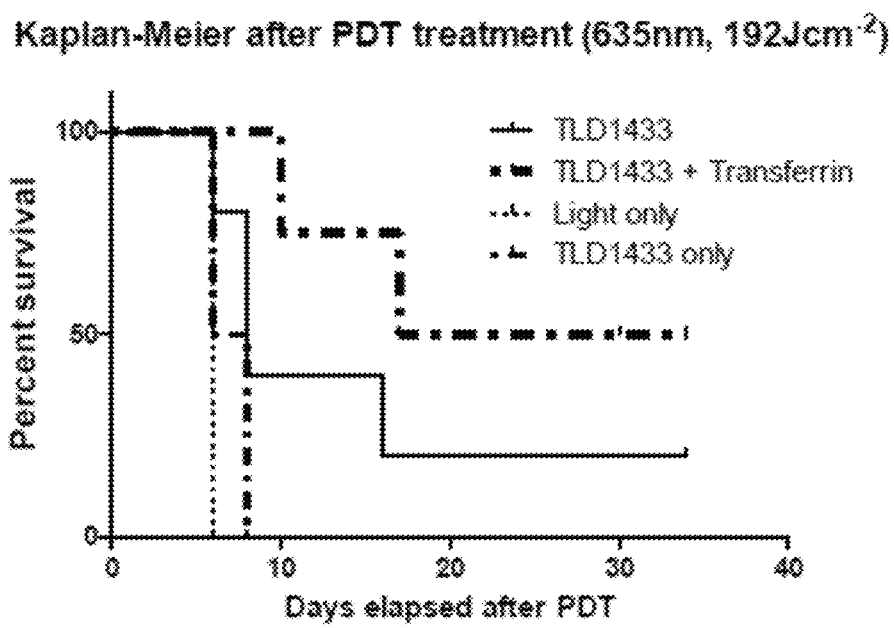
FIG. 27 shows a graph of percent survival against days elapsed after PDT.

Transferrin increases mouse survival after PDT treatment. The number of tumor free animals greatly increased when transferrin was added to TLD1433 before injection (expected results). See FIG. 27.

Example 37

Subcutaneous tumors were grown in mouse thighs and PDT (635 nm, 192 Jcm$^{-2}$) was performed when tumor reached 5×5 mm in size. Mice were sacrificed if tumor continued to grow after PDT treatment and reached 10×10 mm. Controls had a maximum survival of 10 days.

Transferrin increases mouse survival after PDT treatment with Ruthenium-Rhodium-based photosensitizer (TLD143310) and Osmium-based (TLDOsH2dppn) photosensitizers. The number of tumor free animals greatly increased when transferrin was added to Ruthenium-Rhodium-based photosensitizer (TLD143310) and Osmium-based (TLDOsH2dppn) photosensitizers before injection. See Table 10.

TABLE 10

| | | Survival by day 80 | |
| --- | --- | --- | --- |
| | | Without transferrin | With transferrin |
| Mixed metal (Ruthenium-Rhodium)-based | TLD143310 | 41% (Prophetic) | 65% (Prophetic) |
| Osmium-based | TLDOsH2dppn | 35% (Prophetic) | 75% (Prophetic) |

Example 38

Subcutaneous tumors were grown in mouse thighs and PDT (525 nm, 90 Jcm$^{-2}$) was performed when tumor reached 5×5 mm in size. Mice were sacrificed if tumor continued to grow after PDT treatment and reached 10×10 mm. Controls had a maximum survival of 10 days.

Transferrin increases mouse survival after PDT treatment with Ruthenium-Rhodium-based photosensitizer (TLD143310) and Osmium-based (TLDOsH2dppn) photosensitizers. The number of tumor free animals greatly increased when transferrin was added to Ruthenium-Rhodium-based photosensitizer (TLD143310) and Osmium-based (TLDOsH2dppn) photosensitizers before injection. See Table 11.

TABLE 11

| | | Survival by day 80 | |
| --- | --- | --- | --- |
| | | Without transferrin | With transferrin |
| Mixed metal (Ruthenium-Rhodium)-based | TLD143310 | 48% (Prophetic) | 85% (Prophetic) |
| Osmium-based | TLDOsH2dppn | 37% (Prophetic) | 78% (Prophetic) |

Example 39

Figure 28:
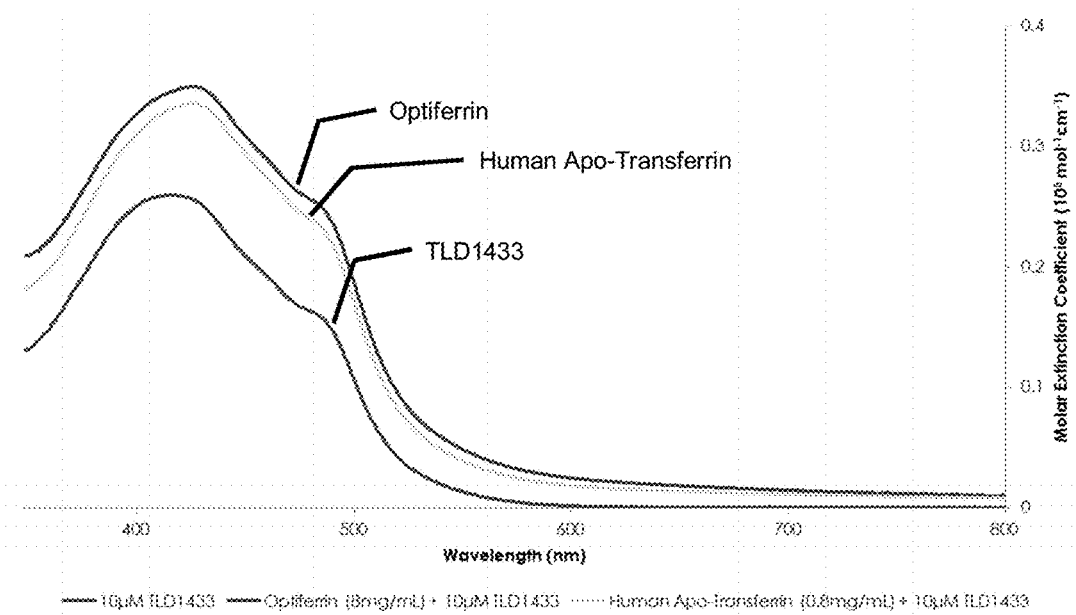
FIG. 28 shows a graph of molar extinction coefficient against wavelength.

The optical density of TLD1433 was measured before and after the addition of either OPTIFERRIN (available from InVitria, a division of Ventria Bioscience) or human apo-transferrin (Sigma). As shown in FIG. 28, the TLD1433-OPTIFERRIN complex showed a substantial increase in optical density. Furthermore, the complex showed novel absorption in the red (600 nm) and near infrared (800 nm) wavelengths. The optical density of the OPTIFERRIN complex was comparable to that of the human apo-transferrin complex. This finding highlights the potential of using OPTIFERRIN to increase the efficacy of Theralase's TLD1433 photosensitizer. The increase in optical density will translate to a higher production of reactive oxygen species during PDT treatment. The absorption in red and near infrared light will allow for novel treatment applications for different tumors.

Example 40

Figure 29:
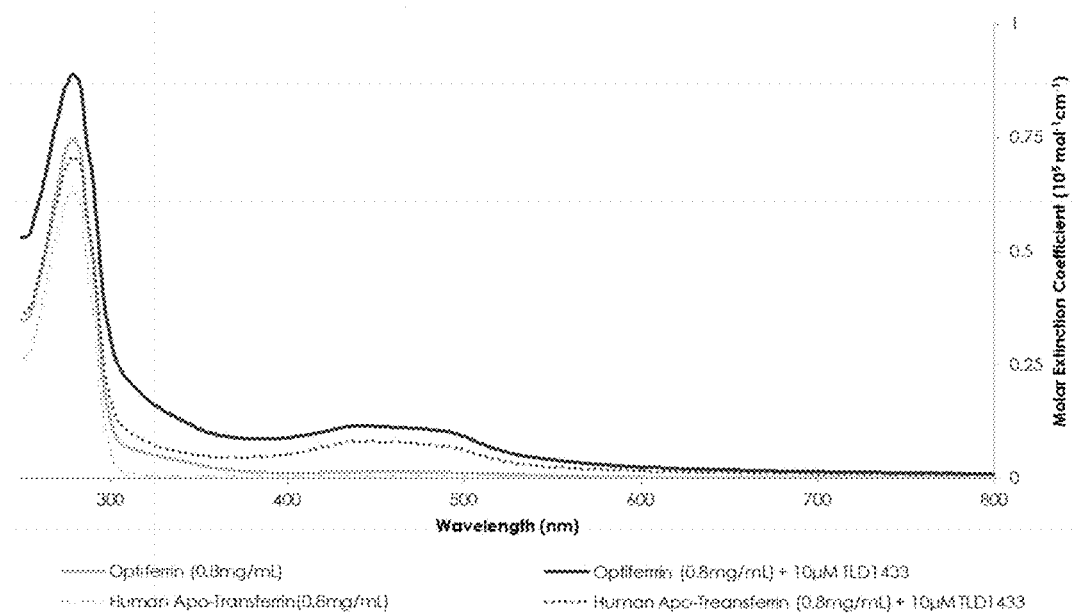
FIG. 29 shows a graph of molar extinction coefficient against wavelength.

The optical density of Optiferrin and human apo-transferrin was measured before and after TLD1433 addition. Transferrin binding to iron is characterized by an increase in absorption at 275 nm and 450 nm. Much like human apo-transferrin, Optiferrin shows this characteristic optical density increase after TLD1433 addition, showing direct binding of TLD1433 to Optiferrin. See FIG. 29. Direct binding of Optiferrin to TLD1433 can be utilized in the treatment of transferrin receptor rich tumors, where the Optiferrin+TLD1433 complex can be administered to achieve preferential uptake of TLD1433 in cancer cells.

Example 41

Figure 30:
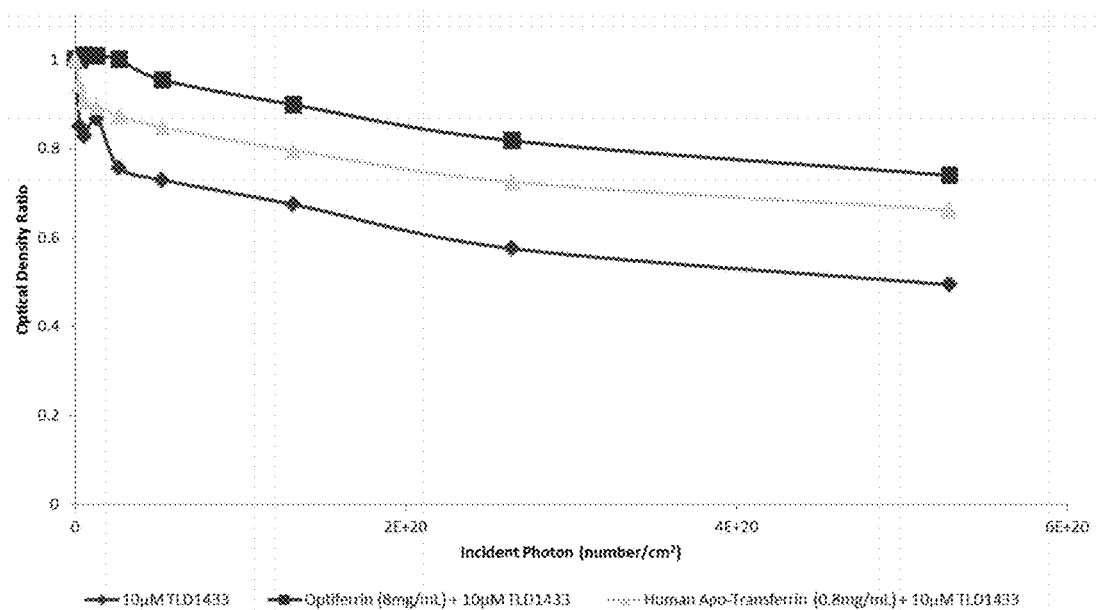
FIG. 30 shows a graph of optical density ratio against incident photon number.

The bleaching of TLD1433 alone and incubated with Optiferrin or human apo-transferrin in response to 525 nm (green) light was measured. Bleaching was measured by the decrease in the optical density at 425 nm in response to irradiation to 525 nm light, which was normalized by dividing it by the 425 nm optical density of the unexposed sample. Optical density ratio of 1 signifies no bleaching. Bleaching of TLD1433 results in the ratio decreasing towards 0. Both Optiferrin and human apo-transferrin reduced the bleaching of TLD1433, with Optiferrin having a stronger effect. See FIG. 30.

Example 42

Optiferrin Binding with TLD1433 (14C TH2, GS6-22, and GS6-81G) and TH1 (Sky Blue)

Figure 31:
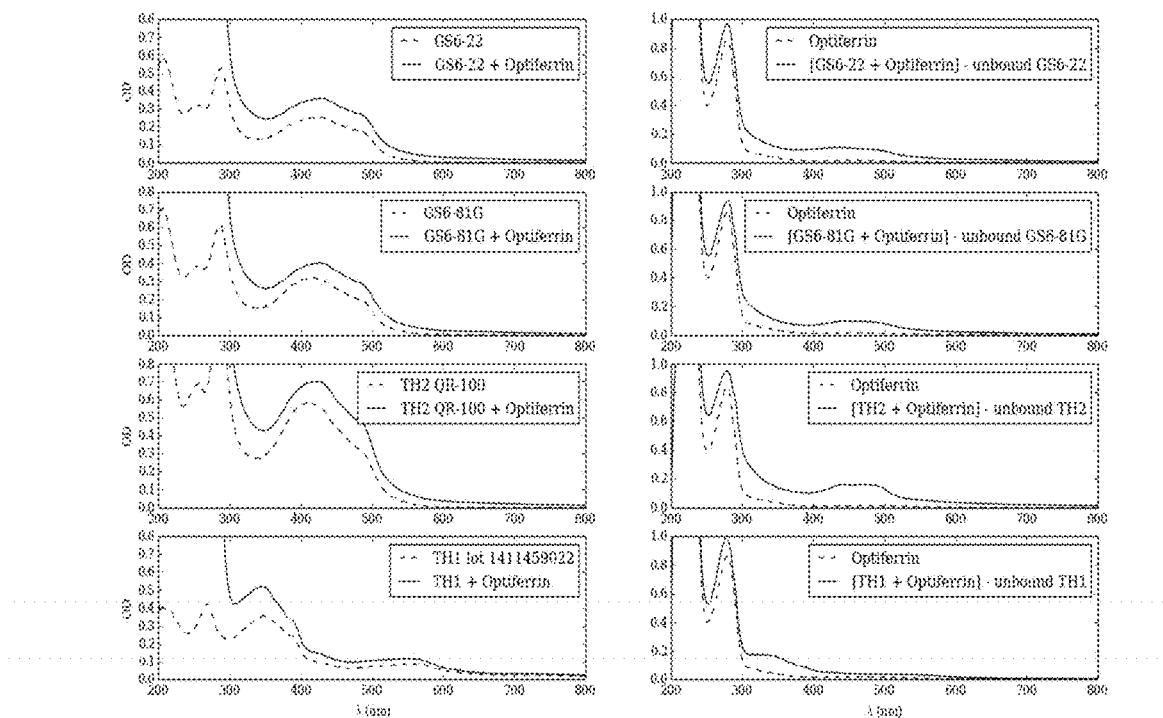
FIG. 31 shows graphs of optical density against wavelength.

Experiments demonstrated that the following photosensitizers mimic the binding signatures of Fe+Tf binding, but with Optiferrin: TLD1433 GS6-22, GS6-81G, TH2 QR-100, and TH1 lot no. 1411459022. See FIG. 31.

Example 43

Photobleaching Prevention Over 200 J with TLD1433

Figure 32:
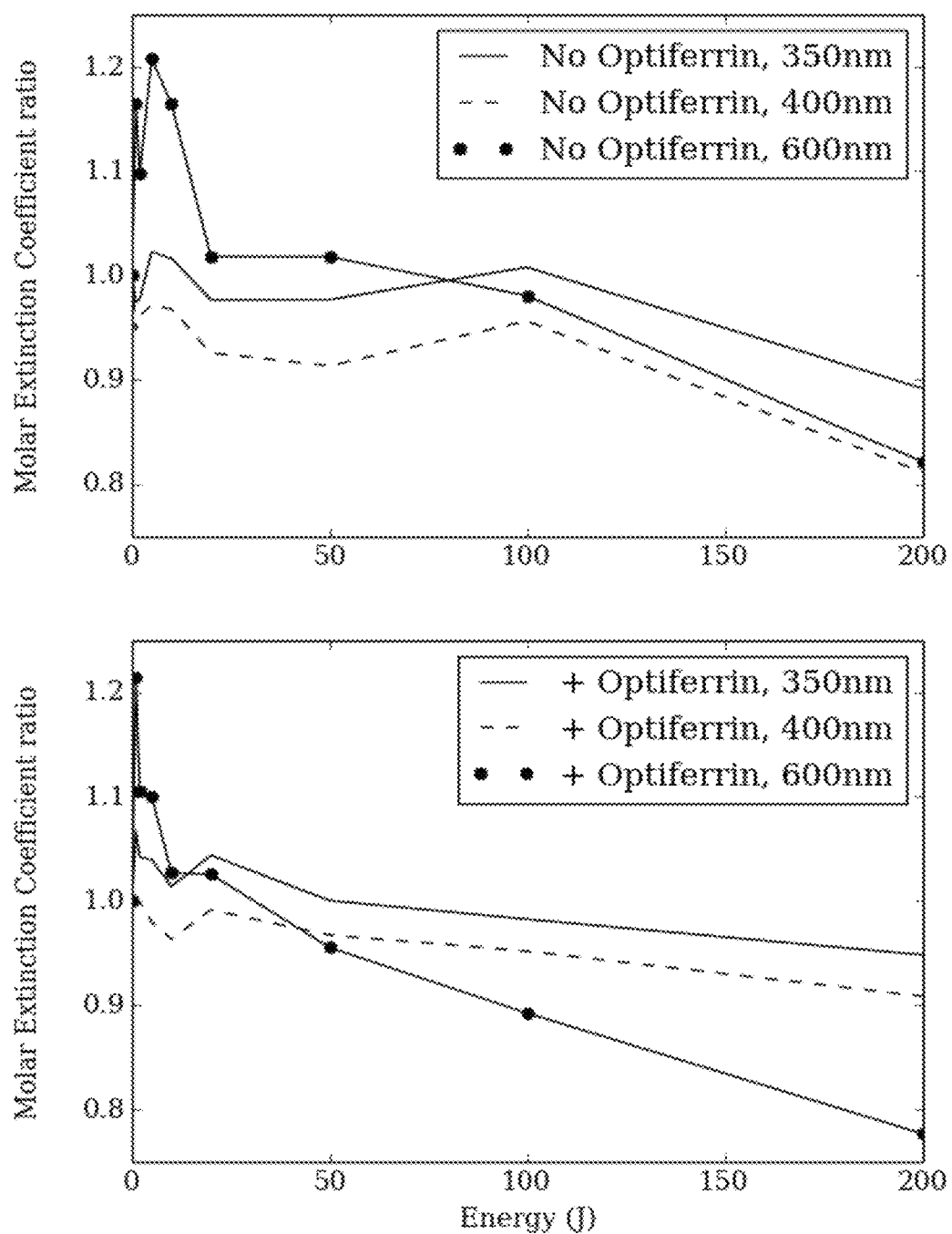
FIG. 32 shows graphs of molar extinction coefficient ratio against energy.

10 uM TLD1433 GS6-22 was photobleached with 200 J of green light (525 nm) and its OD was measured at 0, 1, 2, 5, 10, 20, 50, 100, and 200 Joules. See FIG. 32, which shows the ratio of Molar Extinction Coefficient increase or decrease at 350 nm, 400 nm, and 600 nm between the initial time with 0 Joules, and the final time with 200 Joules.

Example 44

TLD1433 Infrared Absorbance Stability

Figure 33:
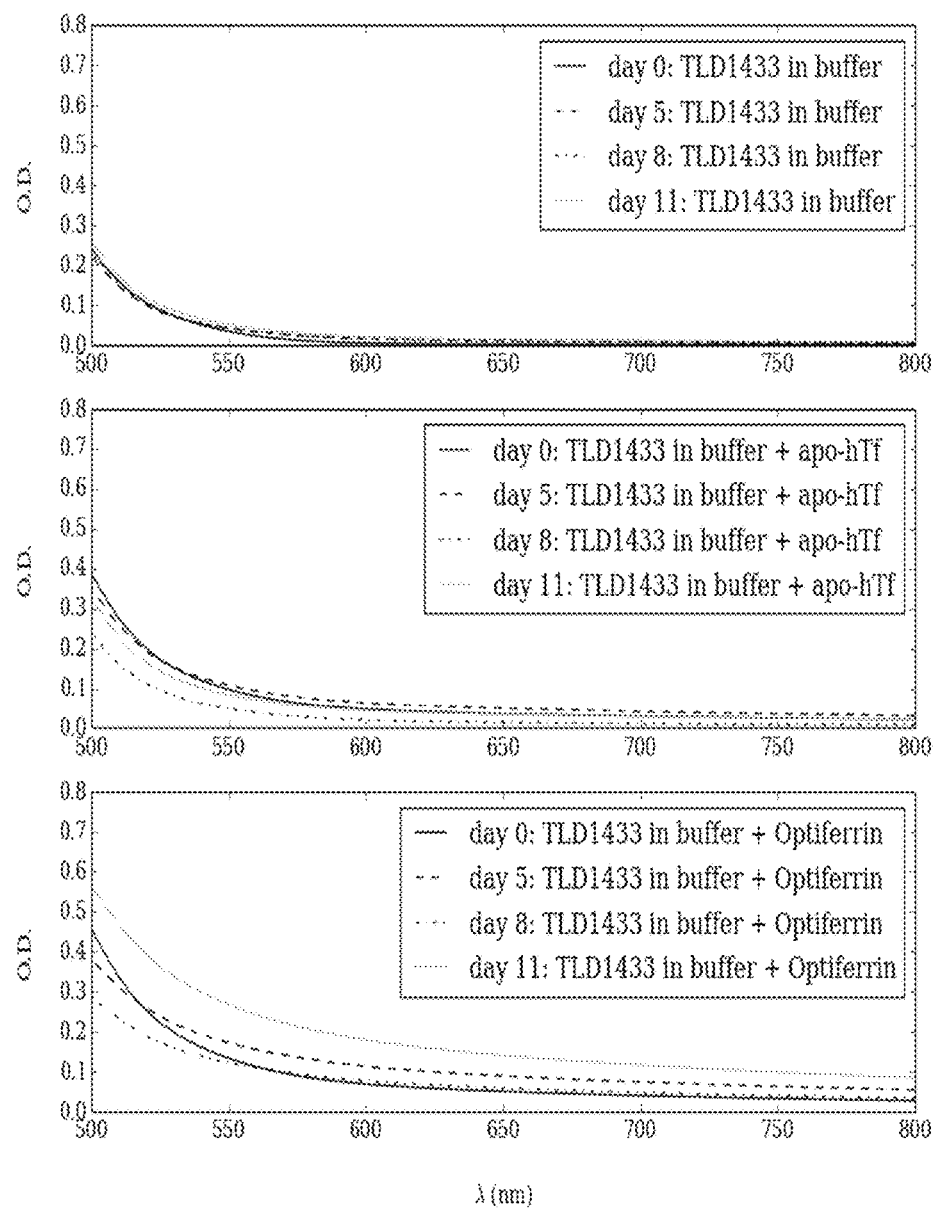
FIG. 33 shows graphs of optical density against wavelength.

Experiments demonstrated that the OD of TLD1433 is better maintained in the infrared with the addition of 0.8 g/L (or 10 uM) Optiferrin over time. See FIG. 33.

Example 45

Optiferrin Incubation and the Maintenance of Photosensitiser TLD1433 Absorbance

Figure 34:
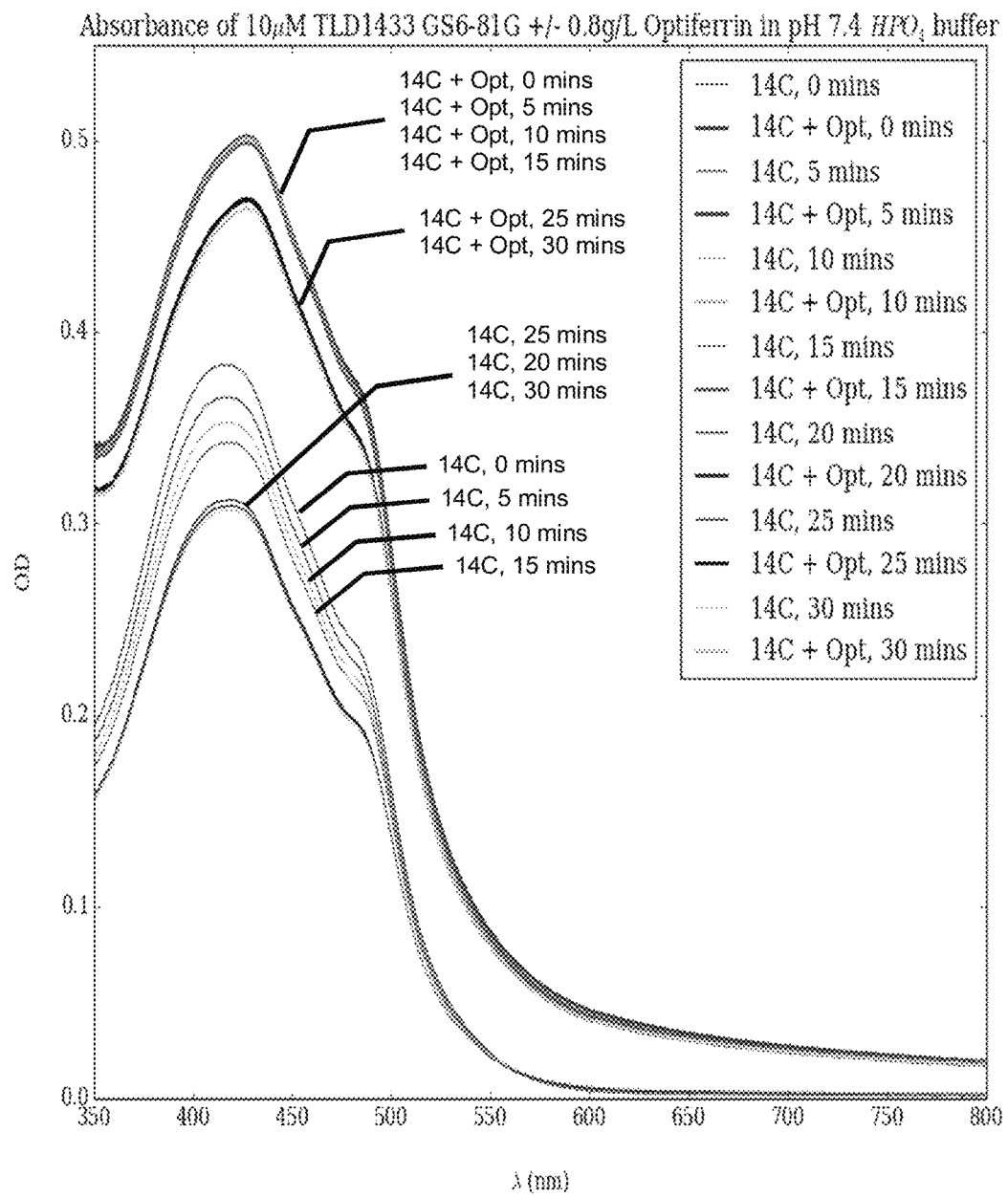
FIG. 34 shows graphs of optical density against wavelength.

The incubation duration was examined to see how well a dark sample of 10 uM TLD1433 would absorb with the addition of Optiferrin. See FIG. 34. As seen previously this undoubtedly helps prevent TLD1433 from photobleaching.

Example 46

In Vivo PDT in Rat Glioblastoma

A four-month old rat was injected in the cerebral cortex with 5000 RG2 cells (rat glioblastoma tumor model). Eleven days later, the rat was injected with TLD1433 (5 mg/kg) with human apo-transferrin. The structure of TLD1433 is shown below:

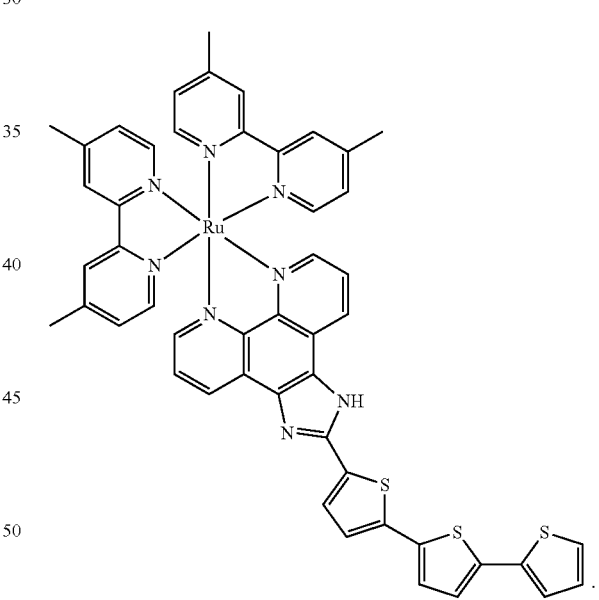

PDT was administered 24 hours later. Light source and fluence: 808 nm wavelength, 300 J/cm$^2$ delivered at 100 mW. The number of photons absorbed was $2.8 \times 10^{17}$ photons/cm$^3$. The rat survived 13 days post PDT treatment.

Figure 35A:
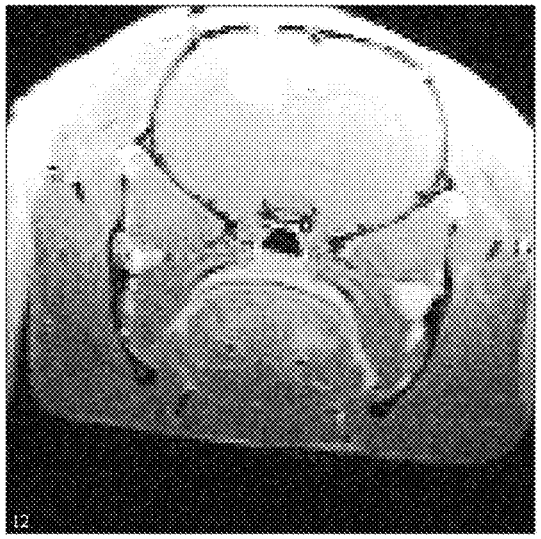
FIGS. 35A, 35B, 35C, 35D, 35E, 35F, 35G and 35H are Magnetic Resonance Images (MRIs) of the brain of a rat treated in accordance with an embodiment of the invention.
Figure 35B:
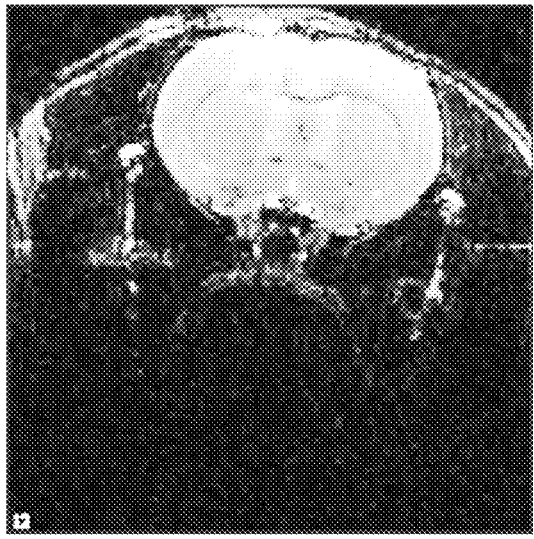
Figure 35C:
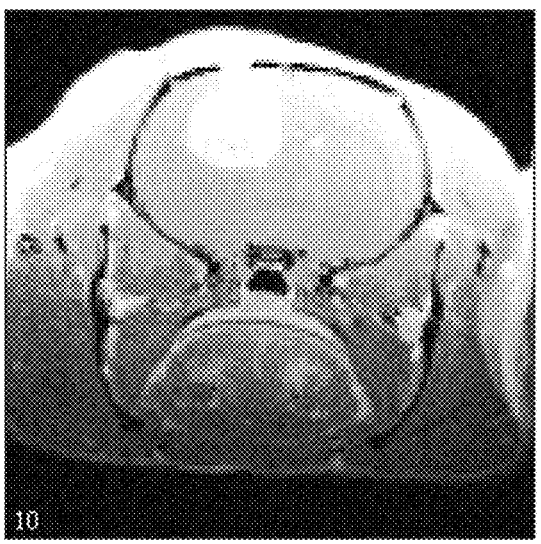
Figure 35D:
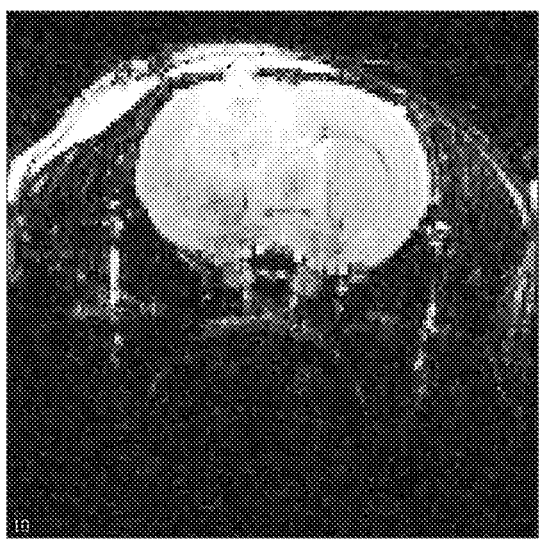
Figure 35E:
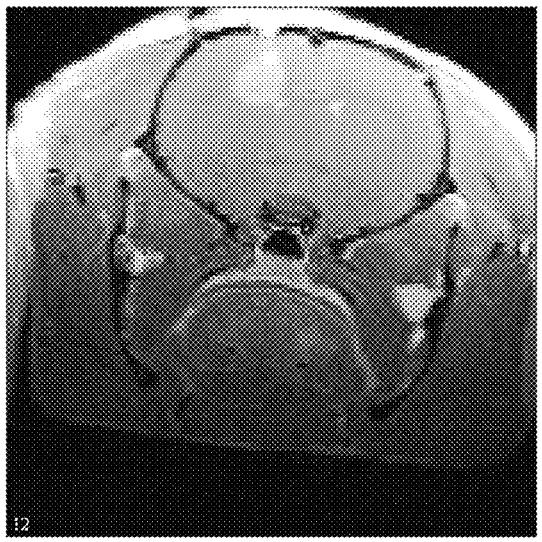
Figure 35F:
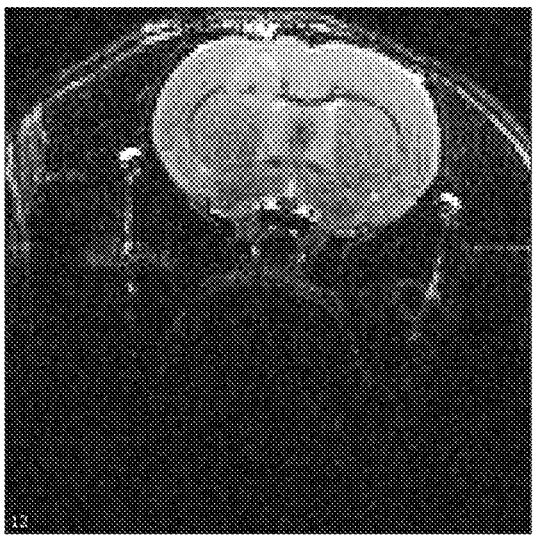
Figure 35G:
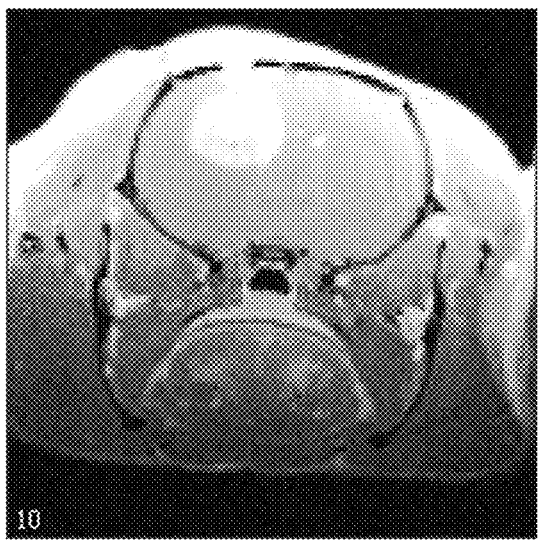
Figure 35H:
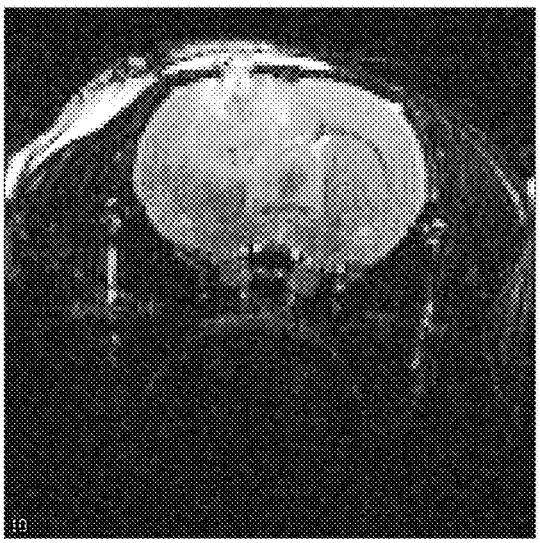

The effect of PDT on tumor size is shown in FIGS. 35A-H. FIG. 35A is a T1 weighted MRI and FIG. 35B is a T2 weighted MRI of the rat 6 days after tumor cell injection. FIG. 35C is a T1 weighted MRI and FIG. 35D is a T2 weighted MRI of the rat 10 days after tumor cell injection. FIG. 35E is a T1 weighted MRI and FIG. 35F is a T2 weighted MRI of the rat 3 days after PDT. FIG. 35G is a T1 weighted MRI and FIG. 35H is a T2 weighted MRI of the rat 8 days after PDT.

Example 47

In Vivo PDT in Rat Glioblastoma

A five-month old rat was injected in the cerebral cortex with 5000 RG2 cells. Eleven days later, the rat was injected with TLD1433 (5 mg/kg) with human apo-transferrin. PDT was administered 24 hours later. Light source and fluence: 808 nm wavelength, 600 J/cm$^2$ delivered at 200 mW. The number of photons absorbed was $4.41 \times 10^{18}$ photons/cm$^3$. The rat has not died. At the time of the drafting of this text, the rat had survived 25 days post PDT treatment. We did not notice any behavioral or cognitive changes in the PDT treated rats of Examples 46 or 47.

The example demonstrates a significant survival benefit compared to 8 days post PDT survival with aminolevulinic acid (ALA) mediated PDT in this aggressive tumor model. It is a very aggressive tumor model because survival of untreated controls is only 4 days.

Figure 36E:
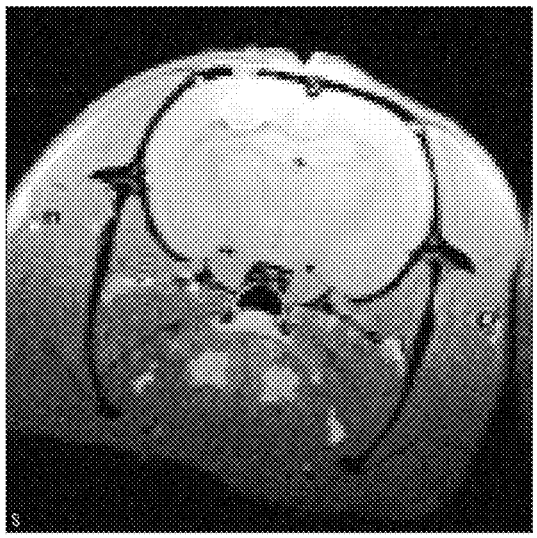

The effect of PDT on tumor size is shown in FIGS. 36A-J. FIG. 36A is a T1 weighted MRI and FIG. 36B is a T2 weighted MRI of the rat 8 days after tumor cell injection. The tumor shown in these figures measured about 0.84 mm in diameter.

FIG. 36C is a T1 weighted MRI and FIG. 36D is a T2 weighted MRI of the rat 10 days after tumor cell injection. The tumor shown in these figures measured about 1.44 mm in diameter.

Figure 36F:

FIG. 36E is a T1 weighted MRI and FIG. 36F is a T2 weighted MRI of the rat 3 days after PDT. It is difficult to measure the size of tumor 3 days post PDT, as these images show extensive inflammatory response to treatment depicted by edema.

Figure 36G:
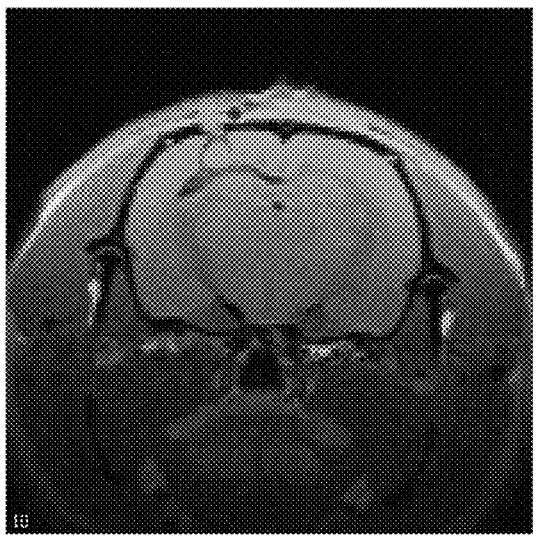
Figure 36H:
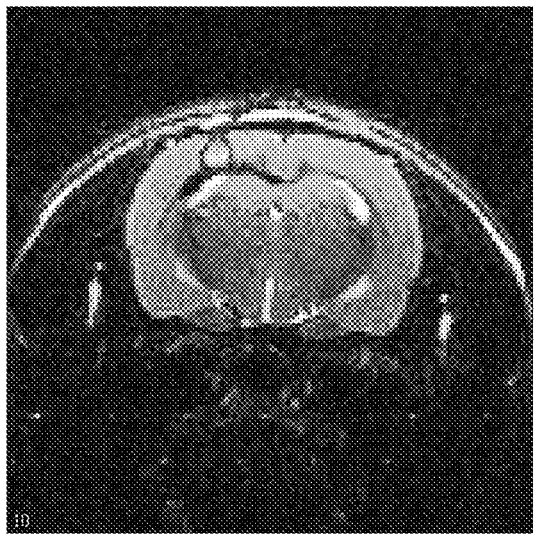

FIG. 36G is a T1 weighted MRI and FIG. 36H is a T2 weighted MRI of the rat 10 days after PDT. FIG. 36I is a T1 weighted MRI and FIG. 36J is a T2 weighted MRI of the rat 20 days after PDT. There no tumor detectable by MRI imaging. No tissue is taking up contrast agent, suggesting complete destruction of the tumor.

Example 48

ICP-MS Studies

Inductively coupled plasma mass spectrometry (ICP-MS) was performed to acquire data showing the selective uptake of drug by tumor tissue.

Tumor tissue was collected based on tumor location seen by MRI image. As a normal tissue control, samples were collected from the same location within the contralateral brain hemisphere. As a control tissue other than cerebral cortex, we also collected cerebellum to evaluate the safety of our therapy.

FIG. 37 shows the results of ICP-MS performed 24 hours after administration to a rat of TLD1433 (5 mg/kg body weight) with human Apo-transferrin.

Figure 38:
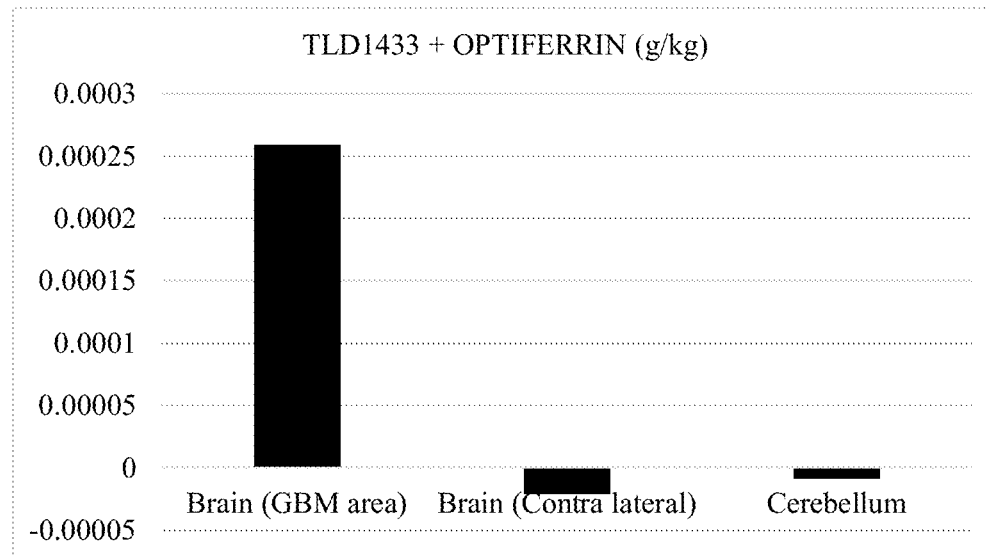

FIG. 38 shows the results of ICP-MS performed 4 hours after administration to a first rat of TLD1433 (5 mg/kg body weight) with OPTIFERRIN.

Figure 39:
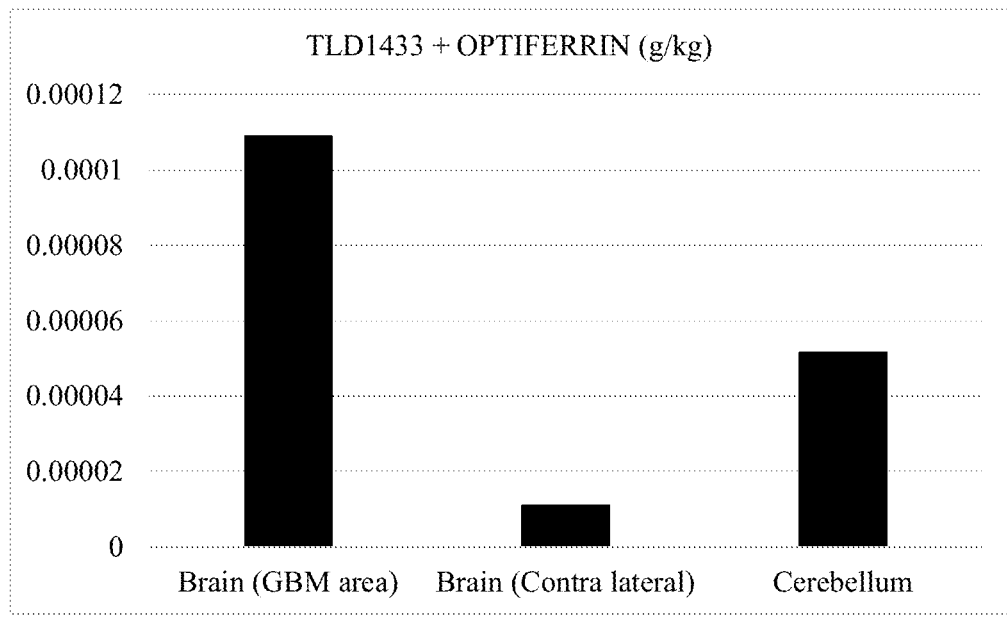

FIG. 39 shows the results of ICP-MS performed 24 hours after administration to a second rat of TLD1433 (5 mg/kg body weight) with OPTIFERRIN.

The data show that the PDC (TLD1433) is actively taken-up by tumor tissue through the transferrin receptor. FIG. 37 shows that uptake of the PDC was 15.7 times higher in tumor tissue than in healthy tissue when it was injected as a mixture with human-Apo transferrin. Similar selective uptake was shown with Optiferrin (FIGS. 38 and 39).

Selectivity of PDT is provided by the pharmacokinetics of the photosensitizers, leading to a local differential accumulation and retention in GBM tumor tissue versus normal intracranial tissues to provide PDT specificity to tumor tissue. The data show that the PDC has a good pharmacokinetic profile with a significantly higher concentration of drug in tumor compared to normal tissue at 4 hrs and 24 hrs post drug injection. It is expected that this effect will persist over longer durations.

Example 49

In Vitro PDT with TLD1433

A PRESTOBLUE method was performed to evaluate LD50 of TLD1433+apo-transferrin on RG2 cells. On Day 1, cells were prepared in 96-well plates in complete DMEM with phenol red: 15,000 RG2 cells/well in 200 µl media. Two plates were prepared—one for dark toxicity and one for 530 nm green 20 J PDT.

The plates were placed in a tissue culture incubator overnight.

On Day 2, drug dilutions of 0, 10, 25, 50, 75, 100, 200, 300, 400, 500 were prepared. Media were removed from plates and washed with 100 µl of media with no phenol red and sodium pyruvate. 100 µl of drug dilutions were added to respective wells and incubated for 1 hour in tissue culture incubator. After 1 hour, the plates were washed once and refilled with 100 µl fresh media. Then PDT was performed with a green laser head (#00346), 20 J/cm$^2$=56 seconds. Later plates were returned to incubator for overnight.

On Day 3, PRESTOBLUE was prepared (1/10) in media without phenol red or sodium pyruvate. 100 µl PRESTOBLUE was added to each well and the plates were read at 570/600 nm with 590 nm cut-off.

Figure 40:
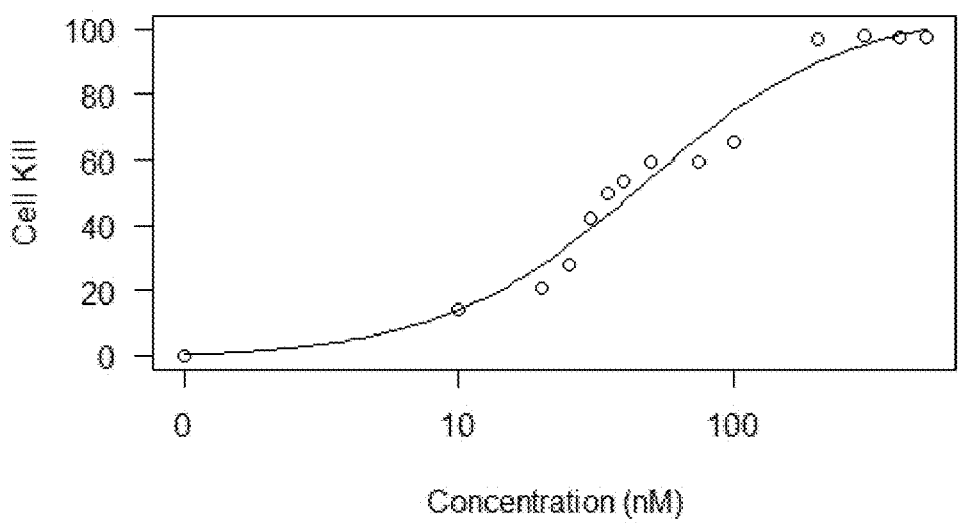
FIG. 40 shows a graph of in vitro cell kill vs. concentration.
Figure 41A:
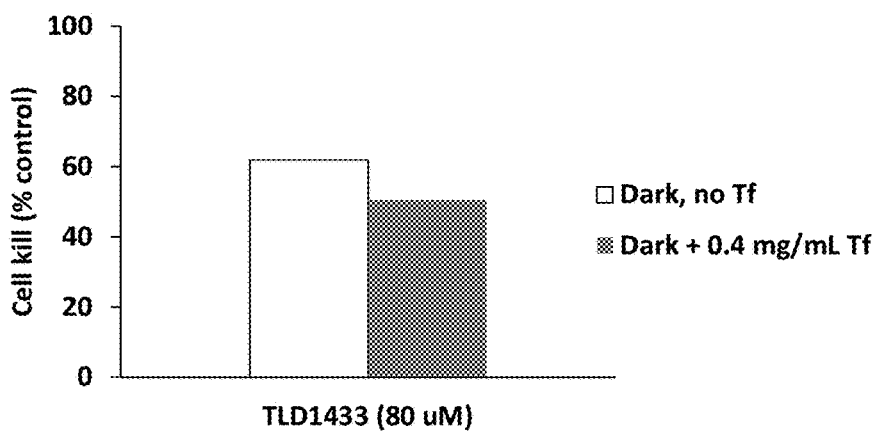
FIG. 41A is a bar chart showing in vitro cell kill by TLD1433 with and without transferrin, wherein the TLD1433 was not photodynamically activated.
Figure 41B:
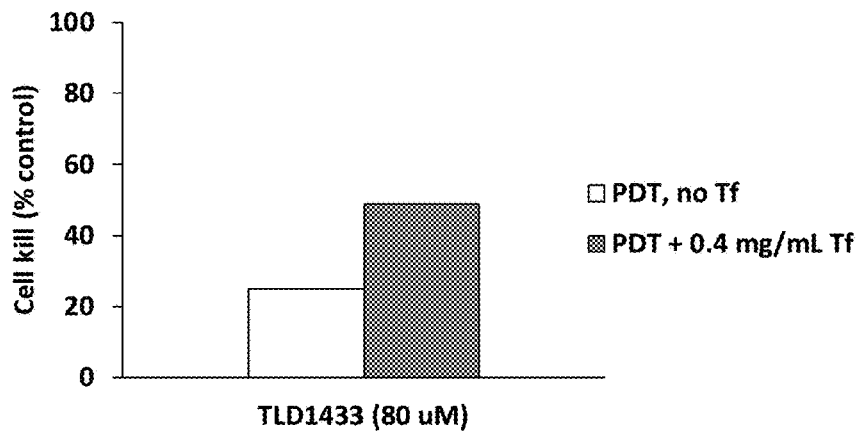
FIG. 41B is a bar chart showing in vitro cell kill by TLD1433 with and without transferrin, wherein the TLD1433 was photodynamically activated.
Figure 41C:
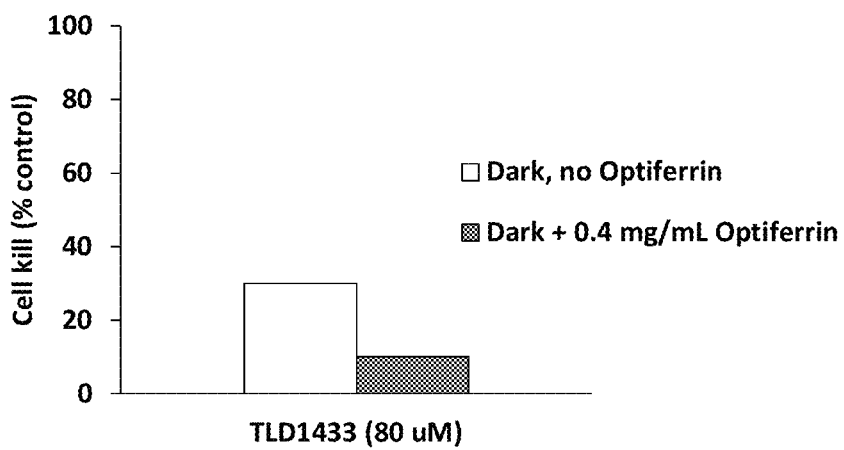
FIG. 41C is a bar chart showing in vitro cell kill by TLD1433 with and without OPTIFERRIN, wherein the TLD1433 was not photodynamically activated.
Figure 41D:
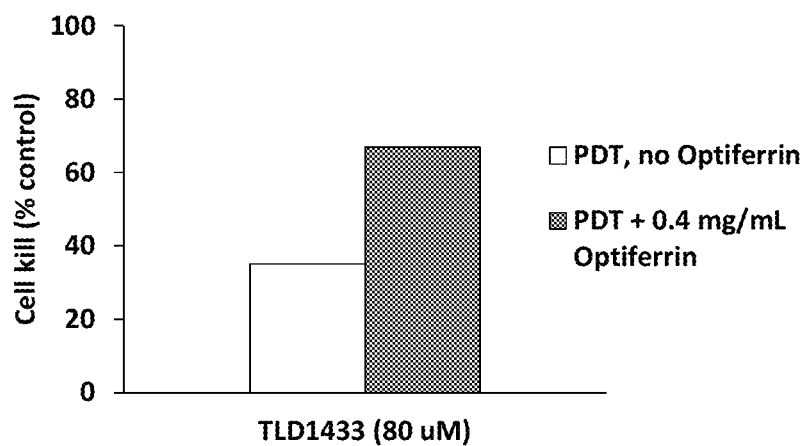
FIG. 41D is a bar chart showing in vitro cell kill by TLD1433 with and without OPTIFERRIN, wherein the TLD1433 was photodynamically activated.
Figure 42A:
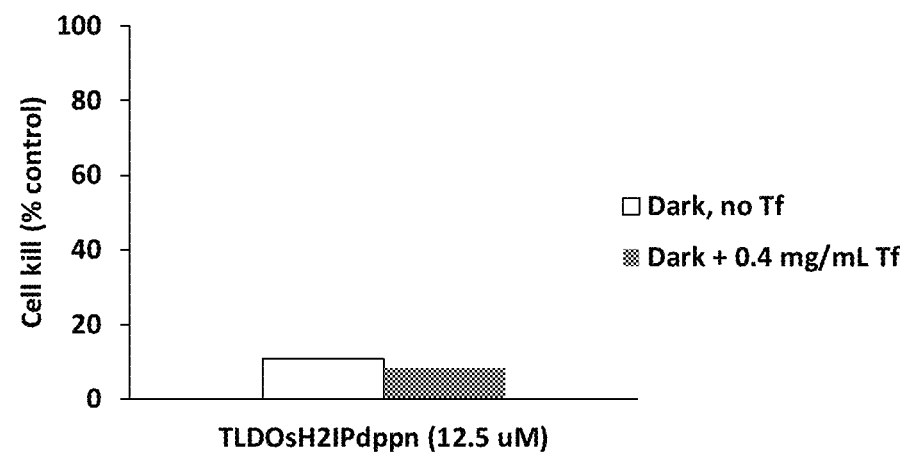
FIG. 42A is a bar chart showing in vitro cell kill by TLDOSH2DPPN with and without transferrin, wherein the TLDOSH2DPPN was not photodynamically activated.
Figure 42B:
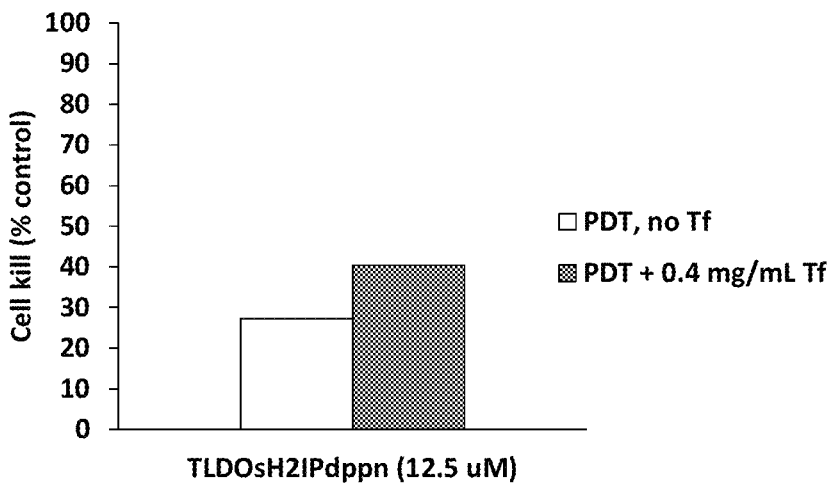
FIG. 42B is a bar chart showing in vitro cell kill by TLDOSH2DPPN with and without transferrin, wherein the TLDOSH2DPPN was photodynamically activated.
Figure 42C:
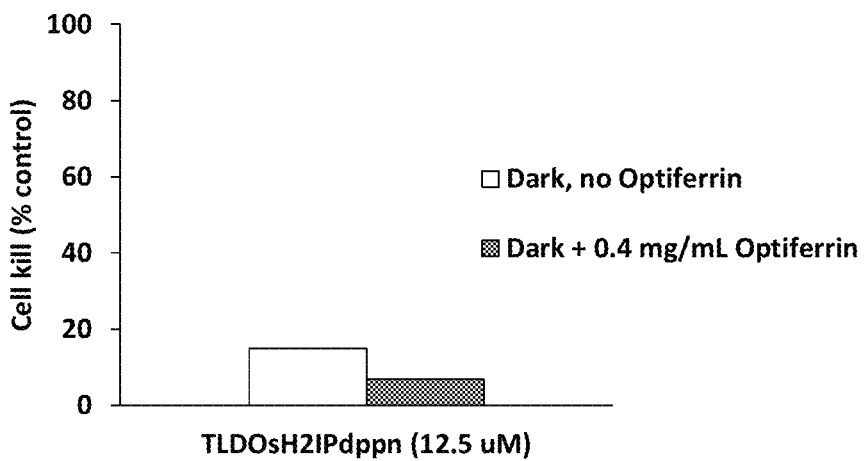
FIG. 42C is a bar chart showing in vitro cell kill by TLDOSH2DPPN with and without OPTIFERRIN, wherein the TLDOSH2DPPN was not photodynamically activated.
Figure 42D:
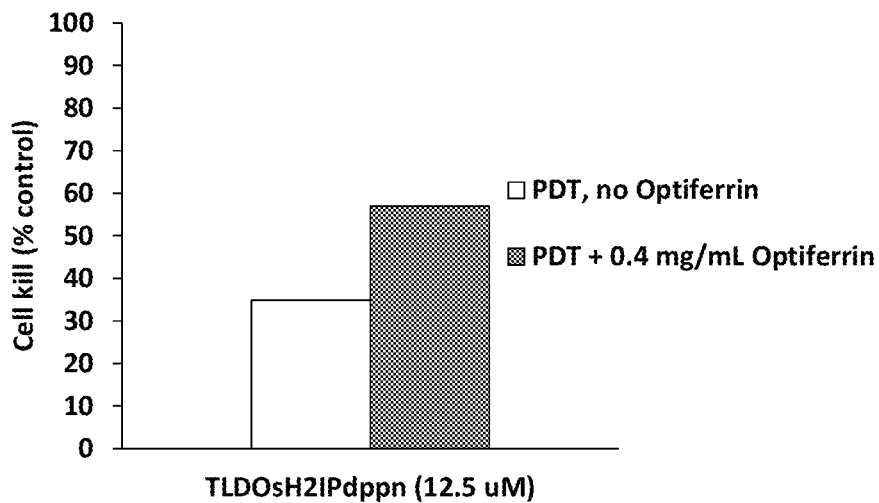
FIG. 42D is a bar chart showing in vitro cell kill by TLDOSH2DPPN with and without OPTIFERRIN, wherein the TLDOSH2DPPN was photodynamically activated.

FIG. 40 is a graph showing LD50 calculations for TLD1433 mediated PDT of RG2 cells. The LD50 was 47.34791+−9.06154 nM.

These results suggest that RG2 cells are highly sensitive to TLD1433 mediated PDT.

Example 50

In Vitro PDT with TLD1433 and TLDOsH2IPdppn

Human glioblastoma (U87) cells were incubated in the presence of ruthenium-based (TLD1433) or osmium-based (TLDOsH2IPdppn, shown below):

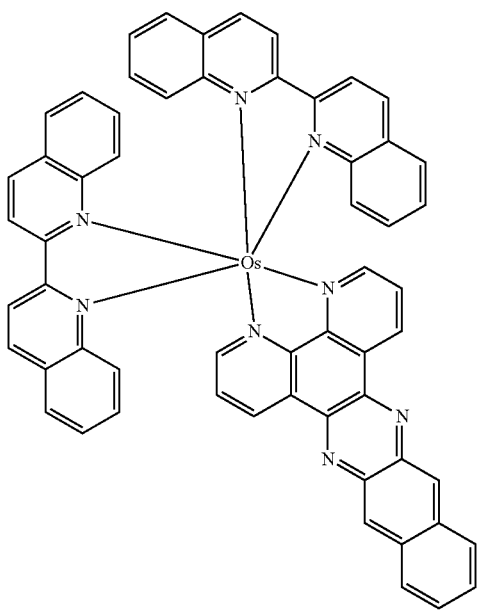

photosensitizer without or with 0.4 mg/mL human apo-transferrin or optiferrin for 2 hours at 37° C. If no transferrin or optiferrin was added, an equivalent volume of medium was added instead.

After that, the medium was replaced with a fresh one (without photosensitizer and transferrin/optiferrin). For PDT, the cells were irradiated (635 nm, 90 J/cm² for TLD1433 and 808 nm, 600 J/cm² for TLDOsH2IPdppn).

On the next day (21 hours post-irradiation), viability of the cells was measured using a PRESTOBLUE viability assay, and the percent of cell kill was calculated. The PDT effect shown is a result of subtraction of "photosensitizer alone" and "light alone" cell kill from the total PDT cell kill.

As shown in FIGS. 41A-41D and 42A-42D, the presence of transferrin/optiferrin decreases dark toxicity (photosensitizer alone) and increases the PDT effect of the photosensitizers.

This allows for safer PDT treatment in the presence of transferrin/optiferrin due to shorter treatment time and the use of lower concentrations of the photosensitizers.

It is anticipated that similarly effective results will be achieved with respect to other types of tumor cells, such as retinoblastoma cells.

While the invention has been described in detail and with reference to specific examples thereof, it will be apparent to one skilled in the art that various changes and modifications can be made therein without departing from the spirit and scope thereof.

NON-PATENT REFERENCES

Antonarakis E. S., Emadi A. Ruthenium-based chemotherapeutics: are they ready for prime time? Cancer Chemother Pharmacol. 2010 May; 66(1):1-9.

Bergamo A., Sava G. Ruthenium anticancer compounds: myths and realities of the emerging metal-based drugs. Dalton Trans. 2011 Aug. 21; 40(31):7817-23.

Biju V. Chemical modifications and bioconjugate reactions of nanomaterials for sensing, imaging, drug delivery and therapy. Chem Soc Rev. 2014 Feb. 7; 43(3):744-64. doi: 10.1039/c3cs60273g.

Bruijnincx P. C. A., Sadler P. J. (2009). "Controlling platinum, ruthenium, and osmium reactivity for anticancer drug design". Advances in Inorganic Chemistry 61. p. 1

Chen H., Xiao L., Anraku Y., Mi P., Liu X., Cabral H., Inoue A., Nomoto T., Kishimura A., Nishiyama N., Kataoka K. Polyion complex vesicles for photoinduced intracellular delivery of amphiphilic photosensitizer. J Am Chem Soc. 2014, 136(1):157-63. doi: 10.1021/ja406992w. Epub 2013 Dec. 26.

Derycke A. S., Kamuhabwa A., Gijsens A., Roskams T., De Vos D., Kasran A., Huwyler J., Missiaen L., de Witte P. A., 2004. Transferrin-conjugated liposome targeting of photosensitizer AlPcS4 to rat bladder carcinoma cells. J. Natl Cancer Inst. 96, 1620-1630.

Garcia P. F., Toneatto J., Silvero M. J., Argüello G. A. Binding of $[Cr(phen)_3]^{3+}$ to transferrin at extracellular and endosomal pHs: Potential application in photodynamic therapy. Biochim Biophys Acta. 2014 Jun. 25. pii: S0304-4165(14)00230-X. doi: 10.1016/j.bbagen.2014.06.010.

Gaspar M., Radomska A., Gobbo O. L., Bakowsky U., Radomski M. W., Ehrhardt C., 2012. Targeted delivery of transferrin-conjugated liposomes to an orthotopic model of lung cancer in nude rats. J. Aerosol Med. Pulm. Drug Deliv. http://dx.doi.org/10.1089/jamp. 2011.0928.

Gijsens A., Derycke A., Missiaen L., De Vos D., Huwyler J., Eberle A., et al. Targeting of the photocytotoxic compound AlPcS4 to Hela cells by transferrin conjugated PEG-liposomes. Int J Cancer, 2002, 101: 78-85

Graf N., Lippard S. J. Redox activation of metal-based prodrugs as a strategy for drug delivery. Adv. Drug Deliv. Rev. 2012, 64(11): 993-1004. doi:10.1016/j.addr.2012.01.007.

Guo W., Zheng W., Luo Q., Li X., Zhao Y., Xiong S., Wang F. Transferrin Serves As a Mediator to Deliver Organometallic Ruthenium(II) Anticancer Complexes into Cells. Inorg. Chem. 2013, 52, 328-5338. dx.doi.org/10.1021/ic4002626.

He H, Cattran A W, Nguyen T, Nieminen A L, Xu P. Triple-responsive expansile nanogel for tumor and mitochondria targeted photosensitizer delivery. Biomaterials. 2014 Aug. 21. pii: S0142-9612(14)00891-6. doi: 10.1016/j.biomaterials.2014.08.004.

Heger Z., Skalickova S., Zitka O., Adam V., Kizek R. Apoferritin applications in medicine. Nanomedicine (Lond.), 2014, 9, 2233-2245.

MaHam A., Tang Z., Wu H., Wang J., Lin Y. Protein-based nanomedicine platforms for drug delivery. 2009, 5, 1706-1722.

Nkepang G., Bio M., Rajaputra P., Awuah S. G., You Y. Folate Receptor-mediated Enhanced and Specific Delivery of Far-red Light-activatable Prodrugs of Combretastatin A-4 to FR-positive Tumor. Bioconjug Chem. 2014 Oct. 28.

Paszko E., Vaz G. M., Ehrhardt C., Senge M. O. Transferrin conjugation does not increase the efficiency of liposomal Foscan during in vitro photodynamic therapy of oesophageal cancer. Eur J Pharm Sci. 2013 Jan. 23; 48(1-2):202-10. doi: 10.1016/j.ejps.2012.10.018.

Pongratz M., Schluga P., Jakupec, M. A., Arion V. B., Hartinger C. G. Allmaier G., Keppler B. K. Transferrin binding and transferrin-mediated cellular uptake of the ruthenium coordination compound KP1019, studied by means of AAS, ESI-MS and CD spectroscopy. J. Anal. At. Specrom., 2004, 19, 46-51.

Sardar S., Chaudhuri S., Kar P., Sarkar S., Lemmens P., Pal S. K. Direct observation of key photoinduced dynamics in a potential nano-delivery vehicle of cancer drugs. Phys Chem Chem Phys. 2014 Nov. 5.

Szwed M., Kania K. D., Jozwiak Z. Relationship between therapeutic efficacy of doxorubicin-transferrin conjugate and expression of P-glycoprotein in chronic erythromyeloblastoid leukemia cells sensitive and resistant to doxorubicin. Cell Oncol (Dordr). 2014 December; 37(6):421-8. doi: 10.1007/s13402-014-0205-5. Epub 2014 Nov. 20.

Temizel E., Sagir T., Ayan E., Isik S., Ozturk R. Delivery of lipophilic porphyrin by liposome vehicles: Preparation and Photodynamic therapy activity against cancer cell lines. Photodiagnosis Photodyn Ther. 2014 Aug. 5. pii: S1572-1000(14)00097-0. doi: 10.1016/j.pdpdt.2014.07.006.

Wong B. S., Yoong S. L., Jagusiak A., Panczyk T., Ho H. K., Ang W. H., Pastorin G. Carbon nanotubes for delivery of small molecule drugs. Adv Drug Deliv Rev. 2013 December; 65(15):1964-2015. doi: 10.1016/j.addr.2013.08.005. Epub 2013 Aug. 14.

Yang K., Feng L., Liu Z. The advancing uses of nanographene in drug delivery. Expert Opin Drug Deliv. 2014 December 3:1-12.

Yin M., Ju E., Chen Z., Li Z., Ren J., Qu X. Upconverting Nanoparticles with a Mesoporous $TiO_2$ Shell for Near-Infrared-Triggered Drug Delivery and Synergistic Targeted Cancer Therapy. Chemistry. 2014 Sep. 8. doi: 10.1002/chem.201403733.

Yu J., Hsu C. H., Huang C. C., Chang P. Y. Development of Therapeutic Au-Methylene Blue Nanoparticles for Targeted Photodynamic Therapy of Cervical Cancer Cells. ACS Appl Mater Interfaces. 2014 Dec. 10.

Yuan Y., Liu B. Self-Assembled Nanoparticles Based on PEGylated Conjugated Polyelectrolyte and Drug Molecules for Image-Guided Drug Delivery and Photodynamic Therapy. ACS Appl Mater Interfaces. 2014 Jul. 30.

Zhang H., Hou L., Jiao X., Ji Y., Zhu X., Zhang Z. Transferrin-mediated fullerenes nanoparticles as $Fe^{2+}$-dependent drug vehicles for synergistic anti-tumor efficacy. Biomaterials. 2015, 37, 353-366. doi: 10.1016/j.biomaterials.2014.10.031.

Zhen Z., Tang W., Chuang Y. J., Todd T., Zhang W., Lin X., Niu G., Liu G., Wang L., Pan Z., Chen X., Xie J. Tumor vasculature targeted photodynamic therapy for enhanced delivery of nanoparticles. ACS Nano. 2014 Jun. 24; 8(6):6004-13. doi: 10.1021/nn501134q. Epub 2014 May 12.

What is claimed is:

1. A method for treating a condition associated with hyperproliferating cells, said method comprising administering to a subject having the condition a metal-binding glycoprotein and a chemotherapeutic compound containing at least one transition metal, wherein the metal-binding glycoprotein and the chemotherapeutic compound containing at least one transition metal are administered in a combined amount effective to treat the condition, and the chemotherapeutic compound has the formula(I):

(I)

including hydrates, solvates, pharmaceutically acceptable salts, prodrugs and complexes thereof, wherein:

M at each occurrence is independently selected from the group consisting of osmium, manganese, molybdenum, rhenium, ruthenium, iron, cobalt, rhodium, iridium, nickel, platinum, and copper;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2, 3, 4, or 5;

q is independently at each occurrence 0, 1, or 2;

y is independently at each occurrence 0, 1, or 2;

z is independently at each occurrence 1, 2, or 3;

$Lig^1$ is a bidentate ligand that at each occurrence is each independently selected from the group consisting of

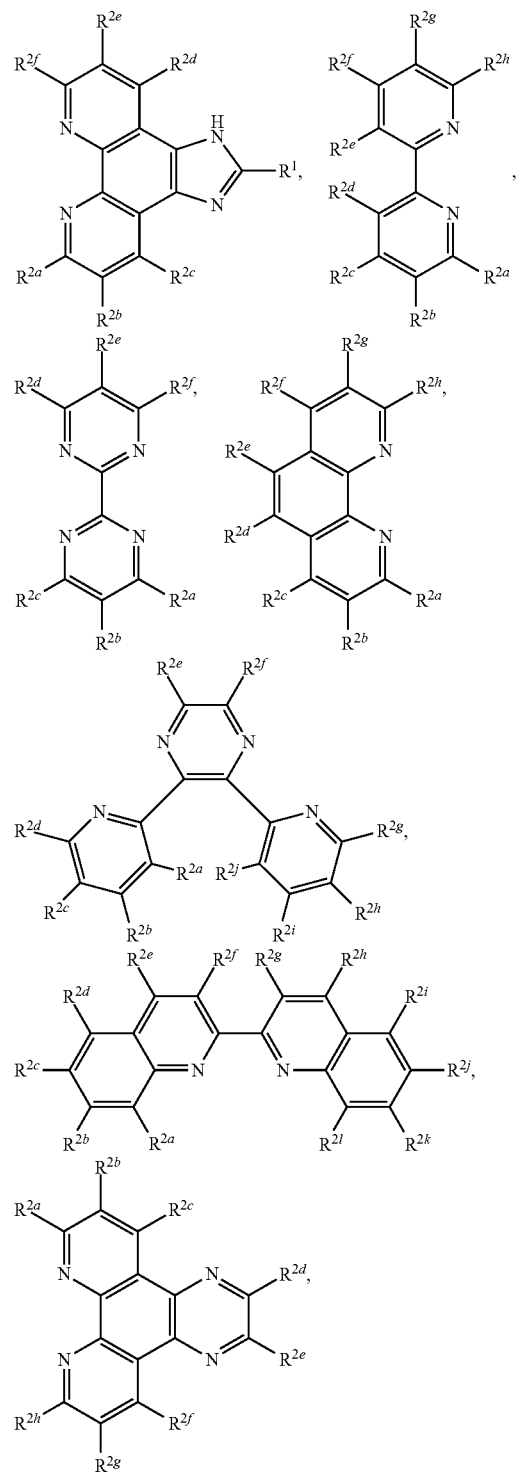

-continued
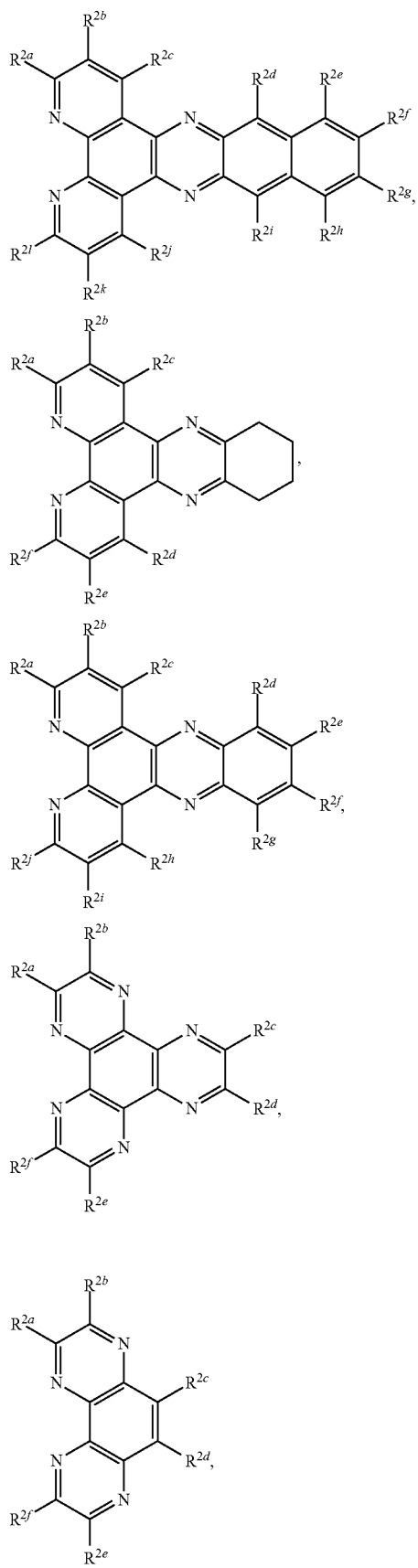
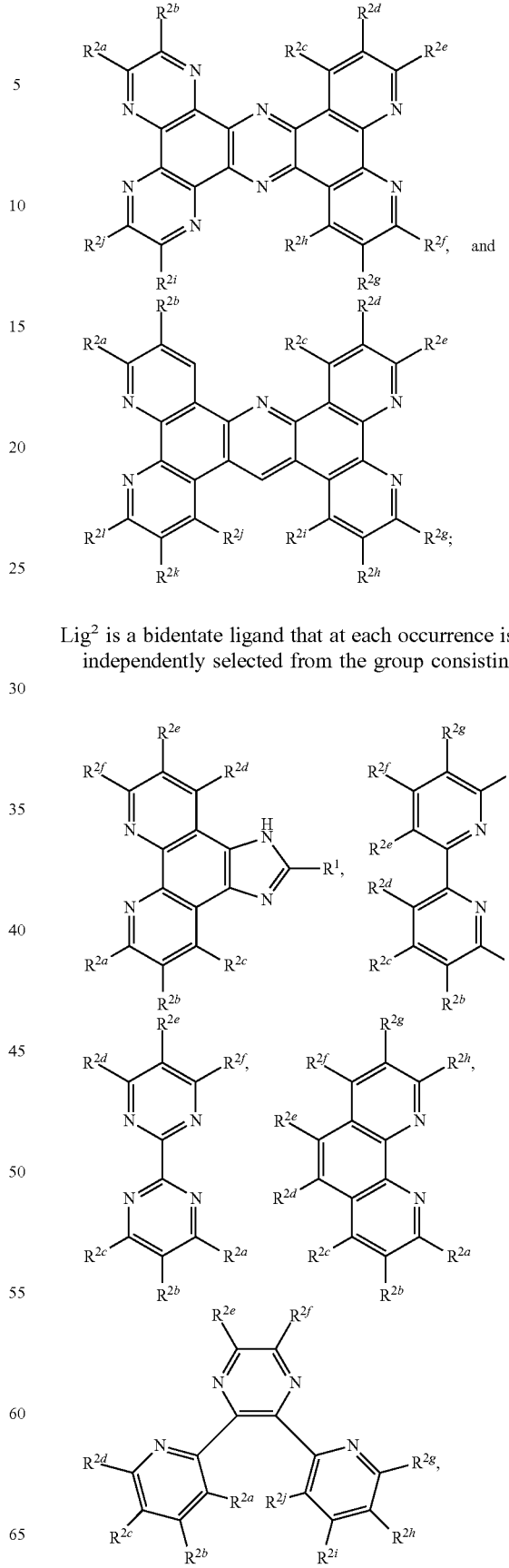
Lig² is a bidentate ligand that at each occurrence is each independently selected from the group consisting of -continued
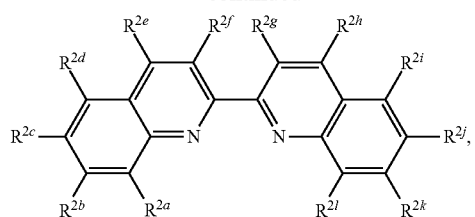
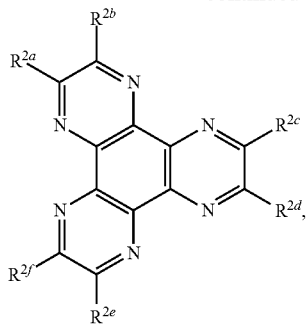
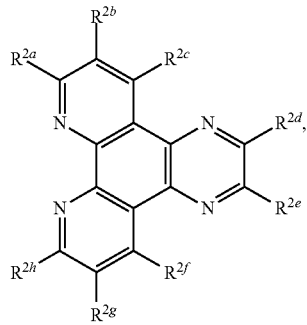
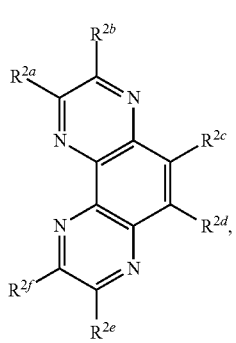
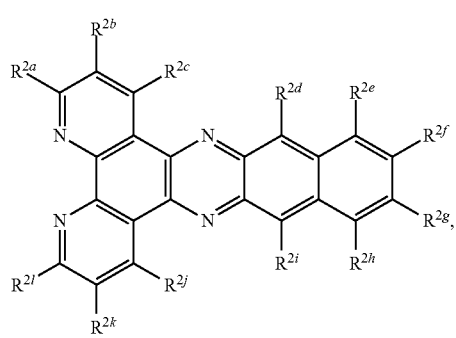
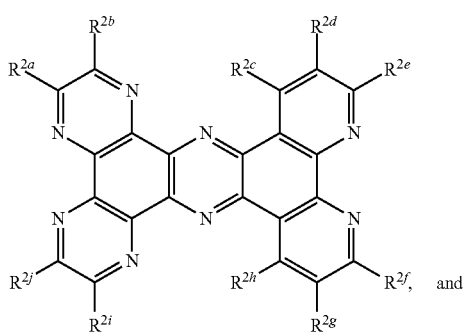
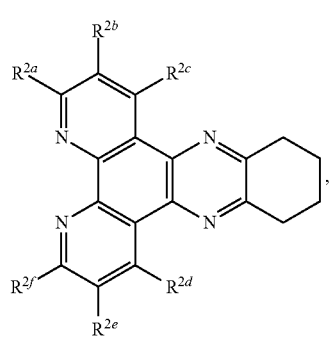
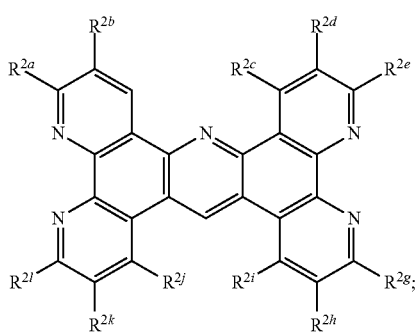
and
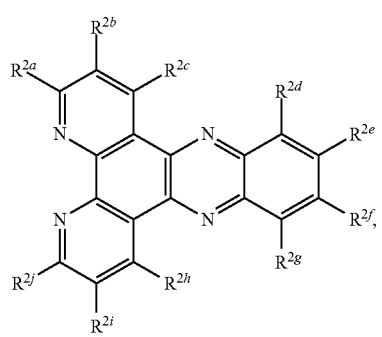
Lig³ is a bidentate ligand that at each occurrence is each independently selected from the group consisting of

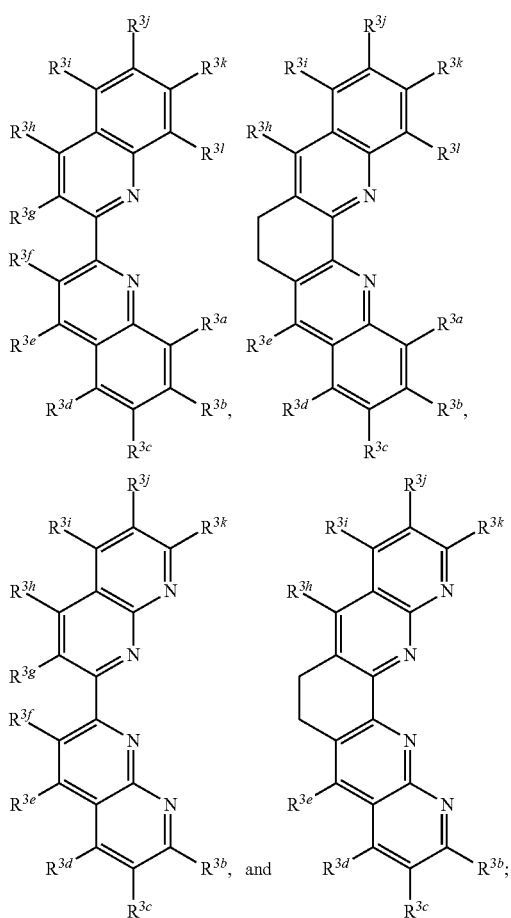
$R^1$ is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,
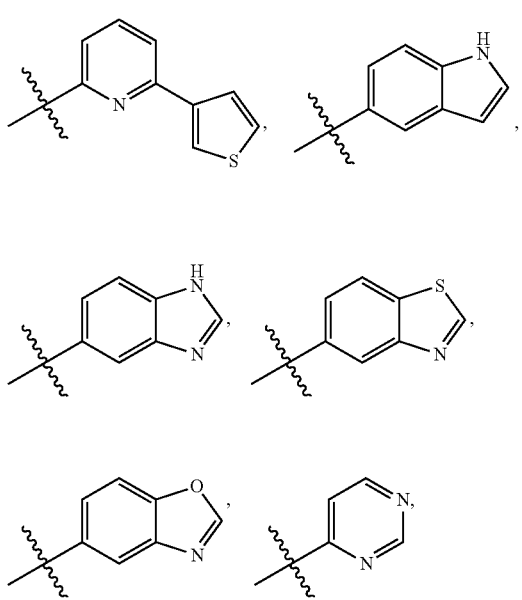
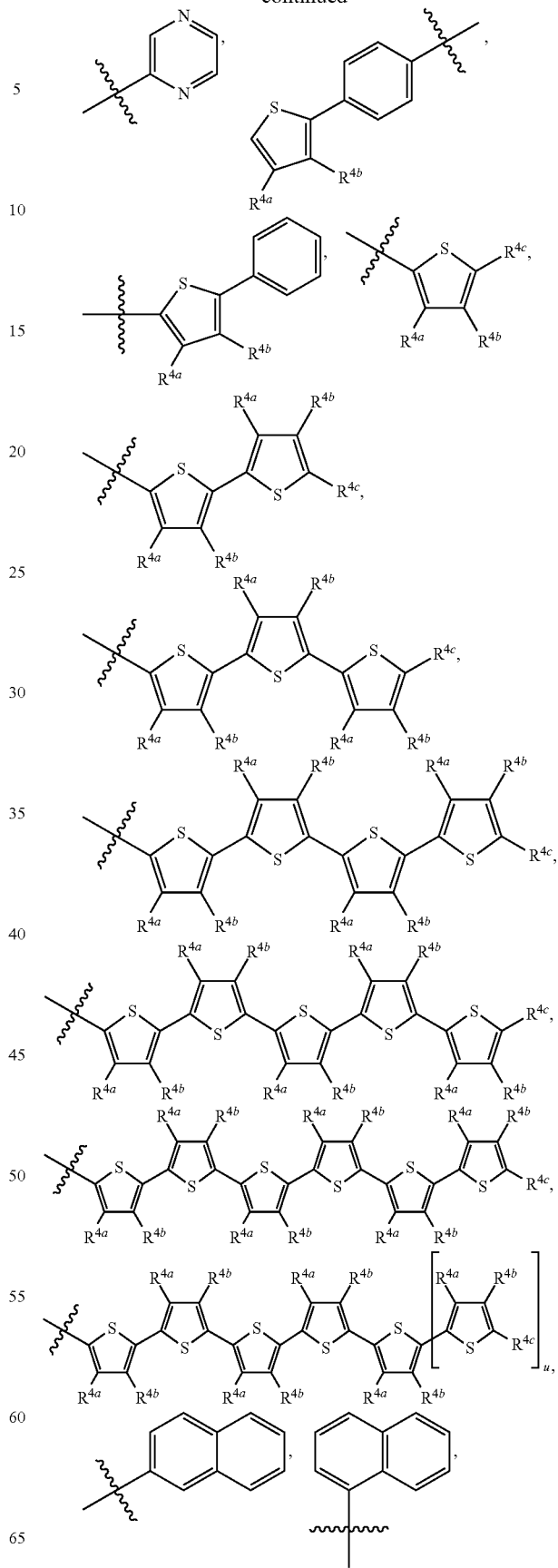

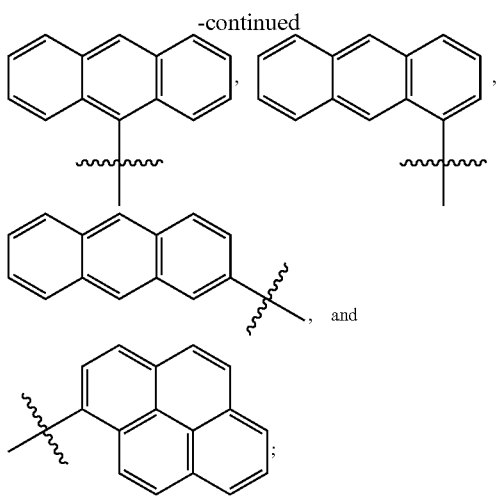

u is an interger;

$R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^{2k}$, and $R^{2l}$ at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6{}_2$, $NR^7{}_2$, $SO_3H$, sulfate, sulfonate, optionally substituted aryl, optionally substituted aryloxy, optionally substituted heteroaryl, and optionally substituted heterocycle, $R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;

$R^{4a}$, $R^{4b}$, and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence are each independently selected from the group consisting of hydrogen and optionally substituted alkyl;

$R^6$ at each occurrence are each independently selected from the group consisting of hydrogen and optionally substituted alkyl;

$R^7$ at each occurrence are each independently selected from the group consisting of hydrogen and optionally substituted alkyl; and $R^8$ at each occurrence are each independently selected from the group consisting of hydrogen and optionally substituted alkyl.

2. The method of claim 1, further comprising irradiating the subject with light effective to activate the chemotherapeutic compound.

3. The method of claim 2, wherein the metal-binding glycoprotein is effective to provide at least one of the following advantages relative to treatment by the chemotherapeutic compound without the glycoprotein: (a) increased uptake by cancer cells; (b) increased uptake by tumors; (c) increased efficacy at wavelengths longer than 600 nm; (d) increased efficacy at wavelengths less than or equal to 600 nm; (e) improved absorbance at wavelengths longer than 600 nm; (f) improved absorbance at wavelengths less than or equal to 600 nm; (g) increased production of reactive oxygen species; (h) increased photodynamic therapy effect under non-hypoxic conditions; (i) increased photodynamic therapy effect under hypoxic conditions; (j) increased LD50; (k) increased MTD; (l) increased photostability; and (m) increased shelf-life.

4. The method of claim 1, wherein the metal-binding glycoprotein and the chemotherapeutic compound containing at least one transition metal are administered in a combination dosage form or are co-administered from two or more independent sources.

5. The method of claim 1, wherein the metal-binding glycoprotein is transferrin and M is osmium, ruthenium or rhodium.

6. The method of claim 1, wherein the metal-binding glycoprotein is transferrin and the chemotherapeutic compound has the formula (II)

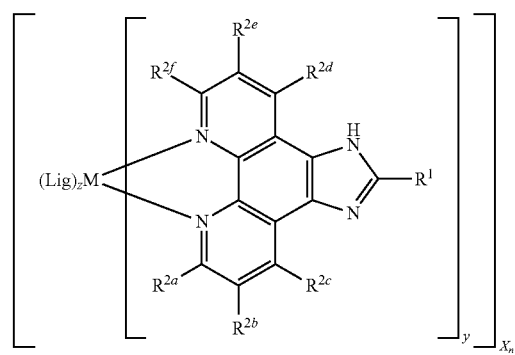

(II)

including hydrates, solvates, pharmaceutically acceptable salts, prodrugs and complexes thereof, wherein:

M is selected from the group consisting of manganese, molybdenum, rhenium, iron, ruthenium, osmium, cobalt, rhodium, iridium, nickel, platinum, and copper;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2, 3, 4, or 5;

y=1, 2, or 3;

z=0, 1, or 2;

Lig at each occurrence is independently selected from the group consisting of

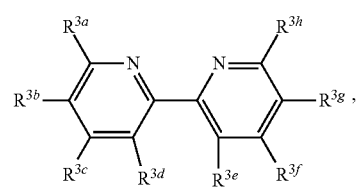

-continued
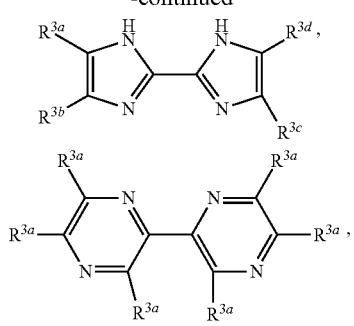
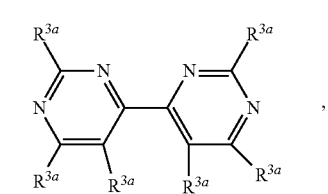
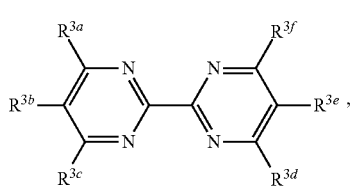
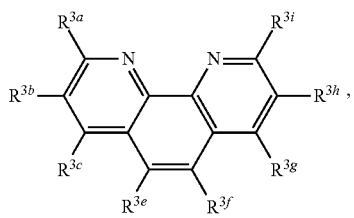
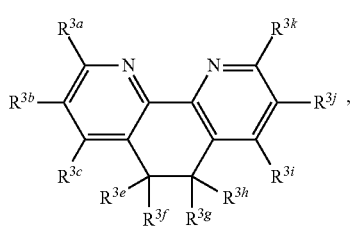
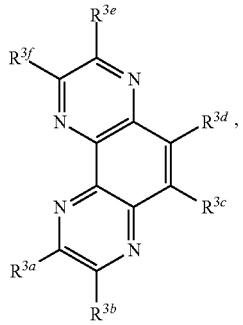
-continued
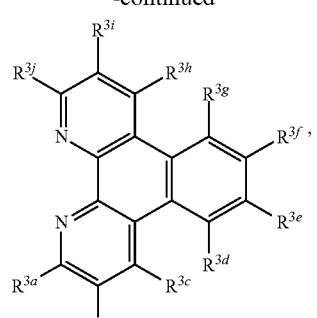
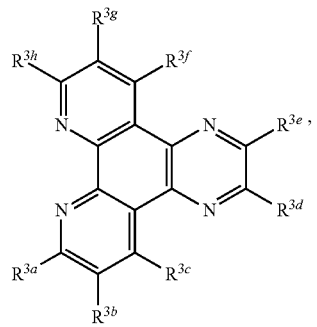
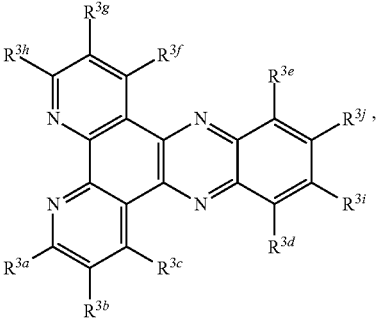
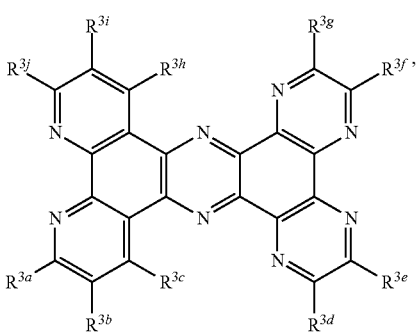

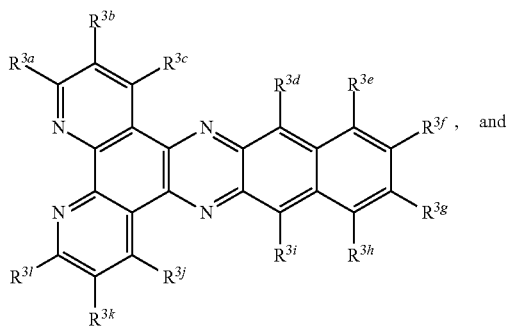, and 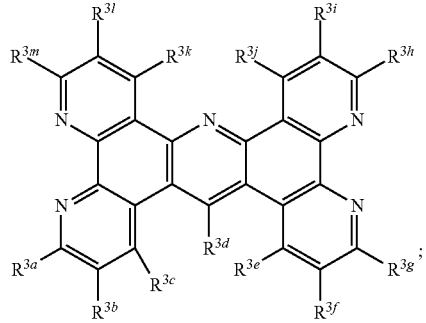;
$R^1$ is selected from the group consisting of
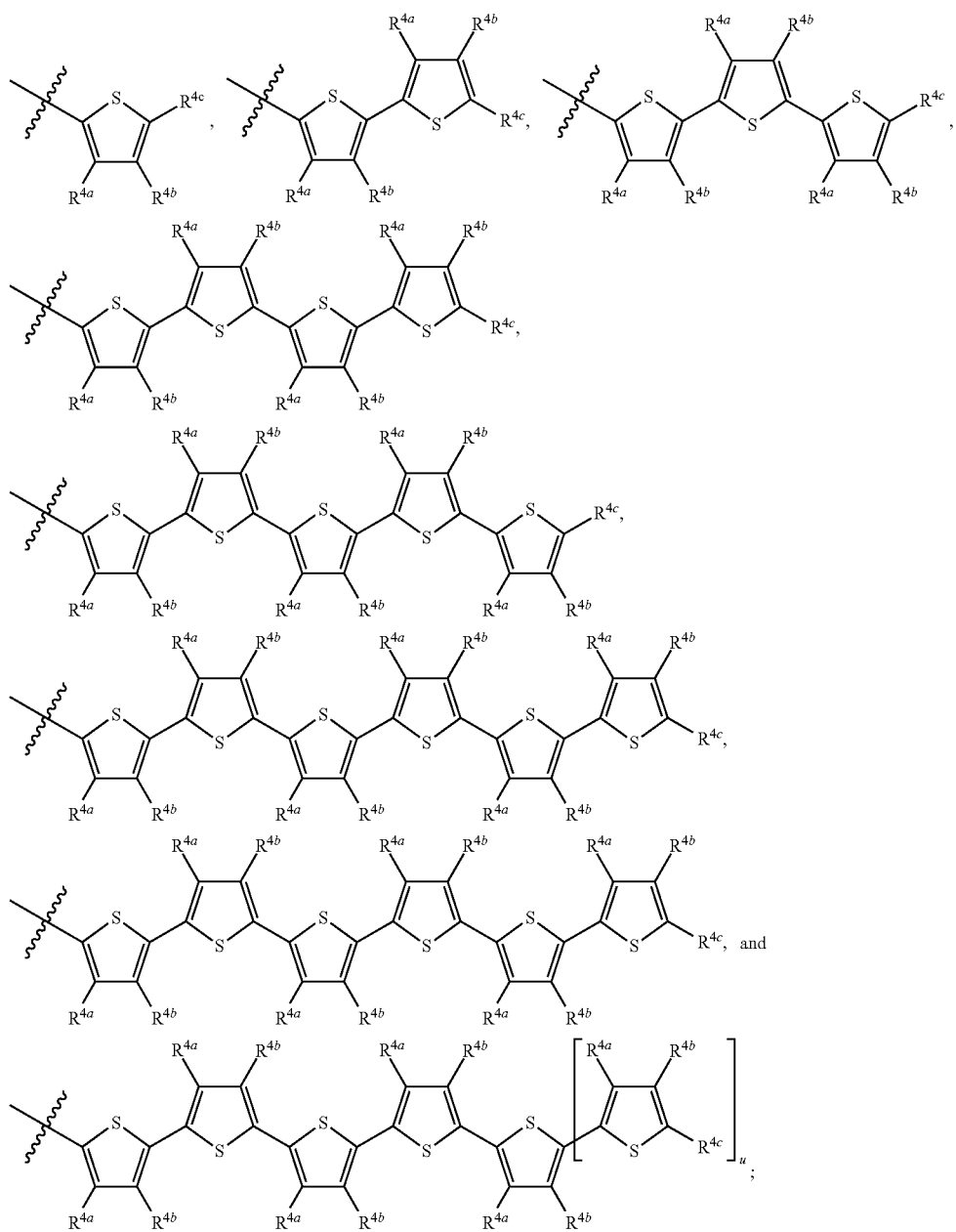

u is an integer;

$R^{2a}$, $R^{2b}$, $R^{2c}$, $R^{2d}$, $R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, $R^{3l}$, and $R^{3m}$ at each occurrence are each independently selected from the group consisting of hydrogen, C1-6 optionally substituted alkyl, C1-6 optionally substituted branched alkyl, C1-6 optionally substituted haloalkyl, C1-6 optionally substituted alkoxy, and $CO_2R^8$;

$R^{4a}$, $R^{4b}$, and $R^{4c}$ at each occurrence are each independently selected from the group consisting of hydrogen, C1-6 optionally substituted alkyl, C1-6 optionally substituted branched alkyl, C1-6 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl; and $R^8$ at each occurrence is independently selected from the group consisting of hydrogen and optionally substituted alkyl.

7. The method of claim 1, wherein the at least one transition metal is at least one of Ru, Rh, Os and Ir.

8. The method of claim 1, wherein the metal-binding glycoprotein is a recombinant human transferrin.

9. The method of claim 1, wherein the condition treated by the method is at an immune privileged site, the metal-binding glycoprotein and the chemotherapeutic compound containing at least one transition metal are systemically administered in a form of a complex, and the complex crosses at least one of the blood-brain barrier, the retina-blood barrier and the blood-cerebrospinal fluid barrier to accumulate at the immune privileged site.

10. The method of claim 9, wherein the complex crosses the blood-brain barrier and preferentially accumulates in a brain tumor being treated by the method.

11. The method of claim 3, wherein the condition treated by the method is at an immune privileged site, the metal-binding glycoprotein and the chemotherapeutic compound containing at least one transition metal are systemically administered in a form of a complex, and the complex crosses at least one of the blood-brain barrier, the retina-blood barrier and the blood-cerebrospinal fluid barrier to accumulate at the immune privileged site.

12. The method of claim 5, wherein the condition treated by the method is at an immune privileged site, the metal-binding glycoprotein and the chemotherapeutic compound containing at least one transition metal are systemically administered in a form of a complex, and the complex crosses at least one of the blood-brain barrier, the retina-blood barrier and the blood-cerebrospinal fluid barrier to accumulate at the immune privileged site.

13. The method of claim 6, wherein the condition treated by the method is at an immune privileged site, the metal-binding glycoprotein and the chemotherapeutic compound containing at least one transition metal are systemically administered in a form of a complex, and the complex crosses at least one of the blood-brain barrier, the retina-blood barrier and the blood-cerebrospinal fluid barrier to accumulate at the immune privileged site.

14. The method of claim 1, further comprising irradiating the subject with ionizing radiation effective to activate the chemotherapeutic compound.

15. The method of claim 1, wherein the metal-binding glycoprotein and the chemotherapeutic compound containing at least one transition metal are administered systemically in a form of a complex, the chemotherapeutic compound is a photodynamic compound, and the complex further comprises at least one active pharmaceutical ingredient.

16. The method of claim 15, wherein the at least one active pharmaceutical ingredient is an anti-neoplastic agent that is free of any transition metals.

17. The method of claim 15, wherein the complex crosses at least one of the blood-brain barrier, the retina-blood barrier and the blood-cerebrospinal fluid barrier to accumulate at an immune privileged site.

* * * * *